United States Patent
Chang et al.

(10) Patent No.: US 11,498,419 B2
(45) Date of Patent: Nov. 15, 2022

(54) MOVABLE CARRIER AUXILIARY SYSTEM

(71) Applicant: ABILITY OPTO-ELECTRONICS TECHNOLOGY CO., LTD., Taichung (TW)

(72) Inventors: Yeong-Ming Chang, Taichung (TW); Chien-Hsun Lai, Taichung (TW); Yao-Wei Liu, Taichung (TW)

(73) Assignee: ABILITY OPTO-ELECTRON ICS TECHNOLOGY CO., LTD., Taichung (TW)

( * ) Notice: Subject to any disclaimer, the term of this patent is extended or adjusted under 35 U.S.C. 154(b) by 490 days.

(21) Appl. No.: 16/665,835

(22) Filed: Oct. 28, 2019

(65) Prior Publication Data
US 2020/0346545 A1 Nov. 5, 2020

(30) Foreign Application Priority Data
Apr. 30, 2019 (TW) ................................. 108115010

(51) Int. Cl.
*B60K 28/00* (2006.01)
*B60K 28/06* (2006.01)
(Continued)

(52) U.S. Cl.
CPC ............ *B60K 28/063* (2013.01); *A61B 5/021* (2013.01); *A61B 5/024* (2013.01); *A61B 5/082* (2013.01);
(Continued)

(58) Field of Classification Search
CPC ....... B60K 28/063; A61B 5/163; A61B 5/021; A61B 5/024; A61B 5/0816; A61B 5/082;
(Continued)

(56) References Cited

U.S. PATENT DOCUMENTS 6,575,902 B1 * 6/2003 Burton .................. B60W 40/08
600/595
7,027,621 B1 * 4/2006 Prokoski .............. G06V 40/165
340/576
(Continued)

FOREIGN PATENT DOCUMENTS

EP 2296008 A1 3/2011
EP 2092889 B1 2/2019
(Continued)

OTHER PUBLICATIONS

Search report for TW108115010, dated Jun. 1, 2021, Total of 2 pages.
(Continued)

*Primary Examiner* — Zhen Y Wu
(74) *Attorney, Agent, or Firm* — Apex Juris, PLLC; Hilde Coeckx

(57) ABSTRACT

A movable carrier auxiliary system includes a driver state detecting device and a warning device. The driver state detecting device includes a physiological state detecting module, a storage module, and an operation module. The physiological state detecting module is adapted to detect a physiological state of a driver. The storage module is disposed in a movable carrier and stores an allowable parameter corresponding to the at least one physiological state. The operation module is disposed in the movable carrier and is electrically connected to the physiological state detecting module and the storage module to detect whether the at least one physiological state of the driver exceeds the allowable parameter or not, and to correspondingly generate a detection signal. The warning device generate a warning message when the detection signal that the at least one physiological state of the driver exceeds the allowable parameter is received.

40 Claims, 11 Drawing Sheets

(51) Int. Cl.
| | |
|---|---|
| *B60W 40/08* | (2012.01) |
| *H04N 5/235* | (2006.01) |
| *H04N 5/225* | (2006.01) |
| *G02F 1/155* | (2006.01) |
| *G02F 1/157* | (2006.01) |
| *A61B 5/16* | (2006.01) |
| *A61B 5/024* | (2006.01) |
| *A61B 5/021* | (2006.01) |
| *A61B 5/145* | (2006.01) |
| *A61B 5/08* | (2006.01) |
| *A61B 5/00* | (2006.01) |
| *A61B 5/18* | (2006.01) |
| *B60Q 9/00* | (2006.01) |
| *G06V 10/147* | (2022.01) |
| *G06V 20/59* | (2022.01) |
| *B60R 11/00* | (2006.01) |
| *B60R 11/04* | (2006.01) |

(52) U.S. Cl.
CPC ........ *A61B 5/0816* (2013.01); *A61B 5/14532* (2013.01); *A61B 5/14542* (2013.01); *A61B 5/14546* (2013.01); *A61B 5/163* (2017.08); *A61B 5/18* (2013.01); *A61B 5/746* (2013.01); *B60Q 9/00* (2013.01); *B60W 40/08* (2013.01); *G02F 1/155* (2013.01); *G02F 1/157* (2013.01); *G06V 10/147* (2022.01); *G06V 20/597* (2022.01); *H04N 5/2254* (2013.01); *H04N 5/2351* (2013.01); *B60R 11/04* (2013.01); *B60R 2011/0003* (2013.01); *B60W 2040/0836* (2013.01); *B60W 2040/0872* (2013.01); *B60W 2540/26* (2013.01)

(58) Field of Classification Search
CPC ............ A61B 5/14532; A61B 5/14542; A61B 5/14546; A61B 5/18; A61B 5/746; G06V 20/597; G06V 10/147; B60Q 9/00; B60W 40/08; B60W 2040/0836; B60W 2040/0872; B60W 2540/26; G02F 1/155; G02F 1/157; H04N 5/2254; H04N 5/2351; B60R 11/04; B60R 2011/0003
USPC ....................................................... 180/272
See application file for complete search history.

(56) References Cited

U.S. PATENT DOCUMENTS

| | | | |
|---|---|---|---|
| 9,456,259 B1* | 9/2016 | Liao ................... | A61B 5/0205 |
| 9,775,565 B1* | 10/2017 | Berg-Neuman ...... | B60W 40/08 |
| 2007/0182529 A1* | 8/2007 | Dobler ................. | B60K 28/066 |
| | | | 340/438 |
| 2010/0201816 A1* | 8/2010 | Lee ........................ | B60R 1/12 |
| | | | 349/1 |
| 2010/0312431 A1* | 12/2010 | Kaschner ............ | B60K 28/063 |
| | | | 701/1 |
| 2015/0103014 A1* | 4/2015 | Kim ...................... | G06F 3/0304 |
| | | | 345/173 |
| 2015/0177493 A1* | 6/2015 | Asami ...................... | G02B 9/62 |
| | | | 359/713 |
| 2015/0216466 A1* | 8/2015 | Kronberg ............ | A61B 5/4809 |
| | | | 702/19 |
| 2015/0229341 A1* | 8/2015 | Fung ...................... | B60R 25/25 |
| | | | 702/191 |
| 2016/0001781 A1* | 1/2016 | Fung ...................... | G16H 50/20 |
| | | | 701/36 |
| 2016/0035273 A1* | 2/2016 | VanderPloeg ............ | G09G 3/19 |
| | | | 345/205 |
| 2016/0052391 A1* | 2/2016 | Walsh .................... | G08B 21/06 |
| | | | 340/575 |
| 2016/0133117 A1* | 5/2016 | Geller .................... | A61B 5/746 |
| | | | 340/457 |
| 2016/0174890 A1* | 6/2016 | Ko ....................... | A61B 5/6893 |
| | | | 340/576 |
| 2016/0280230 A1* | 9/2016 | Hsieh .................... | B60K 28/066 |
| 2017/0003478 A1* | 1/2017 | Liu ........................ | G02B 13/004 |
| 2017/0017065 A1* | 1/2017 | Liu ............................ | G02B 9/60 |
| 2017/0181713 A1* | 6/2017 | Feng ....................... | A61B 5/0205 |
| 2019/0299999 A1* | 10/2019 | Liu ........................ | A61B 5/7267 |
| 2019/0375426 A1* | 12/2019 | Suga ..................... | B60W 40/08 |

FOREIGN PATENT DOCUMENTS

| | | |
|---|---|---|
| TW | 436436 B | 5/2001 |
| TW | 201433483 A | 9/2014 |
| TW | M557687 U | 4/2018 |
| TW | I638739 B | 10/2018 |
| TW | M585412 U | 10/2019 |
| WO | 2015000087 A1 | 1/2015 |
| WO | 2018146266 A1 | 8/2018 |

OTHER PUBLICATIONS

English abstract for EP2092889, Total of 1 page.
English abstract for TW436436, Total of 1 page.
English abstract for TW201433483, Total of 1 page.
English abstract for TWI638739, Total of 1 page.
English abstract for TWM557687, Total of 1 page.
English abstract for TWM585412, Total of 1 page.

* cited by examiner

MOVABLE CARRIER AUXILIARY SYSTEM

BACKGROUND OF THE INVENTION

Technical Field

The present invention relates to a movable carrier auxiliary system, and more particularly to an auxiliary system capable of determining a physiological state of a driver.

Description of Related Art

With frequent commercial activities and the rapid expansion of transportation logistics, people are more dependent on the mobile vehicle such as car or motorcycle. At the same time, drivers are paying more and more attention to the protection of their lives and property when driving, and therefore, in addition to the performance and the comfort of the mobile vehicle, it is also considered whether the mobile vehicle to be purchased provides sufficient safety guards or auxiliary devices. Under this trend, in order to increase the safety of vehicles, automobile manufacturers or vehicle equipment design manufacturers have developed various driving safety protection devices or auxiliary devices, such as rearview mirrors, driving recorders, a panoramic image instant displaying of blind vision areas, a global positioning system that records the driving path at any time, and etc.

In addition, with the rapid development of digital cameras and computer visions in daily life, the digital cameras have been applied to driving assistance systems, hoping to reduce the accident rate of traffic accidents through the application of artificial intelligence.

For movable carriers that require driver to drive, the movable carrier is controlled by the driver. When the driver is in good physical condition, the driver can control the movable carrier safely. However, when the driver is in poor health, a situation that the driver could not manipulate or could mistakenly manipulate the movable carrier may happen. For example, the driver suddenly has a myocardial infarction during driving. If the driver is unable to control or mishandle the movable carrier, it may cause damage to the movable carrier, or even endanger the safety of the person in the movable carrier.

Therefore, there is a need for the manufacturers to develop an auxiliary system which could accurately detect the physiological state of the driver, improving the driving safety.

BRIEF SUMMARY OF THE INVENTION

The aspect of embodiment of the present disclosure directs to a movable carrier auxiliary system, which includes a driver state detecting device and a warning device, wherein the driver state detecting device includes a physiological state detecting module, a storage module, and an operation module. The physiological state detecting module is adapted to detect at least one physiological state of a driver. The storage module is disposed in a movable carrier and stores an allowable parameter corresponding to the at least one physiological state. The operation module is disposed in the movable carrier and is electrically connected to the physiological state detecting module and the storage module, thereby to detect whether the at least one physiological state of the driver exceeds the allowable parameter, and to generate a detection signal correspondingly. The warning device is electrically connected to the operation module, thereby to generate a warning message when a detection signal that the physiological state of the driver exceeds the allowable parameter is received.

Further, the physiological state detecting module further includes an image capturing module which is adapted to capturing a driver image located on a driver seat in the movable carrier. The operation module determines whether the at least one physiological state of the driver exceeds the allowable parameter or not based on the driver image, and generates a detection signal correspondingly. The image capturing module includes a lens group; the lens group includes at least two lenses having refractive power and satisfies: $1.0 \leq f/HEP \leq 10.0$; $0 \deg \leq HAF \leq 150 \deg$; and $0.9 \leq 2(ARE/HEP) \leq 2.0$, wherein f is a focal length of the lens group; HEP is an entrance pupil diameter of the lens group; HAF is half a maximum visual angle of the lens group; ARE is a profile curve length measured from a start point where an optical axis of the at least one lens group passes through any surface of one of the at least two lenses, along a surface profile of the corresponding lens, and finally to a coordinate point of a perpendicular distance where is a half of the entrance pupil diameter away from the optical axis.

The lens group uses structural size design and combination of refractive powers, convex and concave surfaces of at least two optical lenses (the convex or concave surface in the disclosure denotes the geometrical shape of an image-side surface or an object-side surface of each lens on an optical axis) to reduce the size and increase the quantity of incoming light of the optical image capturing system, thereby the optical image capturing system could have a better amount of light entering therein and could improve imaging total pixels and imaging quality for image formation.

In an embodiment, the lens group satisfies: $0.9 \leq ARS/EHD \leq 2.0$, wherein for any surface of any lens, ARS is a profile curve length measured from a start point where the optical axis passes therethrough, along a surface profile thereof, and finally to an end point of a maximum effective radius thereof; EHD is a maximum effective radius thereof.

In an embodiment, the lens group further satisfies: $PLTA \leq 100 \ \mu m$; $PSTA \leq 100 \ \mu m$; $NLTA \leq 100 \ \mu m$; $NSTA \leq 100 \ \mu m$; $SLTA \leq 100 \ \mu m$; $SSTA \leq 100 \ \mu m$; and $|TDT| \leq 250\%$, wherein HOI is a maximum imaging height for image formation perpendicular to the optical axis on an image plane of the image capturing module; PLTA is a transverse aberration at 0.7 HOI in a positive direction of a tangential ray fan aberration of the image capturing module after the longest operation wavelength passing through an edge of the entrance pupil; PSTA is a transverse aberration at 0.7 HOI in the positive direction of the tangential ray fan aberration of the image capturing module after the shortest operation wavelength passing through the edge of the entrance pupil; NLTA is a transverse aberration at 0.7 HOI in a negative direction of the tangential ray fan aberration of the image capturing module after the longest operation wavelength passing through the edge of the entrance pupil; NSTA is a transverse aberration at 0.7 HOI in the negative direction of the tangential ray fan aberration of the image capturing module after the shortest operation wavelength passing through the edge of the entrance pupil; SLTA is a transverse aberration at 0.7 HOI of a sagittal ray fan aberration of the image capturing module after the longest operation wavelength passing through the edge of the entrance pupil; SSTA is a transverse aberration at 0.7 HOI of the sagittal ray fan aberration of the image capturing module after the shortest operation wavelength passing through the edge of the entrance pupil; and TDT is a TV distortion of the image capturing module upon image formation.

In an embodiment, the lens group includes four lenses having refractive power, which is constituted by a first lens, a second lens, a third lens, and a fourth lens in order along the optical axis from an object side to an image side; and the lens group satisfies: $0.1 \leq \text{InTL/HOS} \leq 0.95$; wherein HOS is a distance in parallel with the optical axis between an object-side surface of the first lens and an image plane of the image capturing module; InTL is a distance in parallel with the optical axis from the object-side surface of the first lens to an image-side surface of the fourth lens.

In an embodiment, the lens group includes five lenses having refractive power, which is constituted by a first lens, a second lens, a third lens, a fourth lens, and a fifth lens in order along the optical axis from an object side to an image side; and the lens group satisfies: $0.1 \leq \text{InTL/HOS} \leq 0.95$; wherein HOS is a distance in parallel with the optical axis between an object-side surface of the first lens and an image plane of the image capturing module; InTL is a distance in parallel with the optical axis from the object-side surface of the first lens to an image-side surface of the fifth lens.

In an embodiment, the lens group includes six lenses having refractive power, which is constituted by a first lens, a second lens, a third lens, a fourth lens, a fifth lens, and a sixth lens in order along the optical axis from an object side to an image side; and the lens group satisfies: $0.1 \leq \text{InTL/HOS} \leq 0.95$; wherein HOS is a distance in parallel with the optical axis between an object-side surface of the first lens and an image plane of the image capturing module; InTL is a distance in parallel with the optical axis from the object-side surface of the first lens to an image-side surface of the sixth lens.

In an embodiment, the lens group includes seven lenses having refractive power, which is constituted by a first lens, a second lens, a third lens, a fourth lens, a fifth lens, a sixth lens, and a seventh lens in order along the optical axis from an object side to an image side; and the lens group satisfies: $0.1 \leq \text{InTL/HOS} \leq 0.95$; wherein HOS is a distance in parallel with the optical axis between an object-side surface of the first lens and an image plane of the image capturing module; InTL is a distance in parallel with the optical axis from the object-side surface of the first lens to an image-side surface of the seventh lens.

In an embodiment, the lens group further includes an aperture, and the aperture satisfies: $0.2 \leq \text{InS/HOS} \leq 1.1$; wherein HOS is a distance in parallel with the optical axis between an object-side surface of the first lens and an image plane of the at least one lens group; InS is a distance on the optical axis between the aperture and an image plane of the image capturing module.

The lens parameter related to a length or a height in the lens:

A maximum height for image formation of the optical image capturing system is denoted by HOI. A height of the optical image capturing system (i.e., a distance between an object-side surface of the first lens and an image plane on an optical axis) is denoted by HOS. A distance from the object-side surface of the first lens to the image-side surface of the seventh lens is denoted by InTL. A distance from the first lens to the second lens is denoted by IN12 (for instance). A central thickness of the first lens of the optical image capturing system on the optical axis is denoted by TP1 (for instance).

The lens parameter related to a material in the lens:

An Abbe number of the first lens in the optical image capturing system is denoted by NA1 (for instance). A refractive index of the first lens is denoted by Nd1 (for instance).

The lens parameter related to a view angle of the lens:

A view angle is denoted by AF. Half of the view angle is denoted by HAF. A major light angle is denoted by MRA.

The lens parameter related to exit/entrance pupil in the lens:

An entrance pupil diameter of the optical image capturing system is denoted by HEP. For any surface of any lens, a maximum effective radius (EHD) is a perpendicular distance between an optical axis and a crossing point on the surface where the incident light with a maximum viewing angle of the optical image capturing system passing the very edge of the entrance pupil. For example, the maximum effective radius of the object-side surface of the first lens is denoted by EHD11, the maximum effective radius of the image-side surface of the first lens is denoted by EHD12, the maximum effective radius of the object-side surface of the second lens is denoted by EHD21, the maximum effective radius of the image-side surface of the second lens is denoted by EHD22, and so on.

The lens parameter related to an arc length of the shape of a surface and a surface profile:

For any surface of any lens, a profile curve length of the maximum effective radius is, by definition, measured from a start point where the optical axis of the belonging optical image capturing system passes through the surface of the lens, along a surface profile of the lens, and finally to an end point of the maximum effective radius thereof. In other words, the curve length between the aforementioned start and end points is the profile curve length of the maximum effective radius, which is denoted by ARS. For example, the profile curve length of the maximum effective radius of the object-side surface of the first lens is denoted by ARS11, the profile curve length of the maximum effective radius of the image-side surface of the first lens is denoted by ARS12, the profile curve length of the maximum effective radius of the object-side surface of the second lens is denoted by ARS21, the profile curve length of the maximum effective radius of the image-side surface of the second lens is denoted by ARS22, and so on.

For any surface of any lens, a profile curve length of half the entrance pupil diameter (HEP) is, by definition, measured from a start point where the optical axis of the belonging optical image capturing system passes through the surface of the lens, along a surface profile of the lens, and finally to a coordinate point of a perpendicular distance where is half the entrance pupil diameter away from the optical axis. In other words, the curve length between the aforementioned stat point and the coordinate point is the profile curve length of half the entrance pupil diameter (HEP), and is denoted by ARE. For example, the profile curve length of half the entrance pupil diameter (HEP) of the object-side surface of the first lens is denoted by ARE11, the profile curve length of half the entrance pupil diameter (HEP) of the image-side surface of the first lens is denoted by ARE12, the profile curve length of half the entrance pupil diameter (HEP) of the object-side surface of the second lens is denoted by ARE21, the profile curve length of half the entrance pupil diameter (HEP) of the image-side surface of the second lens is denoted by ARE22, and so on.

The lens parameter related to a depth of the lens shape:

A displacement from a point on the object-side surface of the sixth lens, which is passed through by the optical axis, to a point on the optical axis, where a projection of the maximum effective semi diameter of the object-side surface of the sixth lens ends, is denoted by InRS61 (the depth of the maximum effective semi diameter). A displacement from a point on the image-side surface of the sixth lens, which is passed through by the optical axis, to a point on the optical axis, where a projection of the maximum effective semi diameter of the image-side surface of the seventh lens ends, is denoted by InRS62 (the depth of the maximum effective semi diameter). The depth of the maximum effective semi diameter (sinkage) on the object-side surface or the image-side surface of any other lens is denoted in the same manner.

The lens parameter related to the lens shape:

A critical point C is a tangent point on a surface of a specific lens, and the tangent point is tangent to a plane perpendicular to the optical axis and the tangent point cannot be a crossover point on the optical axis. Following the above description, a distance perpendicular to the optical axis between a critical point CM on the object-side surface of the fifth lens and the optical axis is HVT51 (for instance), and a distance perpendicular to the optical axis between a critical point C52 on the image-side surface of the fifth lens and the optical axis is HVT52 (for instance). A distance perpendicular to the optical axis between a critical point C61 on the object-side surface of the sixth lens and the optical axis is HVT61 (for instance), and a distance perpendicular to the optical axis between a critical point C62 on the image-side surface of the sixth lens and the optical axis is HVT62 (for instance). A distance perpendicular to the optical axis between a critical point on the object-side or image-side surface of other lenses is denoted in the same manner.

The object-side surface of the seventh lens has one inflection point IF711 which is nearest to the optical axis, and the sinkage value of the inflection point IF711 is denoted by SGI711 (for instance). A distance perpendicular to the optical axis between the inflection point IF711 and the optical axis is HIF711 (for instance). The image-side surface of the seventh lens has one inflection point IF721 which is nearest to the optical axis, and the sinkage value of the inflection point IF721 is denoted by SGI721 (for instance). A distance perpendicular to the optical axis between the inflection point IF721 and the optical axis is HIF721 (for instance).

The object-side surface of the seventh lens has one inflection point IF712 which is the second nearest to the optical axis, and the sinkage value of the inflection point IF712 is denoted by SGI712 (for instance). A distance perpendicular to the optical axis between the inflection point IF712 and the optical axis is HIF712 (for instance). The image-side surface of the seventh lens has one inflection point IF722 which is the second nearest to the optical axis, and the sinkage value of the inflection point IF722 is denoted by SGI722 (for instance). A distance perpendicular to the optical axis between the inflection point IF722 and the optical axis is HIF722 (for instance).

The object-side surface of the seventh lens has one inflection point IF713 which is the third nearest to the optical axis, and the sinkage value of the inflection point IF713 is denoted by SGI713 (for instance). A distance perpendicular to the optical axis between the inflection point IF713 and the optical axis is HIF713 (for instance). The image-side surface of the seventh lens has one inflection point IF723 which is the third nearest to the optical axis, and the sinkage value of the inflection point IF723 is denoted by SGI723 (for instance). A distance perpendicular to the optical axis between the inflection point IF723 and the optical axis is HIF723 (for instance).

The object-side surface of the seventh lens has one inflection point IF714 which is the fourth nearest to the optical axis, and the sinkage value of the inflection point IF714 is denoted by SGI714 (for instance). A distance perpendicular to the optical axis between the inflection point IF714 and the optical axis is HIF714 (for instance). The image-side surface of the seventh lens has one inflection point IF724 which is the fourth nearest to the optical axis, and the sinkage value of the inflection point IF724 is denoted by SGI724 (for instance). A distance perpendicular to the optical axis between the inflection point IF724 and the optical axis is HIF724 (for instance).

An inflection point, a distance perpendicular to the optical axis between the inflection point and the optical axis, and a sinkage value thereof on the object-side surface or image-side surface of other lenses is denoted in the same manner.

The lens parameter related to an aberration:

Optical distortion for image formation in the optical image capturing system is denoted by ODT. TV distortion for image formation in the optical image capturing system is denoted by TDT. Further, the range of the aberration offset for the view of image formation may be limited to 50%-100% field. An offset of the spherical aberration is denoted by DFS. An offset of the coma aberration is denoted by DFC.

The length of the contour curve of any surface of a single lens in the range of the maximum effective radius affects the surface correction aberration and the optical path difference between the fields of view. The longer the profile curve length, the better the ability to correct the aberration, but at the same time It will increase the difficulty in manufacturing, so it is necessary to control the length of the profile curve of any surface of a single lens within the maximum effective radius, in particular to control the profile length (ARS) and the surface within the maximum effective radius of the surface. The proportional relationship (ARS/TP) between the thicknesses (TP) of the lens on the optical axis. For example, the length of the contour curve of the maximum effective radius of the side surface of the first lens object is represented by ARS11, and the thickness of the first lens on the optical axis is TP1, and the ratio between the two is ARS11/TP1, and the maximum effective radius of the side of the first lens image side. The length of the contour curve is represented by ARS12, and the ratio between it and TP1 is ARS12/TP1. The length of the contour curve of the maximum effective radius of the side of the second lens object is represented by ARS21, the thickness of the second lens on the optical axis is TP2, the ratio between the two is ARS21/TP2, and the contour of the maximum effective radius of the side of the second lens image The length of the curve is represented by ARS22, and the ratio between it and TP2 is ARS22/TP2. The proportional relationship between the length of the profile of the maximum effective radius of any surface of the remaining lenses in the optical imaging system and the thickness (TP) of the lens on the optical axis to which the surface belongs, and so on.

The optical image capturing system has a maximum image height HOI on the image plane vertical to the optical axis. A transverse aberration at 0.7 HOI in the positive direction of the tangential ray fan aberration after the longest operation wavelength passing through the edge of the entrance pupil is denoted by PLTA; a transverse aberration at 0.7 HOI in the positive direction of the tangential ray fan aberration after the shortest operation wavelength passing through the edge of the entrance pupil is denoted by PSTA; a transverse aberration at 0.7 HOI in the negative direction of the tangential ray fan aberration after the longest operation wavelength passing through the edge of the entrance pupil is denoted by NLTA; a transverse aberration at 0.7 HOI in the negative direction of the tangential ray fan aberration after the shortest operation wavelength passing through the edge of the entrance pupil is denoted by NSTA; a transverse aberration at 0.7 HOI of the sagittal ray fan aberration after the longest operation wavelength passing through the edge of the entrance pupil is denoted by SLTA; a transverse aberration at 0.7 HOI of the sagittal ray fan aberration after the shortest operation wavelength passing through the edge of the entrance pupil is denoted by SSTA.

For any surface of any lens, the profile curve length within a half the entrance pupil diameter (HEP) affects the ability of the surface to correct aberration and differences between optical paths of light in different fields of view. With longer profile curve length, the ability to correct aberration is better. However, the difficulty of manufacturing increases as well. Therefore, the profile curve length within a half the entrance pupil diameter (HEP) of any surface of any lens has to be controlled. The ratio between the profile curve length (ARE) within a half the entrance pupil diameter (HEP) of one surface and the thickness (TP) of the lens, which the surface belonged to, on the optical axis (i.e., ARE/TP) has to be particularly controlled. For example, the profile curve length of a half the entrance pupil diameter (HEP) of the object-side surface of the first lens is denoted by ARE11, the thickness of the first lens on the optical axis is TP1, and the ratio between these two parameters is ARE11/TP1; the profile curve length of a half the entrance pupil diameter (HEP) of the image-side surface of the first lens is denoted by ARE12, and the ratio between ARE12 and TP1 is ARE12/TP1. The profile curve length of a half the entrance pupil diameter (HEP) of the object-side surface of the second lens is denoted by ARE21, the thickness of the second lens on the optical axis is TP2, and the ratio between these two parameters is ARE21/TP2; the profile curve length of a half the entrance pupil diameter (HEP) of the image-side surface of the second lens is denoted by ARE22, and the ratio between ARE22 and TP2 is ARE22/TP2. For any surface of other lenses in the optical image capturing system, the ratio between the profile curve length of half the entrance pupil diameter (HEP) thereof and the thickness of the lens which the surface belonged to is denoted in the same manner.

With the movable carrier auxiliary system described above, the physiological state of the driver could be detected, and a corresponding detection signal could be generated to be sent to the warning device, so that the warning device could generate a corresponding warning signal for subsequent processing, improving driving safety. For instance, the warning device could generate a warning message when the warning device receives a detection signal that the physiological state of the driver is abnormal.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

A movable carrier auxiliary system of the present invention mainly includes a system design and an optical design, wherein system embodiments will be described first.

Figure 1A:
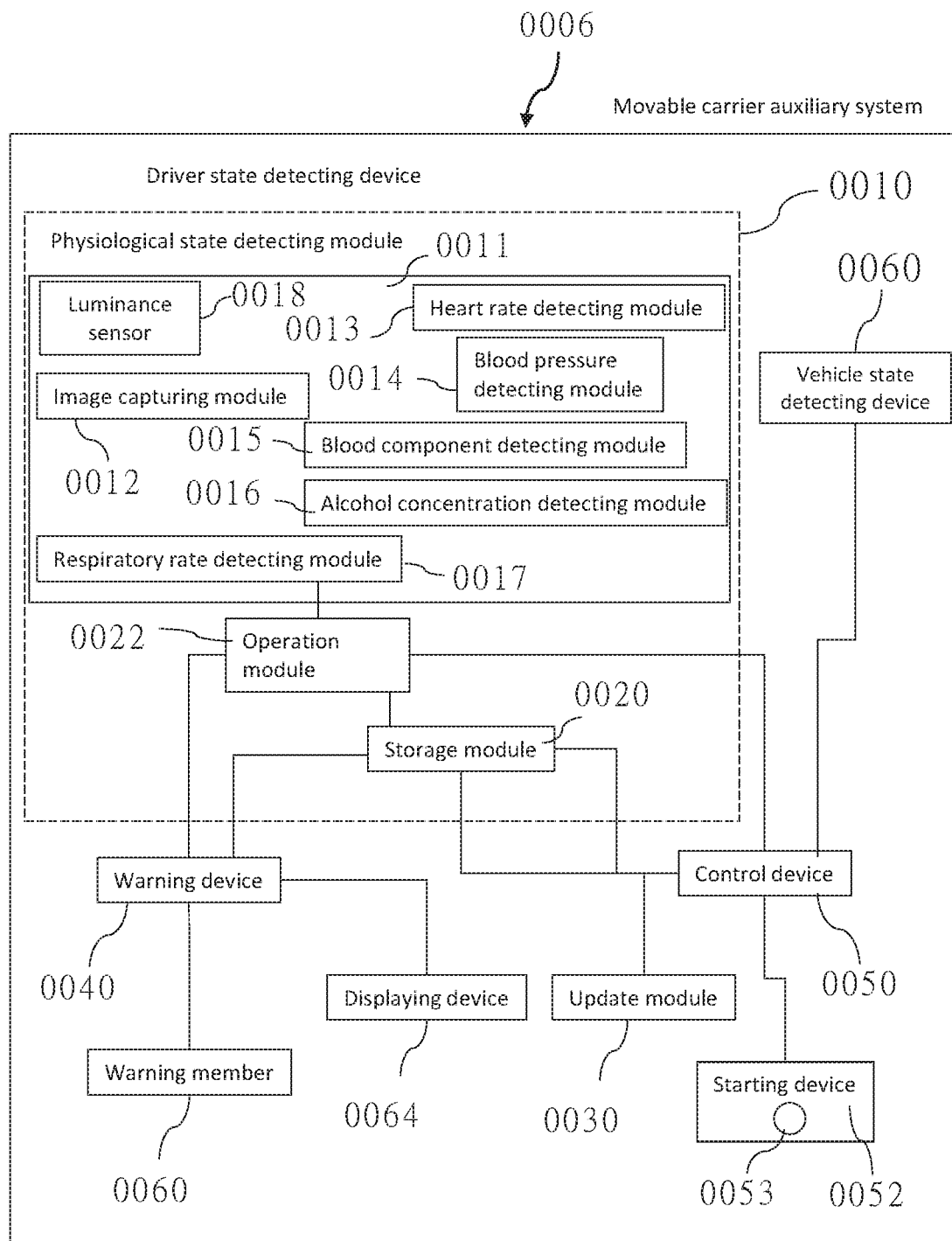
FIG. 1A is a block diagram showing a movable carrier auxiliary system according to a first system embodiment of the present invention.
Figure 1B:
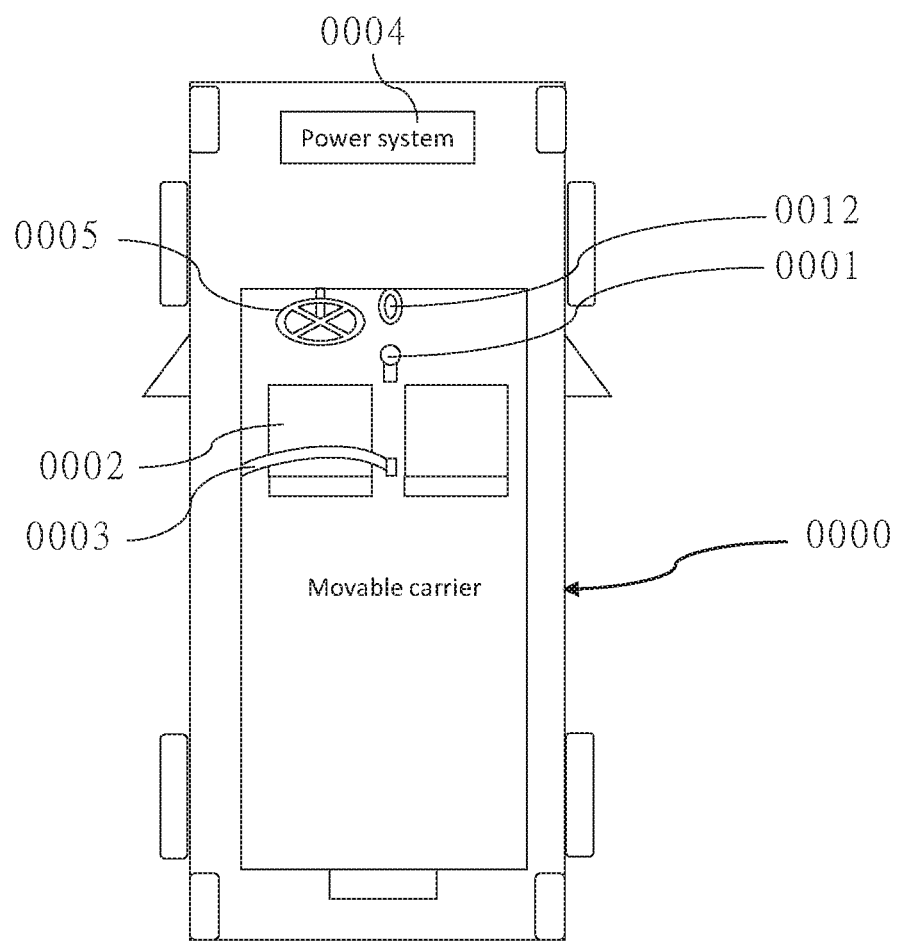
FIG. 1B is a schematic view showing the movable carrier auxiliary system is disposed on the movable carrier.

Take FIG. 1A and FIG. 1B as an example to illustrate a schematic view of a movable carrier auxiliary system 0006 according to a first system embodiment of the present invention applied to a movable carrier 0000 (e.g. a vehicle). In the current embodiment, the movable carrier auxiliary system 0006 at least includes a driver state detecting device 0010 and a warning device 0040, wherein the driver state detecting device 0010 includes a physiological state detecting module 0011, a storage module 0020, and an operation module 0022. The physiological state detecting module 0011 detects at least one physiological state of a driver who drives the movable carrier 0000. The storage module 0020 and the operation module 0022 are disposed in the movable carrier 0000. The storage module 0020 stores an allowable parameter corresponding to the at least one physiological state and at least two operating modes corresponding to whether the at least one physiological state of the driver exceeds the allowable parameter or not. The operation module 0022 is electrically connected to the physiological state detecting module 0011 and the storage module 0020 in a wired manner or a wireless manner and is adapted to determine whether the at least one physiological state of the driver exceeds the allowable parameter and to generate a detection signal correspondingly. In practice, the operation module 0022 could be a controller such as MCU, DSP, and etc.

In the current embodiment, the physiological state detecting module 0011 includes a plurality of modules, wherein the modules include an image capturing module 0012, a heart rate detecting module 0013, a blood pressure detecting module 0014, a blood component detecting module 0015, an alcohol concentration detecting module 0016, and a respiratory rate detecting module 0017. The storage module 0020 stores an allowable parameter corresponding to the at least one physiological state detected by each of the modules. In the current embodiment, the storage module 0020 could be electrically connected to an update module 0030, so that the allowable parameter stored in the storage module 0020 could be updated by the update module 0030.

The warning device 0040 is electrically connected to the operation module 0022 and the storage module 0020 and correspondingly generates a warning message based on the received detection signal. More specifically, the warning device 0040 generates the warning message for subsequent processing when a detection signal that the physiological state of the driver exceeds the allowable parameter is received.

In the current embodiment, the image capturing module 0012 is disposed in the movable carrier 0000 and is adapted to capture at least a driver image located on a driver seat 0002 in the movable carrier 0000. The image capturing module 0012 includes a lens group and an image sensing component, and the lens group includes at least two lenses having refractive power for imaging to the image sensing component to generate the driver image. The conditions of the lens group will be described in the optical embodiments.

In the current embodiment, the physiological state detecting module 0011 further includes a luminance sensor 0018 electrically connected to the image capturing module 0012 for detecting the luminance on at least the direction in which the image capturing module 0012 captures the image. When the luminance measured by the luminance sensor 0018 is greater than an upper threshold, the image capturing module 0012 captures the driver image in a way that reduces amount of light entering. When the luminance measured by the luminance sensor 0018 is less than a lower threshold, the image capturing module 0012 captures the driver image in a way that increases the amount of light entering. In this way, a driver image with appropriate luminance could be obtained, avoiding overexposure or underexposure.

In the current embodiment, the physiological state of the driver that the operation module 0022 analyzes based on the driver image is at least one of whether a direction of the driver's line of sight is toward a travel direction of the movable carrier 0000, a time that the driver's line of sight changes, a frequency that the driver's line of sight changes, a time that the driver's eyes close, a frequency that the driver's eyes blink, and etc. The operation module 0022 determines that whether the physiological state of the driver exceeds the allowable parameter and generates a corresponding detection signal to the warning device 0040.

The physiological state of the driver that the heart rate detecting module 0013 detects is heart rhythm or heart rate variation, and an allowable parameter corresponding to the heart rhythm or heart rate variation is stored in the storage module 0020. The operation module 0022 determines that whether the physiological state of the driver exceeds the allowable parameter based on a detecting result of the heart rate detecting module 0013, and correspondingly generates the detection signal. The warning device 0040 generates the warning message when the warning device 0040 receives a detection signal that one of the physiological states of the driver detected by the image capturing module 0012 and the heart rate detecting module 0013 exceeds the allowable parameter. In practice, the warning device 0040 generates the warning message when the warning device 0040 receives a detection signal that both of the physiological states of the driver detected by the image capturing module 0012 and the heart rate detecting module 0013 exceed the allowable parameter, achieving double confirmation, making determination more accurate.

The blood pressure detecting module 0014 is adapted to be touched by the driver, and the physiological state of the driver that the blood pressure detecting module 0014 detects is blood pressure or blood pressure variation. An allowable parameter corresponding to the blood pressure or blood pressure variation is stored in the storage module 0020. The operation module 0022 determines that whether the physiological state of the driver exceeds the allowable parameter based on a detecting result of the blood pressure detecting module 0014, and correspondingly generates the detection signal. The warning device 0040 generates the warning message when the warning device 0040 receives a detection signal that one of the physiological states of the driver detected by the image capturing module 0012 and the blood pressure detecting module 0014 exceeds the allowable parameter. In practice, the warning device 0040 generates the warning message when the warning device 0040 receives a detection signal that both of the physiological states of the driver detected by the image capturing module 0012 and the blood pressure detecting module 0014 exceed the allowable parameter, achieving double confirmation, making determination more accurate.

The physiological state of the driver that the blood component detecting module 0015 detects is alcohol concentration, blood oxygen concentration or blood glucose concentration in the blood, and an allowable parameter corresponding to the alcohol concentration, blood oxygen concentration or blood glucose concentration is stored in the storage module 0020. The operation module 0022 determines that whether the physiological state of the driver exceeds the allowable parameter based on a detecting result of the blood component detecting module 0015, and correspondingly generates the detection signal. The warning device 0040 generates the warning message when the warning device 0040 receives a detection signal that one of the physiological states of the driver detected by the image capturing module 0012 and the blood component detecting module 0015 exceeds the allowable parameter. In practice, the warning device 0040 generates the warning message when the warning device 0040 receives a detection signal that both of the physiological states of the driver detected by the image capturing module 0012 and the blood component detecting module 0015 exceed the allowable parameter, achieving double confirmation, making determination more accurate.

The physiological state of the driver that the alcohol concentration detecting module 0016 detects is alcohol concentration that the driver breathes out or alcohol concentration in blood, and an allowable parameter corresponding to the alcohol concentration is stored in the storage module 0020. The operation module 0022 determines that whether the physiological state of the driver exceeds the allowable parameter based on a detecting result of the alcohol concentration detecting module 0016, and correspondingly generates the detection signal. The warning device 0040 generates the warning message when the warning device 0040 receives a detection signal that the physiological state of the driver detected by the alcohol concentration detecting module 0016 exceeds the allowable parameter. In an embodiment, the alcohol concentration detecting module 0016 could be disposed on a gear shift device 0001 of the movable carrier 0000, so that the driver could manipulate the gear shift device 0001 to switch a travel state of the movable carrier 0000. When the driver manipulates the gear shift device 0001, the hand of the driver is in contact with the alcohol concentration detecting module 0016 on the gear shift device 0001.

Figure 1C:
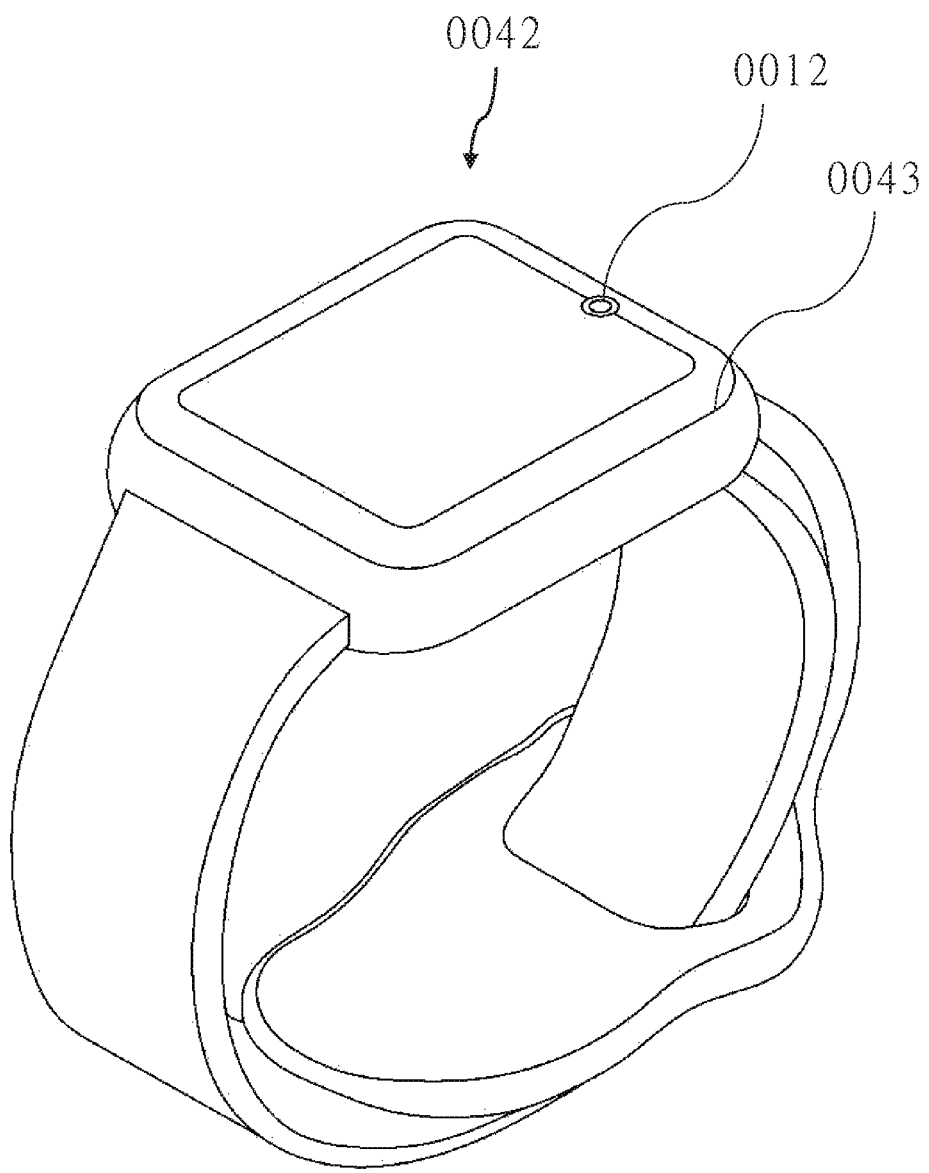
FIG. 1C is a schematic perspective view showing a wearable device according to the first system embodiment of the present invention.

In practice, the physiological state detecting module 0011 includes at least one of the aforementioned modules. In addition, at least one of the modules of the physiological state detecting module 0011 could be disposed on a wearable device 0042 of the driver (e.g. a watch as shown in FIG. 1C), so that the modules disposed on a wearable device 0042 could enter or leave the movable carrier 0000 along with the driver. In the current embodiment, the physiological state detecting module 0011 wirelessly sends a detecting result to the operation module 0022. For example, the image capturing module 0012 is disposed on a body 0043 of the wearable device 0042 for detecting outside of the body 0043, and the heart rate detecting module 0013, the blood pressure detecting module 0014, the blood component detecting module 0015, and the alcohol concentration detecting module 0016 could be also disposed on the body 0043.

The respiratory rate detecting module 0017 is adapted to detect a respiratory rate of the driver, and an allowable parameter corresponding to the respiratory rate is stored in the storage module 0020. The operation module 0022 determines that whether the physiological state of the driver exceeds the allowable parameter based on a detecting result of the respiratory rate detecting module 0017, and correspondingly generates the detection signal. For instance, the respiratory rate detecting module 0017 could be disposed on a seat back of the driver seat 0002 of the movable carrier 0000 corresponding to the back of the driver for detecting the move of the back of the driver when the driver breathes, or could be disposed on a safety belt 0003 for detecting the move of the chest of the driver when the driver breathes, wherein the operation module 0022 determines that the driver is tired or dozes off when the respiratory rate is lower than a predetermined rate. The warning device 0040 generates the warning message when the warning device 0040 receives a detection signal that one of the physiological states of the driver detected by the image capturing module 0012 and the respiratory rate detecting module 0017 exceeds the allowable parameter. In practice, the warning device 0040 generates the warning message when the warning device 0040 receives a detection signal that both of the physiological states of the driver detected by the image capturing module 0012 and the respiratory rate detecting module 0017 exceed the allowable parameter, achieving double confirmation, making determination more accurate.

In the current embodiment, the movable carrier auxiliary system 0006 further includes a control device 0050 and a starting device 0052, wherein the control device 0050 is disposed on the movable carrier 0000 and is electrically connected to the operation module 0022 and the storage module 0020. The control device 0050 correspondingly reads the operating mode from the storage module 0020 to control the movable carrier 0000 based on the received detection signal that whether the physiological state of the driver exceeds the allowable parameter or not.

The starting device 0052 is electrically connected to the control device 0050 in a wired manner or a wireless manner, so that the driver could manipulate the starting device 0052 to start or turn off a power system 0004 of the movable carrier 0000, wherein the power system 0004 could be an engine of a gasoline-powered vehicle or a motor of an electric vehicle. The starting device 0052 work in coordination with the control device 0050 to properly control the movable carrier 0000. When the movable carrier 0000 is in a state that the power system 0004 is turned off and the driver is about to start the power system 0004 via the starting device 0052, the control device 0050 controls the movable carrier 0000 in different ways depending on different physiological states of the driver. More specifically, when the control device 0050 receives a detection signal that the physiological state of the driver does not exceed the allowable parameter, the control device 0050 controls the movable carrier 0000 in an operating mode that allows the movable carrier 0000 to be started by the power system 0004, so that the driver could drive the movable carrier 0000. On the other hand, when the control device 0050 receives a detection signal that at least one of the physiological states of the driver exceeds the allowable parameter, the control device 0050 inhibits the power system 0004 from controlling the movable carrier 0000 in the operating mode that starts the movable carrier 0000, preventing the driver from unsuitably driving and dangerous driving.

For instance, in order to prevent the driver from drunk driving, when the movable carrier 0000 is in a state that the power system 0004 is turned off and the driver is about to start the power system 0004 via the starting device 0052 and the control device 0050 receives a detection signal that the physiological state of the driver detected by the alcohol concentration detecting module 0016 does not exceed the allowable parameter, the control device 0050 controls the movable carrier 0000 in the operating mode that allows the movable carrier 0000 to be started by the power system 0004, so that the driver could drive the movable carrier 0000. On the other hand, when the control device 0050 receives a detection signal that the physiological state of the driver detected by the alcohol concentration detecting module 0016 exceeds the allowable parameter, the control device 0050 controls the movable carrier 0000 in an operating mode that disallows the movable carrier 0000 to be started by the power system 0004, preventing the driver from driving the movable carrier 0000.

In the current embodiment, the starting device 0052 is disposed in the movable carrier 0000 (e.g. near the driver seat 0002) and has a starting button 0053 which is adapted to be pressed by the driver to operate the starting device 0052 to start or turn off the power system 0004. At least one of the modules of the physiological state detecting module 0011 is disposed on the starting button 0053. The alcohol concentration detecting module 0016 is disposed on the starting device 0052. Preferably, the alcohol concentration detecting module 0016 is disposed on the starting button 0053, so that the finger of the driver could touch the alcohol concentration detecting module 0016 at the same time when the driver presses the starting button 0053. Then, the alcohol concentration detecting module 0016 sends the detecting result to the operation module 0022 in a wired manner or a wireless manner. In an embodiment, the heart rate detecting module 0013 could be disposed on the starting button 0053, so that the finger of the driver could touch the heart rate detecting module 0013 at the same time when the driver presses the starting button 0053. Then, the heart rate detecting module 0013 sends the detected physiological state (e.g. heart rhythm or heart rate variation) of the driver to the operation module 0022 in a wired manner or a wireless manner.

In practice, the starting device 0052 could be a remote control, and at least one of the modules of the physiological state detecting module 0011 could be disposed on the remote control. For instance, the heart rate detecting module 0013 could be disposed on the remote control, so that the hand of the driver could touch the heart rate detecting module 0013 at the same time when the driver takes the remote control. Then, the heart rate detecting module 0013 sends the detected physiological state (e.g. heart rhythm or heart rate variation) of the driver to the operation module 0022 in a wired manner or a wireless manner.

In order to prevent a dangerous driving situation that the driver is discomfort when the movable carrier 0000 is in a state that the power system 0004 starts, when the control device 0050 receives the detection signal that at least one of the physiological state of the driver exceeds the allowable parameter for a predetermined time, the control device 0050 controls the movable carrier 0000 in an operating mode that the movable carrier 0000 is automatically driven to replace the human driving.

Different controls could be carried out depending on different movement states of the movable carrier 0000 when driving from human to automatic driving. The movable carrier auxiliary system 0006 further includes a vehicle state detecting device 0060 disposed on the movable carrier 0000 and electrically connected to the control device 0050 for detecting a movement state of the movable carrier 0000 and generating a state signal. In practice, the vehicle state detecting device 0060 could include at least one of a steering angle sensor, an inertia measuring device, and a speed sensor, wherein the steering angle sensor detects a steering angle of the movable carrier 0000; the inertia measuring device is adapted to detect an acceleration, an inclined angle, or a yaw rate of the movable carrier 0000; the speed sensor is adapted to detect a speed of the movable carrier 0000. The vehicle state detecting device 0060 correspondingly outputs the state signal based on a detecting result of at least one of the speed sensor, the inertia measuring device, and the steering angle sensor.

The control device 0050 controls the movable carrier 0000 to automatic driving based on the state signal. For instance, the control device 0050 correspondingly controls the movable carrier 0000 based on the operating mode of automatic driving and the state signal of a current moving speed, preventing the person in the movable carrier 0000 feels uncomfortable due to the operating mode switches.

In order to prompt the driver, the movable carrier auxiliary system 0006 further includes a warning member 0062 electrically connected to the warning device 0040 and a displaying device 0064, wherein the warning member 0062 is adapted to receive the warning message and to correspondingly generate light, sound, vibration, or physical touch when the warning device 0040 sends the warning message. The warning member 0062 includes a buzzer or/and a light emitting diode (LED), which can be respectively disposed at the left and right sides of the movable carrier 0000 (e.g. an inner or outer area near the driver seat of the movable carrier 0000, such as the front pillar, the left/right rear-view mirror, the fascia, the front windshield, etc.), so as to operate corresponding to the detection results of the movable carrier 0000. The warning member 0062 could be a vibrator or a seatbelt tensioner, wherein the vibrator could be disposed on the driver seat 0002, a steering wheel 0005, or on a seatbelt 0003 of the movable carrier 0000 for generating vibration or physical touch to the driver. The seatbelt tensioner is connected to the seatbelt 0003 for tensioning the seatbelt 0003 to generate physical touch to the driver.

The displaying device 0064 is adapted to display the warning message. For example, the warning message could be displayed on the displaying device 0024 as an image, a text, or both of the image and the text. At least one of the warning member 0062 and the displaying device 0064 prompts the driver that the physiological state of the driver is unsuitable for driving the movable carrier 0000.

Figure 1D:
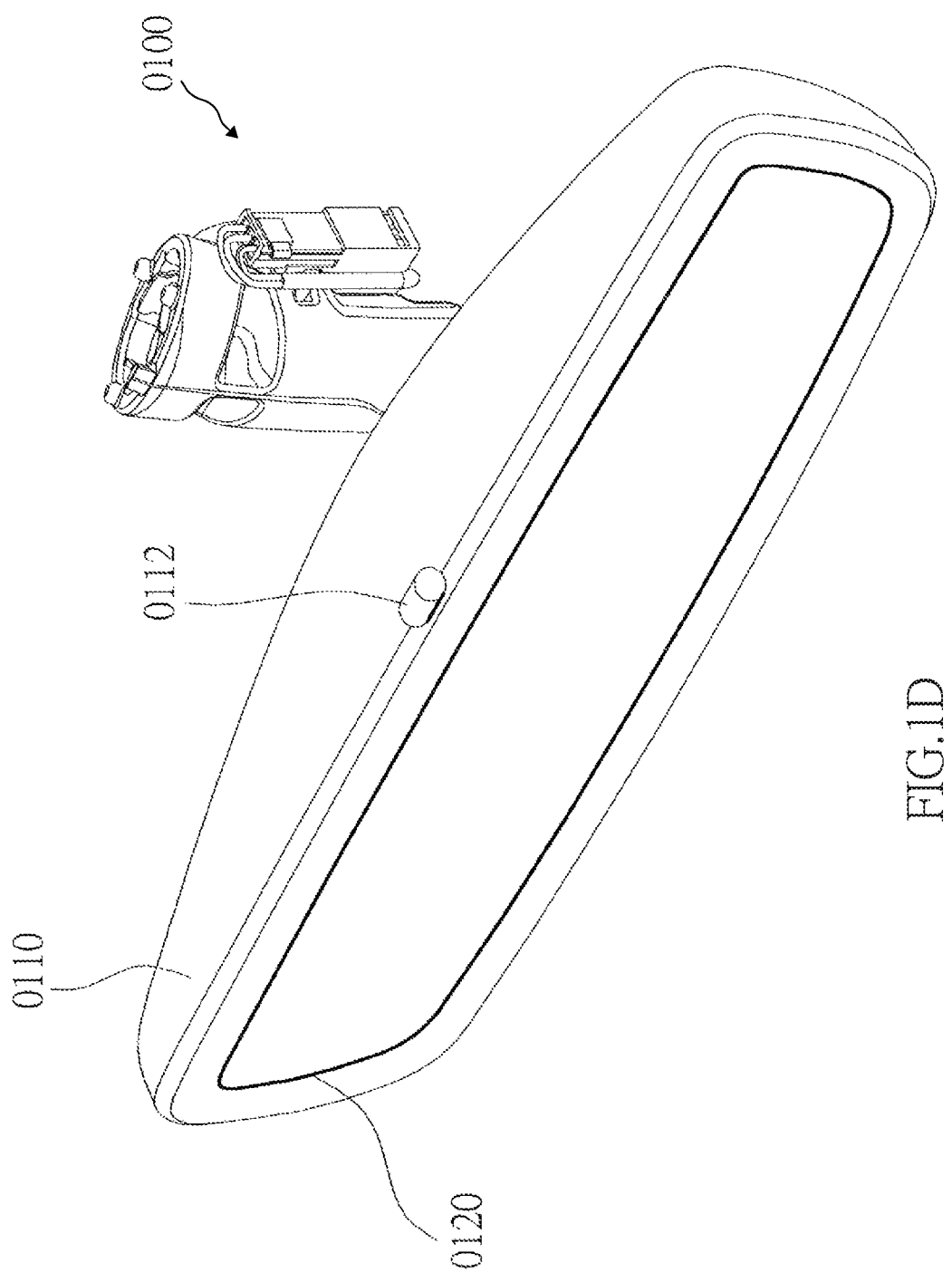
FIG. 1D is a schematic perspective view showing a vehicle electronic rear-view mirror according to the first system embodiment of the present invention.
Figure 1E:
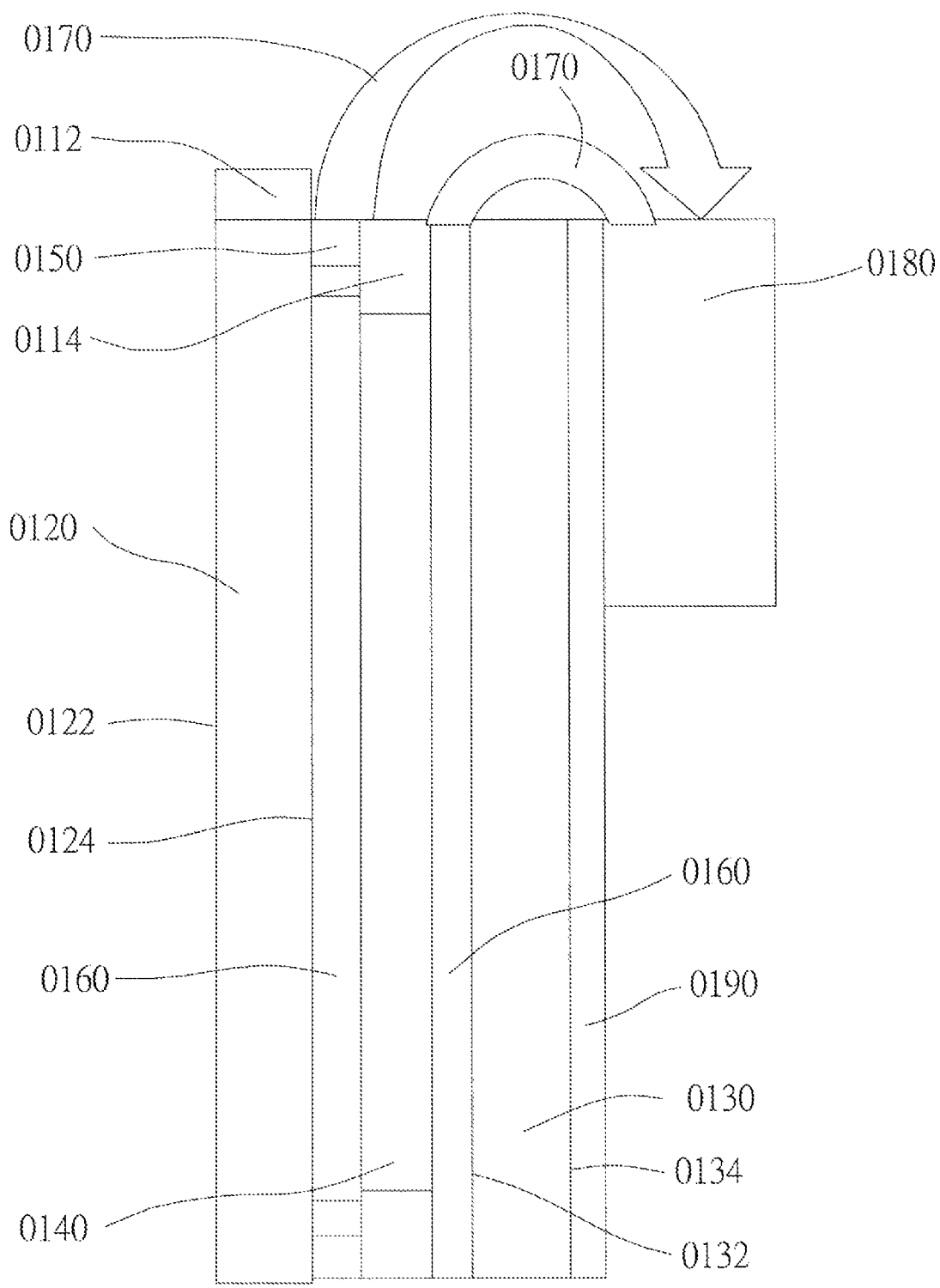
FIG. 1E is a schematic section view taken along the short side of the displaying device according to the first system embodiment of the present invention.

FIG. 1D is a schematic perspective view showing the displaying device 0064 according to the first system embodiment of the present invention, in which the displaying device 0064 is a vehicle electronic rear-view mirror 0100 having a display (not shown), for example. FIG. 1E is a schematic section view taken along the short side of the displaying device of FIG. 1D. The vehicle electronic rear-view mirror 0100 could be disposed on a movable carrier, e.g. a vehicle, to assist in the driving of the vehicle or to provide information about driving. More specifically, the vehicle electronic rear-view mirror 0100 could be an inner rear-view mirror disposed inside the vehicle or an outer rear-view mirror disposed outside the vehicle, both of which are used to assist the driver in understanding the location of other vehicles. However, this is not a limitation on the present invention. In addition, the movable carrier is not limited to the vehicle, and could be other types of transportation, such as a land train, an aircraft, a water ship, etc.

The vehicle electronic rear-view mirror 0100 is assembled in a casing 0110, wherein the casing 0110 has an opening (not shown). More specifically, the opening of the casing 0110 overlaps with a reflective layer 0190 of the vehicle electronic rear-view mirror 0100 (as shown in FIG. 1D). In this way, external light could be transmitted to the reflective layer 0190 located inside the casing 0110 through the opening, so that the vehicle electronic rear-view mirror 0100 functions as a mirror. When the driver drives the vehicle and faces the opening, for example, the driver could perceive the external light reflected by the vehicle electronic rear-view mirror 0100, thereby knowing the position of the rear vehicle.

Referring to FIG. 1E, the vehicle electronic rear-view mirror 0100 includes a first transparent assembly 0120 and a second transparent assembly 0130, wherein the first transparent assembly 0120 faces the driver, and the second transparent assembly 0130 is disposed on a side away from the driver. More specifically, the first transparent assembly 0120 and the second transparent assembly 0130 are translucent substrates, wherein a material of the translucent substrates could be glass, for example. However, the material of the translucent substrates is not a limitation on the present invention. In other embodiments, the material of the translucent substrates could be plastic, quartz, PET substrate, or other applicable materials, wherein the PET substrate has the advantages of low cost, easy manufacture, and extremely thinness, in addition to the packaging and protection effects.

In this embodiment, the first transparent assembly 0120 includes a first incidence surface 0122 and a first exit surface 0124, wherein an incoming light image from the rear of the driver enters the first transparent assembly 0120 via the first incidence surface 0122, and is emitted via the first exit surface 0124. The second transparent assembly 0130 includes a second incidence surface 0132 and a second exit surface 0134, wherein the second incidence surface 0132 faces the first exit surface 0124, and a gap is formed between the second incidence surface 0132 and the first exit surface 0124 by an adhesive 0114. After being emitted via the first exit surface 0124, the incoming light image enters the second transparent assembly 0130 via the second incidence surface 0132 and emitted via the second exit surface 0134.

An electro-optic medium layer 0140 is disposed in the gap between the first exit surface 0124 of the first transparent assembly 0120 and the second incidence surface 0132 of the second transparent assembly 0130. At least one transparent electrode 0150 is disposed between the first transparent assembly 0120 and the electro-optic medium layer 0140. The electro-optic medium layer 0140 is disposed between the first transparent assembly 0120 and at least one reflective layer 0190. A transparent conductive layer 0160 is disposed between the first transparent assembly 0120 and the electro-optic medium layer 0140. Another transparent conductive layer 0160 is disposed between the second transparent assembly 0130 and the electro-optic medium layer 0140. An electrical connector 0170 is electrically connected to the transparent conductive layer 0160, and another electrical connector 0170 is electrically connected to the transparent electrode 0150, which is electrically connected to the electro-optic medium layer 0140 directly or indirectly through the another transparent conductive layer 0160, thereby transmitting electrical energy to the electro-optic medium layer 0140 to change a transparency of the electro-optic medium layer 0140. When a luminance of the incoming light image exceeds a certain luminance (e.g. strong light from the headlight of the rear vehicle), a glare sensor 0112 electrically connected to a control member 0180 receives the light energy and convert it into a signal, and the control member 0180 determines whether the luminance of the incoming light image exceeds a predetermined luminance, and if a glare is generated, the electrical energy is provided to the electro-optic medium layer 0140 by the electrical connector 0170 to generate an anti-glare performance Generally, if the incoming light image has a strong luminance, the glare could be generated and thus affects the driver's line of sight, thereby endangering the driving safety.

In addition, the transparent electrode 0150 and the reflective layer 0190 could respectively cover the entire surfaces of the first transparent assembly 0120 and the second transparent assembly 0130. However, this is not a limitation on the present invention. In this embodiment, the transparent electrode 0150 could use a material selected from metal oxides, such as indium tin oxide, indium zinc oxide, aluminum tin oxide, aluminum zinc oxide, indium antimony zinc oxide, or other suitable oxides, or a stacked layer composed of at least two of the foregoing oxides. Moreover, the reflective layer 0190 could be conductive and made of a material selected from the group consisting of silver (Ag), copper (Cu), aluminum (Al), titanium (Ti), chromium (Cr), molybdenum (Mo), and an alloy thereof, or contains silicon dioxide or a transparent conductive material. However, the material of the transparent electrode 0150 and the material of the reflective layer 0190 are not limitations on the present invention. In other embodiments, the material of the transparent electrode 0150 and the material of the reflective layer 0190 could be other types of materials.

The electro-optic medium layer 0140 could be made of an organic material or an inorganic material. However, this is not a limitation on the present invention. In the current embodiment, the electro-optic medium layer 0140 could be an electrochromic material. The electro-optic medium layer 0140 is disposed between the first transparent assembly 0120 and the second transparent assembly 0130 and also disposed between the first transparent assembly 0120 and the reflective layer 0190. More specifically, the transparent electrode 0150 is disposed between the first transparent assembly 0120 and the electro-optic medium layer 0140 (i.e., the electrochromic material layer). In an embodiment, the reflective layer 0190 could be disposed between the second transparent assembly 0130 and the electro-optic medium layer 0140. In addition, in the current embodiment, the vehicle electronic rear-view mirror 0100 further includes an adhesive 0114 located between the first transparent assembly 0120 and the second transparent assembly 0130 and surrounding the electro-optic medium layer 0140. The electro-optic medium layer 0140 is co-packaged by the adhesive 0114, the first transparent assembly 0120, and the second transparent assembly 0130.

In the current embodiment, the transparent conductive layer 0160 is disposed between the electro-optic medium layer 0140 and the reflective layer 0190. More specifically, the transparent conductive layer 0160 could be used as an anti-oxidation layer of the reflective layer 0190, so that the electro-optic medium layer 0140 could be prevented from direct contact with the reflective layer 0190, thereby preventing the reflective layer 0190 from being corroded by the organic materials, and extending the service life of the vehicle electronic rear-view mirror 0100 of the current embodiment. In addition, the electro-optic medium layer 0140 is co-packaged by the adhesive 0114, the transparent electrode 0150, and the transparent conductive layer 0160. In the current embodiment, the transparent conductive layer 0160 contains a material selected from the group consisting of indium tin oxide (ITO), indium zinc oxide (IZO), Al-doped ZnO (AZO), fluorine-doped tin oxide, and a combination thereof.

In the current embodiment, the vehicle electronic rear-view mirror 0100 could be optionally provided with the electrical connector 0170. For instance, in an embodiment, the electrical connector 0170 could be a conducting wire or a conducting structure electrically connected to the transparent electrode 0150 and the reflective layer 0190, so that the transparent electrode 0150 and the reflective layer 0190 could be electrically connected to the at least one control member 0180, which provides a driving signal via the conducting wire or the conducting structure, thereby driving the electro-optic medium layer 0140.

When the electro-optic medium layer 0140 is enabled, the electro-optic medium layer 0140 would undergo an electrochemical redox reaction and change its energy level to be in a diming state. When external light passes through the opening of the casing 0110 and reaches the electro-optic medium layer 0140, the external light would be absorbed by the electro-optic medium layer 0140 which is in the diming state, so that the vehicle electronic rear-view mirror 0100 is switched to an anti-glare mode. On the other hand, when the electro-optic medium layer 0140 is disenabled, the electro-optic medium layer 0140 is transparent. At this time, the external light passing through the opening of the casing 0110 passes through the electro-optic medium layer 0140 to be reflected by the reflective layer 0190, so that the vehicle electronic rear-view mirror 0100 is switched to a mirror mode.

More specifically, the first transparent assembly 0120 has the first incidence surface 0122 which is away from the second transparent assembly 0130. For instance, external light from the rear vehicles enters the vehicle electronic rear-view mirror 0100 via the first incidence surface 0122, and then the vehicle electronic rear-view mirror 0100 reflects the external light such that the external light leaves the vehicle electronic rear-view mirror 0100 via the first incidence surface 0122. In addition, eyes of the vehicle driver could receive the external light reflected by the vehicle electronic rear-view mirror 0100 to know the position of other vehicles behind. Moreover, the reflective layer 0190 could have the optical property of partial transmission and partial reflection by selecting a suitable material and designing a proper film thickness.

The display of the vehicle electronic rear-view mirror 0100 could be an LCD or an LED, and the display could be disposed inside or outside the casing 0110, for example, on the side of the second transparent assembly 0130 away from the first transparent assembly 0120, or on the second exit surface 0134 of the second transparent assembly 0130 away from the first transparent assembly 0120. Since the reflective layer 0190 has the optical property of partial transmission and partial reflection, the image light emitted by the display could pass through the reflective layer 0190, thereby allowing the user to view the internal image displayed by the display so as to display the warning message.

The warning message could store at least one emergency contact information in advance in the storage module 0020 in addition to prompt the driver. When the warning device 0040 generates the warning message, the warning message is sent to the emergency contact information. For instance, the warning device 0040 has a communicating module, wherein the communicating module is capable of being connected to telecommunications network or internet and sending the warning message to the electronic device (e.g. a cell phone, a computer, and etc.) corresponding to the emergency contact information, thereby to prompt the emergency contact person that the physiological state of the driver is unsuitable for driving the movable carrier 0000.

With the movable carrier auxiliary system 0006 according to the first system embodiment of the present invention, the physiological state detecting module 0011 could detect the physiological state of the driver and correspondingly generate the detection signal to the warning device 0040, so that the warning device 0040 generates the warning message for subsequent processing based on the received detection signal that the at least one physiological state of the driver exceeds the allowable parameter (i.e., when a detection signal that the physiological state of the driver is abnormal is received).

Furthermore, the optical embodiments will be described in detail as follows. The optical image capturing system could work with three wavelengths, including 486.1 nm, 587.5 nm, and 656.2 nm, wherein 587.5 nm is the main reference wavelength and is also the reference wavelength for extracting the technical characteristics. The optical image capturing system could also work with five wavelengths, including 470 nm, 510 nm, 555 nm, 610 nm, and 650 nm, wherein 555 nm is the main reference wavelength and is also the reference wavelength for extracting the technical characteristics.

The optical image capturing system of the present invention satisfies $0.5 \leq \Sigma PPR/|\Sigma NPR| \leq 15$, and preferably satisfies $1 \leq \Sigma PPR/|\Sigma NPR| \leq 3.0$, where PPR is a ratio of the focal length f of the optical image capturing system to a focal length fp of each of the lenses with positive refractive power; NPR is a ratio of the focal length f of the optical image capturing system to a focal length fn of each of the lenses with negative refractive power; $\Sigma PPR$ is a sum of the PPRs of each positive lens; and $\Sigma NPR$ is a sum of the NPRs of each negative lens. It is helpful for control of an entire refractive power and an entire length of the optical image capturing system.

The optical image capturing system further includes an image sensor provided on the image plane. The optical image capturing system of the present invention satisfies $HOS/HOI \leq 50$ and $0.5 \leq HOS/f \leq 150$, and preferably satisfies $1 \leq HOS/HOI \leq 40$ and $1 \leq HOS/f \leq 140$, where HOI is half a length of a diagonal of an effective sensing area of the image sensor, i.e., the maximum image height, and HOS is a distance in parallel with the optical axis between an object-side surface of the first lens and the image plane of the at least one lens group. It is helpful for the miniaturization of the optical image capturing system and the application in light, thin, and portable electronic products.

The optical image capturing system of the present invention is further provided with an aperture to increase image quality.

In the optical image capturing system of the present invention, the aperture could be a front aperture or a middle aperture, wherein the front aperture is provided between the object and the first lens, and the middle aperture is provided between the first lens and the image plane. The front aperture provides a relatively long distance between an exit pupil of the optical image capturing system and the image plane, which allows more optical elements to be installed and increases the image receiving efficiency of the image sensor. The middle aperture could enlarge the view angle of the optical image capturing system, which provides the advantage of a wide-angle lens. The optical image capturing system satisfies $0.1 \leq InS/HOS \leq 1.1$, where InS is a distance on the optical axis between the aperture and an image plane of the at least one lens group. It is helpful for size reduction and wide angle.

The optical image capturing system of the present invention satisfies $0.1 \leq TP/InTL \leq 0.9$, where InTL is a distance in parallel with the optical axis from the object-side surface of the first lens to an image-side surface of the sixth lens, and $\Sigma TP$ is a sum of central thicknesses of the lenses having refractive power on the optical axis. It is helpful for the contrast of image and yield rate of lens manufacturing, and also provides a suitable back focal length for installation of other elements.

The optical image capturing system of the present invention satisfies $0.001 \leq |R1/R2| \leq 25$, and preferably satisfies $0.01 \leq |R1/R2| \leq 12$, where R1 is a radius of curvature of the object-side surface of the first lens, and R2 is a radius of curvature of the image-side surface of the first lens. It provides the first lens with a suitable positive refractive power to reduce the increase rate of the spherical aberration.

The optical image capturing system of the present invention satisfies $-7 \leq (R11-R12)/(R11+R12) \leq 50$, where R11 is a radius of curvature of the object-side surface of the sixth lens, and R12 is a radius of curvature of the image-side surface of the sixth lens. It may modify the astigmatic field curvature.

The optical image capturing system of the present invention satisfies $IN12/f \leq 60$, where IN12 is a distance on the optical axis between the first lens and the second lens. It may correct chromatic aberration and improve the performance.

The optical image capturing system of the present invention satisfies $IN56/f \leq 3.0$, where IN56 is a distance on the optical axis between the fifth lens and the sixth lens. It may correct chromatic aberration and improve the performance.

The optical image capturing system of the present invention satisfies 0.1≤(TP1+IN12)/TP2≤10, where TP1 is a central thickness of the first lens on the optical axis, and TP2 is a central thickness of the second lens on the optical axis. It may control the sensitivity of manufacture of the optical image capturing system and improve the performance.

The optical image capturing system of the present invention satisfies 0.1≤(TP6+IN56)/TP5≤15, where TP5 is a central thickness of the fifth lens on the optical axis, TP6 is a central thickness of the sixth lens on the optical axis, and IN56 is a distance between the fifth lens and the sixth lens. It may control the sensitivity of manufacture of the optical image capturing system and improve the performance.

The optical image capturing system of the present invention satisfies 0.1≤TP4/(IN34+TP4+IN45)≤1, where TP2 is a central thickness of the second lens on the optical axis, TP3 is a central thickness of the third lens on the optical axis, TP4 is a central thickness of the fourth lens on the optical axis, IN34 is a distance on the optical axis between the third lens and the fourth lens, and IN45 is a distance on the optical axis between the fourth lens and the fifth lens. It may fine-tune and correct the aberration of the incident rays layer by layer, and reduce the overall height of the optical image capturing system.

The optical image capturing system satisfies 0 mm≤HVT61≤3 mm; 0 mm HVT62≤6 mm; 0≤HVT61/HVT62; 0 mm≤|SGC61|≤0.5 mm; 0 mm≤|SGC62|≤2 mm; and 0≤|SGC62|/(|SGC62|+TP6)≤0.9, where HVT61 is a vertical distance from the critical point C61 on the object-side surface of the sixth lens to the optical axis; HVT62 is a vertical distance from the critical point C62 on the image-side surface of the sixth lens to the optical axis; SGC61 is a distance on the optical axis between a point on the object-side surface of the sixth lens where the optical axis passes through and a point where the critical point C61 projects on the optical axis; SGC62 is a distance on the optical axis between a point on the image-side surface of the sixth lens where the optical axis passes through and a point where the critical point C62 projects on the optical axis. It is helpful to correct the off-axis view field aberration.

The optical image capturing system satisfies 0.2≤HVT62/HOI≤0.9, and preferably satisfies 0.3≤HVT62/HOI≤0.8. It may help to correct the peripheral aberration.

The optical image capturing system satisfies 0≤HVT62/HOS≤0.5, and preferably satisfies 0.2≤HVT62/HOS≤0.45. It may help to correct the peripheral aberration.

The optical image capturing system of the present invention satisfies 0≤SGI611/(SGI611+TP6)≤0.9; 0≤SGI621/(SGI621+TP6)≤0.9, and preferably satisfies 0.1≤SGI611/(SGI611+TP6)≤0.6; 0.1≤SGI621/(SGI621+TP7)≤0.6, where SGI611 is a displacement on the optical axis from a point on the object-side surface of the sixth lens, through which the optical axis passes, to a point where the inflection point on the object-side surface of the sixth lens, which is the closest to the optical axis, projects on the optical axis, and SGI621 is a displacement on the optical axis from a point on the image-side surface of the sixth lens, through which the optical axis passes, to a point where the inflection point on the image-side surface of the sixth lens, which is the closest to the optical axis, projects on the optical axis.

The optical image capturing system of the present invention satisfies 0≤SGI612/(SGI612+TP6)≤0.9; 0≤SGI622/(SGI622+TP6)≤0.9, and it is preferable to satisfy 0.1≤SGI612/(SGI612+TP6)≤0.6; 0.1≤SGI622/(SGI622+TP6)≤0.6, where SGI612 is a displacement on the optical axis from a point on the object-side surface of the sixth lens, through which the optical axis passes, to a point where the inflection point on the object-side surface, which is the second closest to the optical axis, projects on the optical axis, and SGI622 is a displacement on the optical axis from a point on the image-side surface of the sixth lens, through which the optical axis passes, to a point where the inflection point on the object-side surface, which is the second closest to the optical axis, projects on the optical axis.

The optical image capturing system of the present invention satisfies 0.001 mm≤|HIF611|≤5 mm; 0.001 mm≤|HIF621|≤5 mm, and it is preferable to satisfy 0.1 mm≤|HIF611|≤3.5 mm; 1.5 mm≤|HIF621|≤3.5 mm, where HIF611 is a vertical distance from the inflection point closest to the optical axis on the object-side surface of the sixth lens to the optical axis; HIF621 is a vertical distance from the inflection point closest to the optical axis on the image-side surface of the sixth lens to the optical axis.

The optical image capturing system of the present invention satisfies 0.001 mm≤|HIF612|≤5 mm; 0.001 mm≤|HIF622|≤5 mm, and it is preferable to satisfy 0.1 mm≤|HIF622|≤3.5 mm; 0.1 mm≤|HIF612|≤3.5 mm, where HIF612 is a vertical distance from the inflection point second closest to the optical axis on the object-side surface of the sixth lens to the optical axis; HIF622 is a vertical distance from the inflection point second closest to the optical axis on the image-side surface of the sixth lens to the optical axis.

The optical image capturing system of the present invention satisfies 0.001 mm≤|HIF613|≤5 mm; 0.001 mm≤|HIF623|≤5 mm, and it is preferable to satisfy 0.1 mm≤|HIF623|≤3.5 mm; 0.1 mm≤|HIF613|≤3.5 mm, where HIF613 is a vertical distance from the inflection point third closest to the optical axis on the object-side surface of the sixth lens to the optical axis; HIF623 is a vertical distance from the inflection point third closest to the optical axis on the image-side surface of the sixth lens to the optical axis.

The optical image capturing system of the present invention satisfies 0.001 mm≤|HIF614|≤5 mm; 0.001 mm≤|HIF624|≤5 mm, and it is preferable to satisfy 0.1 mm≤|HIF624|≤3.5 mm; 0.1 mm≤|HIF614|≤3.5 mm, where HIF614 is a vertical distance from the inflection point fourth closest to the optical axis on the object-side surface of the sixth lens to the optical axis; HIF624 is a vertical distance from the inflection point fourth closest to the optical axis on the image-side surface of the sixth lens to the optical axis.

In an embodiment, the lenses of high Abbe number and the lenses of low Abbe number are arranged in an interlaced arrangement that could be helpful for correction of aberration of the optical image capturing system.

An equation of aspheric surface is $$z = ch^2/[1+[1(k+1)c^2h^2]^{0.5}] + A4h^4 + A6h^6 + A8h^8 + A10h^{10} + A12h^{12} + A14h^{14} + A16h^{16} + A18h^{18} + A20h^{20} + \ldots \quad (1)$$

where z is a depression of the aspheric surface; k is conic constant; c is reciprocal of the radius of curvature; and A4, A6, A8, A10, A12, A14, A16, A18, and A20 are high-order aspheric coefficients.

In the optical image capturing system, the lenses could be made of plastic or glass. The plastic lenses may reduce the weight and lower the cost of the optical image capturing system, and the glass lenses may control the thermal effect and enlarge the space for arrangement of the refractive power of the optical image capturing system. In addition, the opposite surfaces (object-side surface and image-side surface) of the first to the seventh lenses could be aspheric that could obtain more control parameters to reduce aberration. The number of aspheric glass lenses could be less than the conventional spherical glass lenses, which is helpful for reduction of the height of the optical image capturing system.

Furthermore, in the optical image capturing system provided by the present invention, when the lens has a convex surface, it means that the surface of the lens around the optical axis is convex, and when the lens has a concave surface, it means that the surface of the lens around the optical axis is concave.

The optical image capturing system of the present invention could be applied in a dynamic focusing optical image capturing system. It is superior in the correction of aberration and high imaging quality so that it could be allied in lots of fields.

The optical image capturing system of the present invention could further include a driving module to meet different demands, wherein the driving module could be coupled with the lenses to move the lenses. The driving module could be a voice coil motor (VCM), which is used to move the lens for focusing, or could be an optical image stabilization (OIS) component, which is used to lower the possibility of having the problem of image blurring which is caused by subtle movements of the lens while shooting.

To meet different requirements, at least one lens among the first lens to the seventh lens of the optical image capturing system of the present invention could be a light filter, which filters out light of wavelength shorter than 500 nm. Such effect could be achieved by coating on at least one surface of the lens, or by using materials capable of filtering out short waves to make the lens.

To meet different requirements, the image plane of the optical image capturing system in the present invention could be either flat or curved. If the image plane is curved (e.g., a sphere with a radius of curvature), the incidence angle required for focusing light on the image plane could be decreased, which is not only helpful to shorten the length of the optical image capturing system (TTL), but also helpful to increase the relative illuminance.

We provide several optical embodiments in conjunction with the accompanying drawings for the best understanding. In practice, the optical embodiments of the present invention could be applied to other embodiments.

First Optical Embodiment

Figure 2A:
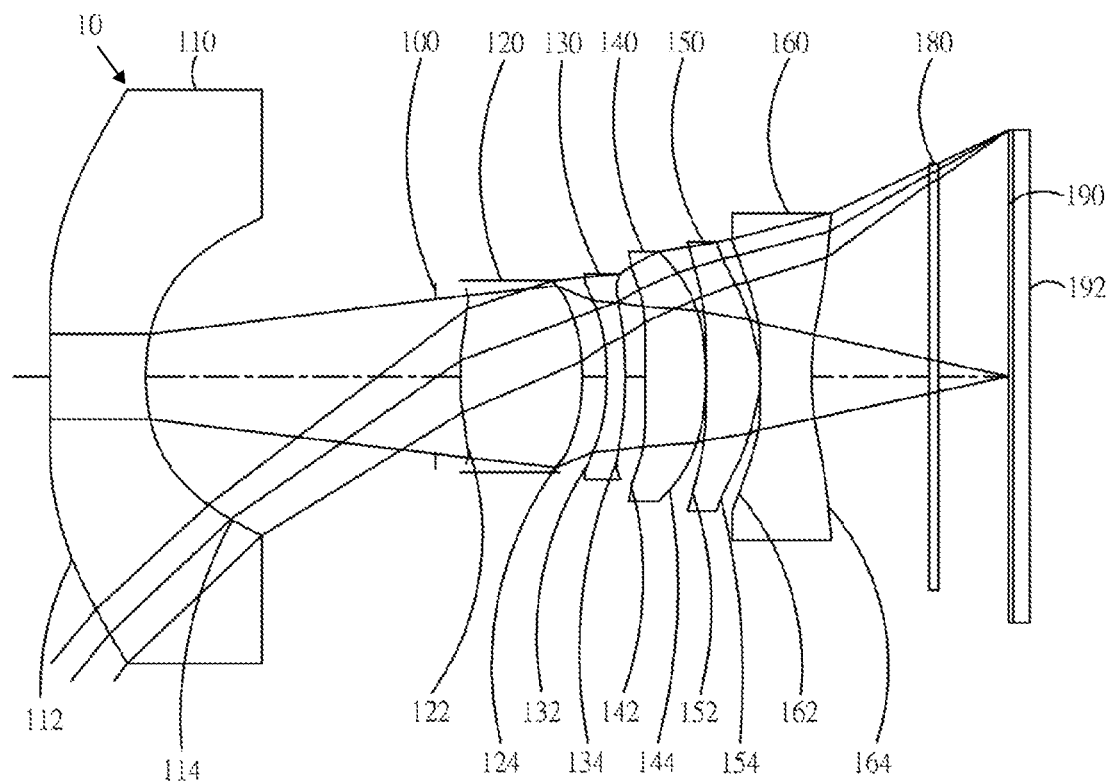
FIG. 2A is a schematic diagram showing a first optical embodiment of the present invention.
Figure 2B:
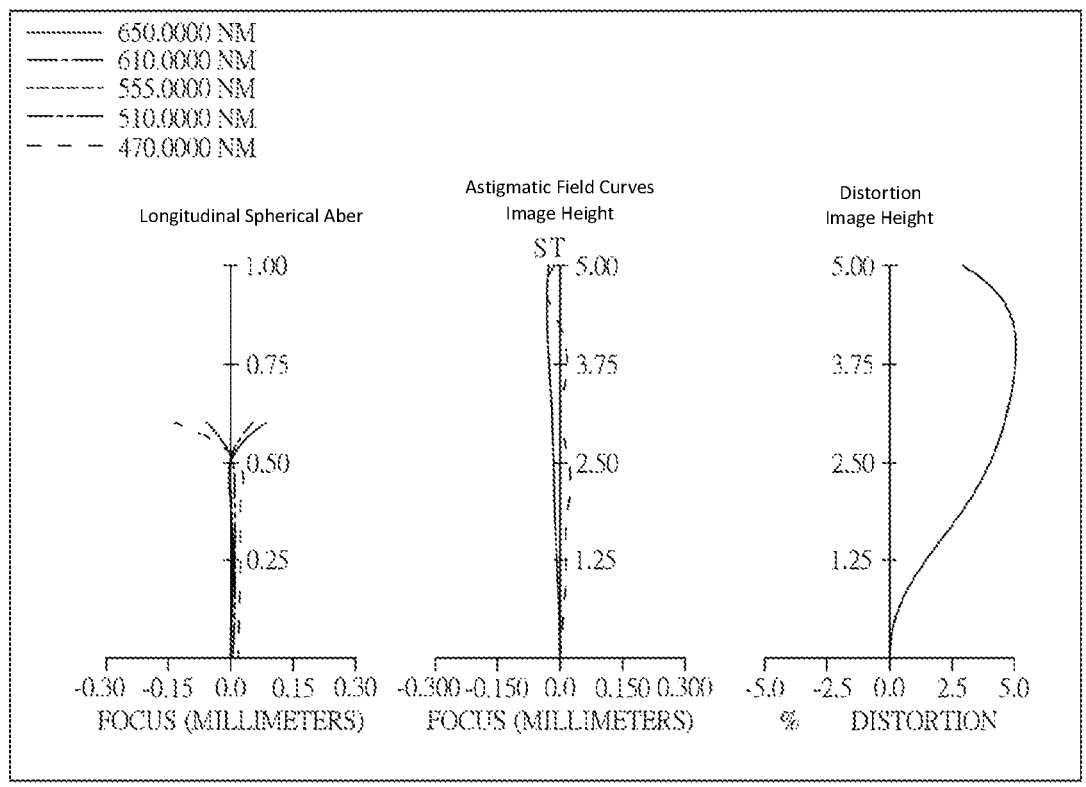
FIG. 2B shows curve diagrams of longitudinal spherical aberration, astigmatic field, and optical distortion of the optical image capturing system according to the first optical embodiment of the present invention in order from left to right.

As shown in FIG. 2A and FIG. 2B, wherein a lens group of an optical image capturing system 10 of a first optical embodiment of the present invention is illustrated in FIG. 2A, and FIG. 2B shows curve diagrams of longitudinal spherical aberration, astigmatic field, and optical distortion of the optical image capturing system in the order from left to right of the first optical embodiment. The optical image capturing system 10 of the first optical embodiment includes, along an optical axis from an object side to an image side, a first lens 110, an aperture 100, a second lens 120, a third lens 130, a fourth lens 140, a fifth lens 150, a sixth lens 160, an infrared rays filter 180, an image plane 190, and an image sensor 192.

The first lens 110 has negative refractive power and is made of plastic. An object-side surface 112 thereof, which faces the object side, is a concave aspheric surface, and an image-side surface 114 thereof, which faces the image side, is a concave aspheric surface. The object-side surface 112 has two inflection points. A profile curve length of the maximum effective radius of the object-side surface 112 of the first lens 110 is denoted by ARS11, and a profile curve length of the maximum effective radius of the image-side surface 114 of the first lens 110 is denoted by ARS12. A profile curve length of half the entrance pupil diameter (HEP) of the object-side surface 112 of the first lens 110 is denoted by ARE11, and a profile curve length of half the entrance pupil diameter (HEP) of the image-side surface 114 of the first lens 110 is denoted by ARE12. A thickness of the first lens 110 on the optical axis is denoted by TP1.

The first lens satisfies SGI111=−0.0031 mm; |SGI111|/(|SGI111|+TP1)=0.0016, where a displacement on the optical axis from a point on the object-side surface 112 of the first lens 110, through which the optical axis passes, to a point where the inflection point on the object-side surface 112, which is the closest to the optical axis, projects on the optical axis, is denoted by SGI111, and a displacement on the optical axis from a point on the image-side surface 114 of the first lens 110, through which the optical axis passes, to a point where the inflection point on the image-side surface 114, which is the closest to the optical axis, projects on the optical axis is denoted by SGI121.

The first lens 110 satisfies SGI112=1.3178 mm; |SGI112|/(|SGI112|+TP1)=0.4052, where a displacement on the optical axis from a point on the object-side surface 112 of the first lens 110, through which the optical axis passes, to a point where the inflection point on the object-side surface 112, which is the second closest to the optical axis, projects on the optical axis, is denoted by SGI112, and a displacement on the optical axis from a point on the image-side surface 114 of the first lens 110, through which the optical axis passes, to a point where the inflection point on the image-side surface 114, which is the second closest to the optical axis, projects on the optical axis is denoted by SGI122.

The first lens 110 satisfies HIF111=0.5557 mm; HIF111/HOI=0.1111, where a displacement perpendicular to the optical axis from a point on the object-side surface 112 of the first lens 110, through which the optical axis passes, to the inflection point, which is the closest to the optical axis is denoted by HIF111, and a displacement perpendicular to the optical axis from a point on the image-side surface 114 of the first lens 110, through which the optical axis passes, to the inflection point, which is the closest to the optical axis is denoted by HIF121.

The first lens 110 satisfies HIF112=5.3732 mm; HIF112/HOI=1.0746, where a displacement perpendicular to the optical axis from a point on the object-side surface 112 of the first lens 110, through which the optical axis passes, to the inflection point, which is the second closest to the optical axis is denoted by HIF112, and a displacement perpendicular to the optical axis from a point on the image-side surface 114 of the first lens 110, through which the optical axis passes, to the inflection point, which is the second closest to the optical axis is denoted by HIF122.

The second lens 120 has positive refractive power and is made of plastic. An object-side surface 122 thereof, which faces the object side, is a convex aspheric surface, and an image-side surface 124 thereof, which faces the image side, is a convex aspheric surface. The object-side surface 122 has an inflection point. A profile curve length of the maximum effective radius of the object-side surface 122 of the second lens 120 is denoted by ARS21, and a profile curve length of the maximum effective radius of the image-side surface 124 of the second lens 120 is denoted by ARS22. A profile curve length of half the entrance pupil diameter (HEP) of the object-side surface 122 of the second lens 120 is denoted by ARE21, and a profile curve length of half the entrance pupil diameter (HEP) of the image-side surface 124 of the second lens 120 is denoted by ARE22. A thickness of the second lens 120 on the optical axis is denoted by TP2.

The second lens 120 satisfies SGI211=0.1069 mm; |SGI211|/(|SGI211|+TP2)=0.0412; SGI221=0 mm; |SGI221|/(|SGI221|+TP2)=0, where a displacement on the optical axis from a point on the object-side surface 122 of the second lens 120, through which the optical axis passes, to a point where the inflection point on the object-side surface 122, which is the closest to the optical axis, projects on the optical axis, is denoted by SGI211, and a displacement on the optical axis from a point on the image-side surface 124 of the second lens 120, through which the optical axis passes, to a point where the inflection point on the image-side surface 124, which is the closest to the optical axis, projects on the optical axis is denoted by SGI221.

The second lens 120 satisfies HIF211=1.1264 mm; HIF211/HOI=0.2253; HIF221=0 mm; HIF221/HOI=0, where a displacement perpendicular to the optical axis from a point on the object-side surface 122 of the second lens 120, through which the optical axis passes, to the inflection point, which is the closest to the optical axis is denoted by HIF211, and a displacement perpendicular to the optical axis from a point on the image-side surface 124 of the second lens 120, through which the optical axis passes, to the inflection point, which is the closest to the optical axis is denoted by HIF221.

The third lens 130 has negative refractive power and is made of plastic. An object-side surface 132, which faces the object side, is a concave aspheric surface, and an image-side surface 134, which faces the image side, is a convex aspheric surface. The object-side surface 132 has an inflection point, and the image-side surface 134 has an inflection point. The object-side surface 122 has an inflection point. A profile curve length of the maximum effective radius of the object-side surface 132 of the third lens 130 is denoted by ARS31, and a profile curve length of the maximum effective radius of the image-side surface 134 of the third lens 130 is denoted by ARS32. A profile curve length of half the entrance pupil diameter (HEP) of the object-side surface 132 of the third lens 130 is denoted by ARE31, and a profile curve length of half the entrance pupil diameter (HEP) of the image-side surface 134 of the third lens 130 is denoted by ARE32. A thickness of the third lens 130 on the optical axis is denoted by TP3.

The third lens 130 satisfies SGI311=−0.3041 mm; |SGI311|/(|SGI311|+TP3)=0.4445; SGI321=−0.1172 mm; |SGI321|/(|SGI321|+TP3)=0.2357, where SGI311 is a displacement on the optical axis from a point on the object-side surface 132 of the third lens 130, through which the optical axis passes, to a point where the inflection point on the object-side surface 132, which is the closest to the optical axis, projects on the optical axis, and SGI321 is a displacement on the optical axis from a point on the image-side surface 134 of the third lens 130, through which the optical axis passes, to a point where the inflection point on the image-side surface 134, which is the closest to the optical axis, projects on the optical axis.

The third lens 130 satisfies HIF311=1.5907 mm; HIF311/HOI=0.3181; HIF321=1.3380 mm; HIF321/HOI=0.2676, where HIF311 is a distance perpendicular to the optical axis between the inflection point on the object-side surface 132 of the third lens 130, which is the closest to the optical axis, and the optical axis; HIF321 is a distance perpendicular to the optical axis between the inflection point on the image-side surface 134 of the third lens 130, which is the closest to the optical axis, and the optical axis.

The fourth lens 140 has positive refractive power and is made of plastic. An object-side surface 142, which faces the object side, is a convex aspheric surface, and an image-side surface 144, which faces the image side, is a concave aspheric surface. The object-side surface 142 has two inflection points, and the image-side surface 144 has an inflection point. A profile curve length of the maximum effective radius of the object-side surface 142 of the fourth lens 140 is denoted by ARS41, and a profile curve length of the maximum effective radius of the image-side surface 144 of the fourth lens 140 is denoted by ARS42. A profile curve length of half the entrance pupil diameter (HEP) of the object-side surface 142 of the fourth lens 140 is denoted by ARE41, and a profile curve length of half the entrance pupil diameter (HEP) of the image-side surface 144 of the fourth lens 140 is denoted by ARE42. A thickness of the fourth lens 140 on the optical axis is TP4.

The fourth lens 140 satisfies SGI411=0.0070 mm; |SGI411|/(|SGI411|+TP4)=0.0056; SGI421=0.0006 mm; |SGI421|/(|SGI4211+TP4)=0.0005, where SGI411 is a displacement on the optical axis from a point on the object-side surface 142 of the fourth lens 140, through which the optical axis passes, to a point where the inflection point on the object-side surface 142, which is the closest to the optical axis, projects on the optical axis, and SGI421 is a displacement on the optical axis from a point on the image-side surface 144 of the fourth lens 140, through which the optical axis passes, to a point where the inflection point on the image-side surface 144, which is the closest to the optical axis, projects on the optical axis.

The fourth lens 140 satisfies SGI412=−0.2078 mm; |SGI412|/(|SGI412|+TP4)=0.1439, where SGI412 is a displacement on the optical axis from a point on the object-side surface 142 of the fourth lens 140, through which the optical axis passes, to a point where the inflection point on the object-side surface 142, which is the second closest to the optical axis, projects on the optical axis, and SGI422 is a displacement on the optical axis from a point on the image-side surface 144 of the fourth lens 140, through which the optical axis passes, to a point where the inflection point on the image-side surface 144, which is the second closest to the optical axis, projects on the optical axis.

The fourth lens 140 further satisfies HIF411=0.4706 mm; HIF411/HOI=0.0941; HIF421=0.1721 mm; HIF421/HOI=0.0344, where HIF411 is a distance perpendicular to the optical axis between the inflection point on the object-side surface 142 of the fourth lens 140, which is the closest to the optical axis, and the optical axis; HIF421 is a distance perpendicular to the optical axis between the inflection point on the image-side surface 144 of the fourth lens 140, which is the closest to the optical axis, and the optical axis.

The fourth lens 140 satisfies HIF412=2.0421 mm; HIF412/HOI=0.4084, where HIF412 is a distance perpendicular to the optical axis between the inflection point on the object-side surface 142 of the fourth lens 140, which is the second closest to the optical axis, and the optical axis; HIF422 is a distance perpendicular to the optical axis between the inflection point on the image-side surface 144 of the fourth lens 140, which is the second closest to the optical axis, and the optical axis.

The fifth lens 150 has positive refractive power and is made of plastic. An object-side surface 152, which faces the object side, is a convex aspheric surface, and an image-side surface 154, which faces the image side, is a convex aspheric surface. The object-side surface 152 has two inflection points, and the image-side surface 154 has an inflection point. A profile curve length of the maximum effective radius of the object-side surface 152 of the fifth lens 150 is denoted by ARS51, and a profile curve length of the maximum effective radius of the image-side surface 154 of the fifth lens 150 is denoted by ARS52. A profile curve length of half the entrance pupil diameter (HEP) of the object-side surface 152 of the fifth lens 150 is denoted by ARE51, and a profile curve length of half the entrance pupil diameter (HEP) of the image-side surface 154 of the fifth lens 150 is denoted by ARE52. A thickness of the fifth lens 150 on the optical axis is denoted by TP5.

The fifth lens 150 satisfies SGI511=0.00364 mm; SGI521=−0.63365 mm; |SGI511|/(|SGI511|+TP5)=0.00338; |SGI521|/(|SGI521|+TP5)=0.37154, where SGI511 is a displacement on the optical axis from a point on the object-side surface 152 of the fifth lens 150, through which the optical axis passes, to a point where the inflection point on the object-side surface 152, which is the closest to the optical axis, projects on the optical axis, and SGI521 is a displacement on the optical axis from a point on the image-side surface 154 of the fifth lens 150, through which the optical axis passes, to a point where the inflection point on the image-side surface 154, which is the closest to the optical axis, projects on the optical axis.

The fifth lens 150 satisfies SGI512=−0.32032 mm; |SGI512|/(|SGI512|+TP5)=0.23009, where SGI512 is a displacement on the optical axis from a point on the object-side surface 152 of the fifth lens 150, through which the optical axis passes, to a point where the inflection point on the object-side surface 152, which is the second closest to the optical axis, projects on the optical axis, and SGI522 is a displacement on the optical axis from a point on the image-side surface 154 of the fifth lens 150, through which the optical axis passes, to a point where the inflection point on the image-side surface 154, which is the second closest to the optical axis, projects on the optical axis.

The fifth lens 150 satisfies SGI513=0 mm; SGI523=0 mm; |SGI513|/(|SGI513|+TP5)=0; |SGI523|/(|SGI523|+TP5)=0, where SGI513 is a displacement on the optical axis from a point on the object-side surface 152 of the fifth lens 150, through which the optical axis passes, to a point where the inflection point on the object-side surface 152, which is the third closest to the optical axis, projects on the optical axis, and SGI523 is a displacement on the optical axis from a point on the image-side surface 154 of the fifth lens 150, through which the optical axis passes, to a point where the inflection point on the image-side surface 154, which is the third closest to the optical axis, projects on the optical axis.

The fifth lens 150 satisfies SGI514=0 mm; SGI524=0 mm; |SGI514|/(|SGI514|+TP5)=0; |SGI524|/(|SGI524|+TP5)=0, where SGI514 is a displacement on the optical axis from a point on the object-side surface 152 of the fifth lens 150, through which the optical axis passes, to a point where the inflection point on the object-side surface 152, which is the fourth closest to the optical axis, projects on the optical axis, and SGI524 is a displacement on the optical axis from a point on the image-side surface 154 of the fifth lens 150, through which the optical axis passes, to a point where the inflection point on the image-side surface 154, which is the fourth closest to the optical axis, projects on the optical axis.

The fifth lens 150 further satisfies HIF511=0.28212 mm; HIF521=2.13850 mm; HIF511/HOI=0.05642; HIF521/HOI=0.42770, where HIF511 is a distance perpendicular to the optical axis between the inflection point on the object-side surface 152 of the fifth lens 150, which is the closest to the optical axis, and the optical axis; HIF521 is a distance perpendicular to the optical axis between the inflection point on the image-side surface 154 of the fifth lens 150, which is the closest to the optical axis, and the optical axis.

The fifth lens 150 further satisfies HIF512=2.51384 mm; HIF512/HOI=0.50277, where HIF512 is a distance perpendicular to the optical axis between the inflection point on the object-side surface 152 of the fifth lens 150, which is the second closest to the optical axis, and the optical axis; HIF522 is a distance perpendicular to the optical axis between the inflection point on the image-side surface 154 of the fifth lens 150, which is the second closest to the optical axis, and the optical axis.

The fifth lens 150 further satisfies HIF513=0 mm; HIF513/HOI=0; HIF523=0 mm; HIF523/HOI=0, where HIF513 is a distance perpendicular to the optical axis between the inflection point on the object-side surface 152 of the fifth lens 150, which is the third closest to the optical axis, and the optical axis; HIF523 is a distance perpendicular to the optical axis between the inflection point on the image-side surface 154 of the fifth lens 150, which is the third closest to the optical axis, and the optical axis.

The fifth lens 150 further satisfies HIF514=0 mm; HIF514/HOI=0; HIF524=0 mm; HIF524/HOI=0, where HIF514 is a distance perpendicular to the optical axis between the inflection point on the object-side surface 152 of the fifth lens 150, which is the fourth closest to the optical axis, and the optical axis; HIF524 is a distance perpendicular to the optical axis between the inflection point on the image-side surface 154 of the fifth lens 150, which is the fourth closest to the optical axis, and the optical axis.

The sixth lens 160 has negative refractive power and is made of plastic. An object-side surface 162, which faces the object side, is a concave surface, and an image-side surface 164, which faces the image side, is a concave surface. The object-side surface 162 has two inflection points, and the image-side surface 164 has an inflection point. Whereby, the incident angle of each view field entering the sixth lens 160 could be effectively adjusted to improve aberration. A profile curve length of the maximum effective radius of the object-side surface 162 of the sixth lens 160 is denoted by ARS61, and a profile curve length of the maximum effective radius of the image-side surface 164 of the sixth lens 160 is denoted by ARS62. A profile curve length of half the entrance pupil diameter (HEP) of the object-side surface 162 of the sixth lens 160 is denoted by ARE61, and a profile curve length of half the entrance pupil diameter (HEP) of the image-side surface 164 of the sixth lens 160 is denoted by ARE62. A thickness of the sixth lens 160 on the optical axis is denoted by TP6.

The sixth lens 160 satisfies SGI611=−0.38558 mm; SGI621=0.12386 mm; |SGI611|/(|SGI611|+TP6)=0.27212; |SGI621|/(|SGI621|+TP6)=0.10722, where SGI611 is a displacement on the optical axis from a point on the object-side surface 162 of the sixth lens 160, through which the optical axis passes, to a point where the inflection point on the object-side surface 162, which is the closest to the optical axis, projects on the optical axis, and SGI621 is a displacement on the optical axis from a point on the image-side surface 164 of the sixth lens 160, through which the optical axis passes, to a point where the inflection point on the image-side surface 164, which is the closest to the optical axis, projects on the optical axis.

The sixth lens 160 satisfies SGI612=−0.47400 mm; |SGI612|/(|SGI612|+TP6)=0.31488; SGI622=0 mm; |SGI622|/(|SGI622|+TP6)=0, where SGI612 is a displacement on the optical axis from a point on the object-side surface 162 of the sixth lens 160, through which the optical axis passes, to a point where the inflection point on the object-side surface 162, which is the second closest to the optical axis, projects on the optical axis, and SGI622 is a displacement on the optical axis from a point on the image-side surface 164 of the sixth lens 160, through which the optical axis passes, to a point where the inflection point on the image-side surface 164, which is the second closest to the optical axis, projects on the optical axis.

The sixth lens 160 further satisfies HIF611=2.24283 mm; HIF621=1.07376 mm; HIF611/HOI=0.44857; HIF621/HOI=0.21475, where HIF611 is a distance perpendicular to the optical axis between the inflection point on the object-side surface 162 of the sixth lens 160, which is the closest to the optical axis, and the optical axis; HIF621 is a distance perpendicular to the optical axis between the inflection point on the image-side surface 164 of the sixth lens 160, which is the closest to the optical axis, and the optical axis.

The sixth lens 160 further satisfies HIF612=2.48895 mm; HIF612/HOI=0.49779, where HIF612 is a distance perpendicular to the optical axis between the inflection point on the object-side surface 162 of the sixth lens 160, which is the second closest to the optical axis, and the optical axis; HIF622 is a distance perpendicular to the optical axis between the inflection point on the image-side surface 164 of the sixth lens 160, which is the second closest to the optical axis, and the optical axis.

The sixth lens 160 further satisfies HIF613=0 mm; HIF613/HOI=0; HIF623=0 mm; HIF623/HOI=0, where HIF613 is a distance perpendicular to the optical axis between the inflection point on the object-side surface 162 of the sixth lens 160, which is the third closest to the optical axis, and the optical axis; HIF623 is a distance perpendicular to the optical axis between the inflection point on the image-side surface 164 of the sixth lens 160, which is the third closest to the optical axis, and the optical axis.

The sixth lens 160 further satisfies HIF614=0 mm; HIF614/HOI=0; HIF624=0 mm; HIF624/HOI=0, where HIF614 is a distance perpendicular to the optical axis between the inflection point on the object-side surface 162 of the sixth lens 160, which is the fourth closest to the optical axis, and the optical axis; HIF624 is a distance perpendicular to the optical axis between the inflection point on the image-side surface 164 of the sixth lens 160, which is the fourth closest to the optical axis, and the optical axis.

The infrared rays filter 180 is made of glass and is disposed between the sixth lens 160 and the image plane 190. The infrared rays filter 180 gives no contribution to the focal length of the optical image capturing system 10.

The optical image capturing system 10 of the first optical embodiment has the following parameters, which are f=4.075 mm; f/HEP=1.4; HAF=50.001 degrees; and tan (HAF)=1.1918, where f is a focal length of the lens group; HAF is half the maximum field angle; and HEP is an entrance pupil diameter.

The parameters of the lenses of the first optical embodiment are f1=−7.828 mm; |f/f1|=0.52060; f6=−4.886; and |f1|>f6, where f1 is a focal length of the first lens 110; and f6 is a focal length of the sixth lens 160.

The first optical embodiment further satisfies |f2|+|f3|+|f4|+|f5|=95.50815; |f1|+|f6|=12.71352 and |f2|+|f3|+|f4|+|f5|>|f1|+|f6|, where f2 is a focal length of the second lens 120, f3 is a focal length of the third lens 130, f4 is a focal length of the fourth lens 140, f5 is a focal length of the fifth lens 150.

The optical image capturing system 10 of the first optical embodiment further satisfies ΣPPR=f/f2+f/f4+f/f5=1.63290; ΣNPR=|f/f1|+|f/f3|+|f/f6|=1.51305; ΣPPR/|ΣNPR|=1.07921; |f/f2|=0.69101; |f/f3|=0.15834; |f/f4|=0.06883; |f/f5|=0.87305; and |f/f6|=0.83412, where PPR is a ratio of a focal length f of the optical image capturing system to a focal length fp of each of the lenses with positive refractive power; and NPR is a ratio of a focal length f of the optical image capturing system to a focal length fn of each of lenses with negative refractive power.

The optical image capturing system 10 of the first optical embodiment further satisfies InTL+BFL=HOS; HOS=19.54120 mm; HOI=5.0 mm; HOS/HOI=3.90824; HOS/f=4.7952; InS=11.685 mm; InTL/HOS=0.9171; and InS/HOS=0.59794, where InTL is an optical axis distance between the object-side surface 112 of the first lens 110 and the image-side surface 164 of the sixth lens 160; HOS is a height of the image capturing system, i.e. an optical axis distance between the object-side surface 112 of the first lens 110 and the image plane 190; InS is an optical axis distance between the aperture 100 and the image plane 190; HOI is half a diagonal of an effective sensing area of the image sensor 192, i.e., the maximum image height; and BFL is a distance between the image-side surface 164 of the sixth lens 160 and the image plane 190.

The optical image capturing system 10 of the first optical embodiment further satisfies ΣTP=8.13899 mm; and ΣTP/InTL=0.52477, where ΣTP is a sum of the thicknesses of the lenses 110-160 with refractive power. It is helpful for the contrast of image and yield rate of manufacture and provides a suitable back focal length for installation of other elements.

The optical image capturing system 10 of the first optical embodiment further satisfies |R1/R2|=8.99987, where R1 is a radius of curvature of the object-side surface 112 of the first lens 110, and R2 is a radius of curvature of the image-side surface 114 of the first lens 110. It provides the first lens 110 with a suitable positive refractive power to reduce the increase rate of the spherical aberration.

The optical image capturing system 10 of the first optical embodiment further satisfies (R11−R12)/(R11+R12)=1.27780, where R11 is a radius of curvature of the object-side surface 162 of the sixth lens 160, and R12 is a radius of curvature of the image-side surface 164 of the sixth lens 160. It may modify the astigmatic field curvature.

The optical image capturing system 10 of the first optical embodiment further satisfies ΣPP=f2+f4+f5=69.770 mm; and f5/(f2+f4+f5)=0.067, where ΣPP is a sum of the focal lengths fp of each lens with positive refractive power. It is helpful to share the positive refractive power of a single lens to other positive lenses to avoid the significant aberration caused by the incident rays.

The optical image capturing system 10 of the first optical embodiment further satisfies ΣNP=f1+f3+f6=−38.451 mm; and f6/(f1+f3+f6)=0.127, where ΣNP is a sum of the focal lengths fn of each lens with negative refractive power. It is helpful to share the negative refractive power of the sixth lens 160 to the other negative lens, which avoids the significant aberration caused by the incident rays.

The optical image capturing system 10 of the first optical embodiment further satisfies IN12=6.418 mm; IN12/f=1.57491, where IN12 is a distance on the optical axis between the first lens 110 and the second lens 120. It may correct chromatic aberration and improve the performance.

The optical image capturing system 10 of the first optical embodiment further satisfies IN56=0.025 mm; IN56/f=0.00613, where IN56 is a distance on the optical axis between the fifth lens 150 and the sixth lens 160. It may correct chromatic aberration and improve the performance.

The optical image capturing system 10 of the first optical embodiment further satisfies TP1=1.934 mm; TP2=2.486 mm; and (TP1+IN12)/TP2=3.36005, where TP1 is a central thickness of the first lens 110 on the optical axis, and TP2 is a central thickness of the second lens 120 on the optical axis. It may control the sensitivity of manufacture of the optical image capturing system and improve the performance.

The optical image capturing system 10 of the first optical embodiment further satisfies TP5=1.072 mm; TP6=1.031 mm; and (TP6+IN56)/TP5=0.98555, where TP5 is a central thickness of the fifth lens 150 on the optical axis, TP6 is a central thickness of the sixth lens 160 on the optical axis, and IN56 is a distance on the optical axis between the fifth lens 150 and the sixth lens 160. It may control the sensitivity of manufacture of the optical image capturing system and lower the total height of the optical image capturing system.

The optical image capturing system 10 of the first optical embodiment further satisfies IN34=0.401 mm; IN45=0.025 mm; and TP4/(IN34+TP4+IN45)=0.74376, where TP4 is a central thickness of the fourth lens 140 on the optical axis; IN34 is a distance on the optical axis between the third lens 130 and the fourth lens 140; IN45 is a distance on the optical axis between the fourth lens 140 and the fifth lens 150. It may help to slightly correct the aberration caused by the incident rays and lower the total height of the optical image capturing system.

The optical image capturing system 10 of the first optical embodiment further satisfies InRS51=−0.34789 mm; InRS52=−0.88185 mm; |InRS51|/TP5=0.32458; and |InRS52|/TP5=0.82276, where InRS51 is a displacement from a point on the object-side surface 152 of the fifth lens 150 passed through by the optical axis to a point on the optical axis where a projection of the maximum effective semi diameter of the object-side surface 152 of the fifth lens 150 ends; InRS52 is a displacement from a point on the image-side surface 154 of the fifth lens 150 passed through by the optical axis to a point on the optical axis where a projection of the maximum effective semi diameter of the image-side surface 154 of the fifth lens 150 ends; and TP5 is a central thickness of the fifth lens 150 on the optical axis. It is helpful for manufacturing and shaping of the lenses and is helpful to reduce the size.

The optical image capturing system 10 of the first optical embodiment further satisfies HVT51=0.515349 mm; and HVT52=0 mm, where HVT51 is a distance perpendicular to the optical axis between the critical point on the object-side surface 152 of the fifth lens 150 and the optical axis; and HVT52 is a distance perpendicular to the optical axis between the critical point on the image-side surface 154 of the fifth lens 150 and the optical axis.

The optical image capturing system 10 of the first optical embodiment further satisfies InRS61=−0.58390 mm; InRS62=0.41976 mm; |InRS61|/TP6=0.56616; and |InRS62|/TP6=0.40700, where InRS61 is a displacement from a point on the object-side surface 162 of the sixth lens 160 passed through by the optical axis to a point on the optical axis where a projection of the maximum effective semi diameter of the object-side surface 162 of the sixth lens 160 ends; InRS62 is a displacement from a point on the image-side surface 164 of the sixth lens 160 passed through by the optical axis to a point on the optical axis where a projection of the maximum effective semi diameter of the image-side surface 164 of the sixth lens 160 ends; and TP6 is a central thickness of the sixth lens 160 on the optical axis. It is helpful for manufacturing and shaping of the lenses and is helpful to reduce the size.

The optical image capturing system 10 of the first optical embodiment satisfies HVT61=0 mm; and HVT62=0 mm, where HVT61 is a distance perpendicular to the optical axis between the critical point on the object-side surface 162 of the sixth lens 160 and the optical axis; and HVT62 is a distance perpendicular to the optical axis between the critical point on the image-side surface 164 of the sixth lens 160 and the optical axis.

The optical image capturing system 10 of the first optical embodiment satisfies HVT51/HOI=0.1031. It is helpful for correction of the aberration of the peripheral view field of the optical image capturing system.

The optical image capturing system 10 of the first optical embodiment satisfies HVT51/HOS=0.02634. It is helpful for correction of the aberration of the peripheral view field of the optical image capturing system.

The second lens 120, the third lens 130, and the sixth lens 160 have negative refractive power. The optical image capturing system 10 of the first optical embodiment further satisfies NA6/NA2≤1, where NA2 is an Abbe number of the second lens 120; NA3 is an Abbe number of the third lens 130; NA6 is an Abbe number of the sixth lens 160. It may correct the aberration of the optical image capturing system.

The optical image capturing system 10 of the first optical embodiment further satisfies |TDT|=2.124%; |ODT|=5.076%, where TDT is TV distortion; and ODT is optical distortion.

The parameters of the lenses of the first optical embodiment are listed in Table 1 and Table 2.

TABLE 1 f = 4.075 mm; f/HEP = 1.4; HAF = 50.000 deg

| Surface | | Radius of curvature (mm) | Thickness (mm) | Material | Refractive index | Abbe number | Focal length (mm) |
|---|---|---|---|---|---|---|---|
| 0 | Object | plane | plane | | | | |
| 1 | 1st lens | −40.99625704 | 1.934 | plastic | 1.515 | 56.55 | −7.828 |
| 2 | | 4.555209289 | 5.923 | | | | |
| 3 | Aperture | plane | 0.495 | | | | |
| 4 | 2nd lens | 5.333427366 | 2.486 | plastic | 1.544 | 55.96 | 5.897 |
| 5 | | −6.781659971 | 0.502 | | | | |
| 6 | 3rd lens | −5.697794287 | 0.380 | plastic | 1.642 | 22.46 | −25.738 |
| 7 | | −8.883957518 | 0.401 | | | | |
| 8 | 4th lens | 13.19225664 | 1.236 | plastic | 1.544 | 55.96 | 59.205 |
| 9 | | 21.55681832 | 0.025 | | | | |
| 10 | 5th lens | 8.987806345 | 1.072 | plastic | 1.515 | 56.55 | 4.668 |
| 11 | | −3.158875374 | 0.025 | | | | |
| 12 | 6th lens | −29.46491425 | 1.031 | plastic | 1.642 | 22.46 | −4.886 |
| 13 | | 3.593484273 | 2.412 | | | | |
| 14 | Infrared rays filter | plane | 0.200 | | 1.517 | 64.13 | |

TABLE 1-continued f = 4.075 mm; f/HEP = 1.4; HAF = 50.000 deg

| Surface | Radius of curvature (mm) | Thickness (mm) | Material | Refractive index | Abbe number | Focal length (mm) |
|---|---|---|---|---|---|---|
| 15 | plane | 1.420 | | | | |
| 16 | Image plane | plane | | | | |

Reference wavelength (d-line): 555 mm; the position of blocking light: the effective radius of the clear aperture of the first surface is 5.800 mm; the effective diameter of the clear aperture of the third surface is 1.570 mm; the effective diameter of the clear aperture of the fifth surface is 1.950 mm.

TABLE 2

Coefficients of the aspheric surfaces

| | Surface | | | | | | |
|---|---|---|---|---|---|---|---|
| | 1 | 2 | 3 | 4 | 5 | 6 | 8 |
| k | 4.310876E+01 | −4.707622E+00 | 2.616025E+00 | 2.445397E+00 | 5.645686E+00 | −2.117147E+01 | −5.287220E+00 |
| A4 | 7.054243E−03 | 1.714312E−02 | −8.377541E−03 | −1.789549E−02 | −3.379055E−03 | −1.370959E−02 | −2.937377E−02 |
| A6 | −5.233264E−04 | −1.502232E−04 | −1.838068E−03 | −3.657520E−03 | −1.225453E−03 | 6.250200E−03 | 2.743532E−03 |
| A8 | 3.077890E−05 | −1.359611E−04 | 1.233332E−03 | −1.131622E−03 | −5.979572E−03 | −5.854426E−03 | −2.457574E−03 |
| A10 | −1.260650E−06 | 2.680747E−05 | −2.390895E−03 | 1.390351E−03 | 4.556449E−03 | 4.049451E−03 | 1.874319E−03 |
| A12 | 3.319093E−08 | −2.017491E−06 | 1.998555E−03 | −4.152857E−04 | −1.177175E−03 | −1.314592E−03 | −6.013661E−04 |
| A14 | −5.051600E−10 | 6.604615E−08 | −9.734019E−04 | 5.487286E−05 | 1.370522E−04 | 2.143097E−04 | 8.792480E−05 |
| A16 | 3.380000E−12 | −1.301630E−09 | 2.478373E−04 | −2.919339E−06 | −5.974015E−06 | −1.399894E−05 | −4.770527E−06 |

| | Surface | | | | |
|---|---|---|---|---|---|
| | 9 | 10 | 11 | 12 | 13 |
| k | 6.200000E+01 | −2.114008E+01 | −7.699904E+00 | −6.155476E+01 | −3.120467E−01 |
| A4 | −1.359965E−01 | −1.263831E−01 | −1.927804E−02 | −2.492467E−02 | −3.521844E−02 |
| A6 | 6.628518E−02 | 6.965399E−02 | 2.478376E−03 | −1.835360E−03 | 5.629654E−03 |
| A8 | −2.129167E−02 | −2.116027E−02 | 1.438785E−03 | 3.201343E−03 | −5.466925E−04 |
| A10 | 4.396344E−03 | 3.819371E−03 | −7.013749E−04 | −8.990757E−04 | 2.231154E−05 |
| A12 | −5.542899E−04 | −4.040283E−04 | 1.253214E−04 | 1.245343E−04 | 5.548990E−07 |
| A14 | 3.768879E−05 | 2.280473E−05 | −9.943196E−06 | −8.788363E−06 | −9.396920E−08 |
| A16 | −1.052467E−06 | −5.165452E−07 | 2.898397E−07 | 2.494302E−07 | 2.728360E−09 |

The figures related to the profile curve lengths obtained based on Table 1 and Table 2 are listed in the following table:

First optical embodiment (Reference wavelength (d-line): 555 mm)

| ARE | 1/2(HEP) | ARE value | ARE-1/2(HEP) | 2(ARE/HEP) % | TP | ARE/TP (%) |
|---|---|---|---|---|---|---|
| 11 | 1.455 | 1.455 | −0.00033 | 99.98% | 1.934 | 75.23% |
| 12 | 1.455 | 1.495 | 0.03957 | 102.72% | 1.934 | 77.29% |
| 21 | 1.455 | 1.465 | 0.00940 | 100.65% | 2.486 | 58.93% |
| 22 | 1.455 | 1.495 | 0.03950 | 102.71% | 2.486 | 60.14% |
| 31 | 1.455 | 1.486 | 0.03045 | 102.09% | 0.380 | 391.02% |
| 32 | 1.455 | 1.464 | 0.00830 | 100.57% | 0.380 | 385.19% |
| 41 | 1.455 | 1.458 | 0.00237 | 100.16% | 1.236 | 117.95% |
| 42 | 1.455 | 1.484 | 0.02825 | 101.94% | 1.236 | 120.04% |
| 51 | 1.455 | 1.462 | 0.00672 | 100.46% | 1.072 | 136.42% |
| 52 | 1.455 | 1.499 | 0.04335 | 102.98% | 1.072 | 139.83% |
| 61 | 1.455 | 1.465 | 0.00964 | 100.66% | 1.031 | 142.06% |
| 62 | 1.455 | 1.469 | 0.01374 | 100.94% | 1.031 | 142.45% |

| ARS | EHD | ARS value | ARS-EHD | (ARS/EHD) % | TP | ARS/TP (%) |
|---|---|---|---|---|---|---|
| 11 | 5.800 | 6.141 | 0.341 | 105.88% | 1.934 | 317.51% |
| 12 | 3.299 | 4.423 | 1.125 | 134.10% | 1.934 | 228.70% |
| 21 | 1.664 | 1.674 | 0.010 | 100.61% | 2.486 | 67.35% |
| 22 | 1.950 | 2.119 | 0.169 | 108.65% | 2.486 | 85.23% |
| 31 | 1.980 | 2.048 | 0.069 | 103.47% | 0.380 | 539.05% |
| 32 | 2.084 | 2.101 | 0.017 | 100.83% | 0.380 | 552.87% |
| 41 | 2.247 | 2.287 | 0.040 | 101.80% | 1.236 | 185.05% |
| 42 | 2.530 | 2.813 | 0.284 | 111.22% | 1.236 | 227.63% |
| 51 | 2.655 | 2.690 | 0.035 | 101.32% | 1.072 | 250.99% |
| 52 | 2.764 | 2.930 | 0.166 | 106.00% | 1.072 | 273.40% |

-continued

| | | First optical embodiment (Reference wavelength (d-line): 555 mm) | | | | |
|---|---|---|---|---|---|---|
| 61 | 2.816 | 2.905 | 0.089 | 103.16% | 1.031 | 281.64% |
| 62 | 3.363 | 3.391 | 0.029 | 100.86% | 1.031 | 328.83% |

The detailed data of FIG. 2B of the first optical embodiment are listed in Table 1, in which the unit of the radius of curvature, thickness, and focal length are millimeter, and surface 0-16 indicates the surfaces of all elements in the system in sequence from the object side to the image side. Table 2 is the list of coefficients of the aspheric surfaces, in which k indicates the taper coefficient in the aspheric curve equation, and A1-A20 indicate the coefficients of aspheric surfaces from the first order to the twentieth order of each aspheric surface. The following optical embodiments have similar diagrams and tables, which are the same as those of the first optical embodiment, so we do not describe it again. The definitions of the mechanism component parameters of the following optical embodiments are the same as those of the first optical embodiment.

Second Optical Embodiment

Figure 3A:
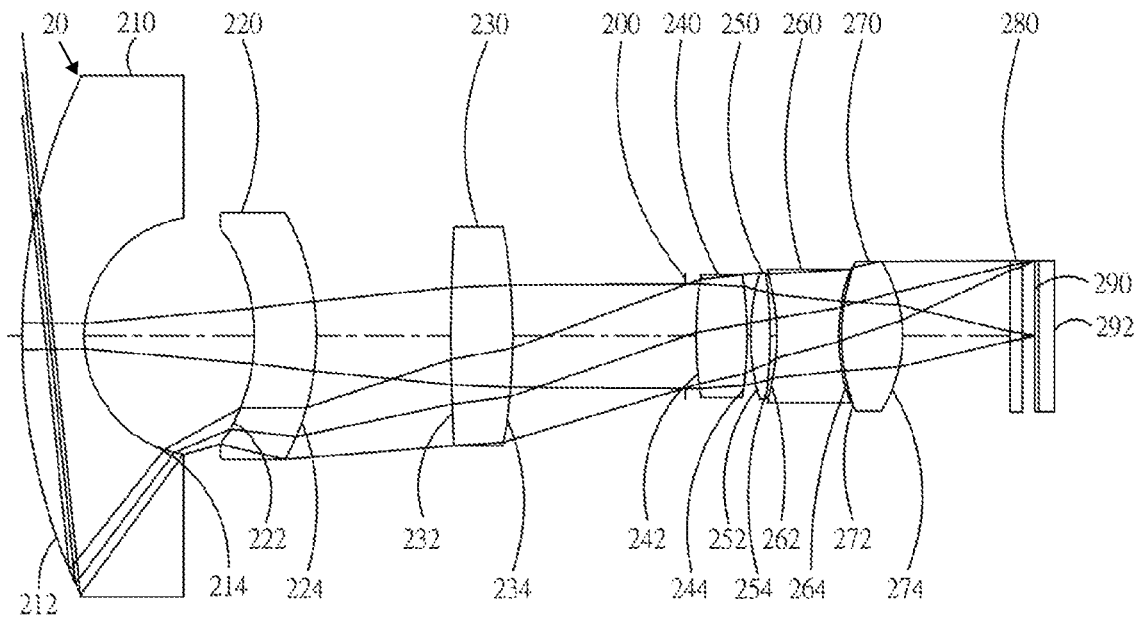
FIG. 3A is a schematic diagram showing a second optical embodiment of the present invention.
Figure 3B:
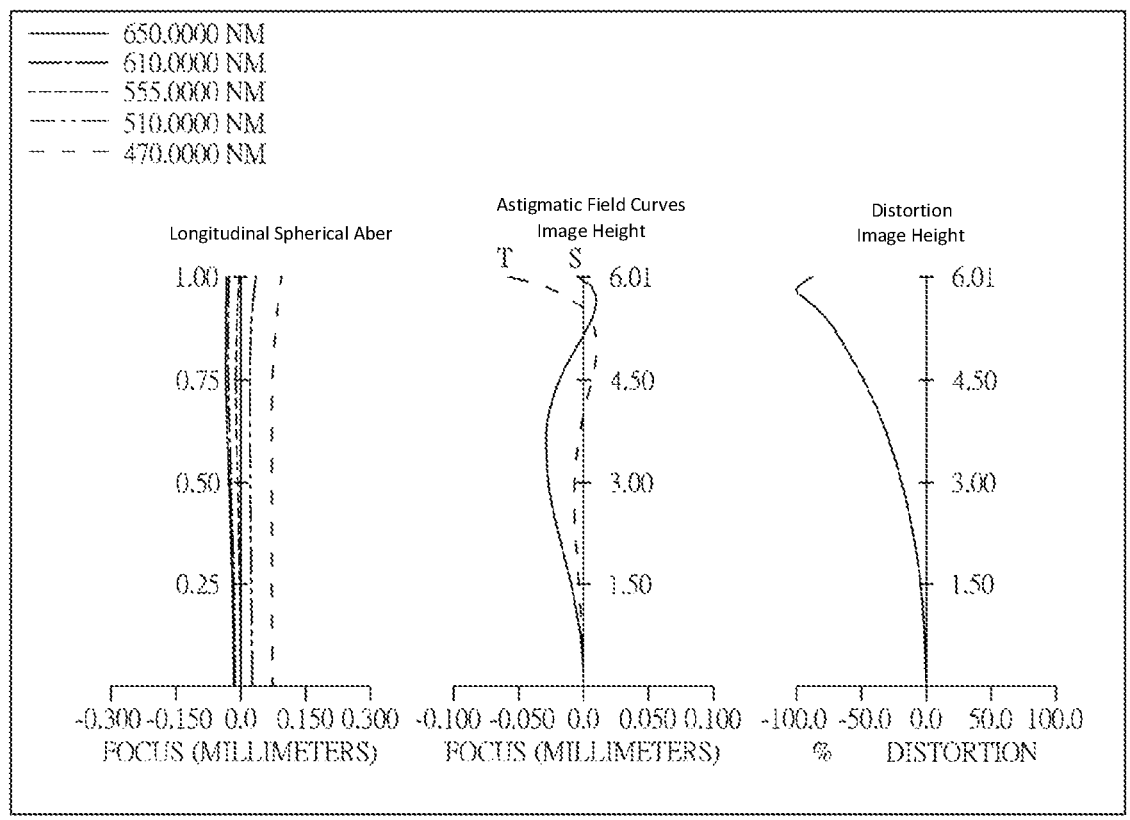
FIG. 3B shows curve diagrams of longitudinal spherical aberration, astigmatic field, and optical distortion of the optical image capturing system according to the second optical embodiment of the present application in order from left to right.

As shown in FIG. 3A and FIG. 3B, an optical image capturing system 20 of the second optical embodiment of the present invention includes, along an optical axis from an object side to an image side, a first lens 210, a second lens 220, a third lens 230, an aperture 200, a fourth lens 240, a fifth lens 250, a sixth lens 260, a seventh lens 270, an infrared rays filter 280, an image plane 290, and an image sensor 292.

The first lens 210 has negative refractive power and is made of glass. An object-side surface 212 thereof, which faces the object side, is a convex spherical surface, and an image-side surface 214 thereof, which faces the image side, is a concave spherical surface.

The second lens 220 has negative refractive power and is made of glass. An object-side surface 222 thereof, which faces the object side, is a concave spherical surface, and an image-side surface 224 thereof, which faces the image side, is a convex spherical surface.

The third lens 230 has positive refractive power and is made of glass. An object-side surface 232, which faces the object side, is a convex spherical surface, and an image-side surface 234, which faces the image side, is a convex spherical surface.

The fourth lens 240 has positive refractive power and is made of glass. An object-side surface 242, which faces the object side, is a convex spherical surface, and an image-side surface 244, which faces the image side, is a convex spherical surface.

The fifth lens 250 has positive refractive power and is made of glass. An object-side surface 252, which faces the object side, is a convex spherical surface, and an image-side surface 254, which faces the image side, is a convex spherical surface.

The sixth lens 260 has negative refractive power and is made of glass. An object-side surface 262, which faces the object side, is a concave aspherical surface, and an image-side surface 264, which faces the image side, is a concave aspherical surface. Whereby, the incident angle of each view field entering the sixth lens 260 could be effectively adjusted to improve aberration.

The seventh lens 270 has negative refractive power and is made of glass. An object-side surface 272, which faces the object side, is a convex surface, and an image-side surface 274, which faces the image side, is a convex surface. It may help to shorten the back focal length to keep small in size, and may reduce an incident angle of the light of an off-axis field of view and correct the aberration of the off-axis field of view.

The infrared rays filter 280 is made of glass and is disposed between the seventh lens 270 and the image plane 290. The infrared rays filter 280 gives no contribution to the focal length of the optical image capturing system 20.

The parameters of the lenses of the second optical embodiment are listed in Table 3 and Table 4.

TABLE 3

| | | f = 4.7601 mm; f/HEP = 2.2; HAF = 95.98 deg | | | | |
|---|---|---|---|---|---|---|
| Surface | | Radius of curvature (mm) | Thickness (mm) | Material | Refractive index | Abbe number | Focal length (mm) |
| 0 | Object | 1E+18 | 1E+18 | | | | |
| 1 | 1$^{st}$ lens | 47.71478323 | 4.977 | glass | 2.001 | 29.13 | −12.647 |
| 2 | | 9.527614761 | 13.737 | | | | |
| 3 | 2$^{nd}$ lens | −14.88061107 | 5.000 | glass | 2.001 | 29.13 | −99.541 |
| 4 | | −20.42046946 | 10.837 | | | | |
| 5 | 3$^{rd}$ lens | 182.4762997 | 5.000 | glass | 1.847 | 23.78 | 44.046 |
| 6 | | −46.71963608 | 13.902 | | | | |
| 7 | Aperture | 1E+18 | 0.850 | | | | |
| 8 | 4$^{th}$ lens | 28.60018103 | 4.095 | glass | 1.834 | 37.35 | 19.369 |
| 9 | | −35.08507586 | 0.323 | | | | |
| 10 | 5$^{th}$ lens | 18.25991342 | 1.539 | glass | 1.609 | 46.44 | 20.223 |
| 11 | | −36.99028878 | 0.546 | | | | |
| 12 | 6$^{th}$ lens | −18.24574524 | 5.000 | glass | 2.002 | 19.32 | −7.668 |
| 13 | | 15.33897192 | 0.215 | | | | |
| 14 | 7$^{th}$ lens | 16.13218937 | 4.933 | glass | 1.517 | 64.20 | 13.620 |
| 15 | | −11.24007 | 8.664 | | | | |
| 16 | Infrared rays filter | 1E+18 | 1.000 | BK_7 | 1.517 | 64.2 | |
| 17 | | 1E+18 | 1.007 | | | | |
| 18 | Image plane | 1E+18 | −0.007 | | | | |

Reference wavelength (d-line): 555 nm

TABLE 4

| Coefficients of the aspheric surfaces | | | | | | | |
|---|---|---|---|---|---|---|---|
| | Surface | | | | | | |
| | 1 | 2 | 3 | 4 | 5 | 6 | 8 |
| k | 0.000000E+00 | 0.000000E+00 | 0.000000E+00 | 0.000000E+00 | 0.000000E+00 | 0.000000E+00 | 0.000000E+00 |
| A4 | 0.000000E+00 | 0.000000E+00 | 0.000000E+00 | 0.000000E+00 | 0.000000E+00 | 0.000000E+00 | 0.000000E+00 |
| A6 | 0.000000E+00 | 0.000000E+00 | 0.000000E+00 | 0.000000E+00 | 0.000000E+00 | 0.000000E+00 | 0.000000E+00 |
| A8 | 0.000000E+00 | 0.000000E+00 | 0.000000E+00 | 0.000000E+00 | 0.000000E+00 | 0.000000E+00 | 0.000000E+00 |
| A10 | 0.000000E+00 | 0.000000E+00 | 0.000000E+00 | 0.000000E+00 | 0.000000E+00 | 0.000000E+00 | 0.000000E+00 |
| A12 | 0.000000E+00 | 0.000000E+00 | 0.000000E+00 | 0.000000E+00 | 0.000000E+00 | 0.000000E+00 | 0.000000E+00 |
| | Surface | | | | | | |
| | 9 | 10 | 11 | 12 | 13 | 14 | 15 |
| | 0.000000E+00 | 0.000000E+00 | 0.000000E+00 | 0.000000E+00 | 0.000000E+00 | 0.000000E+00 | 0.000000E+00 |
| A4 | 0.000000E+00 | 0.000000E+00 | 0.000000E+00 | 0.000000E+00 | 0.000000E+00 | 0.000000E+00 | 0.000000E+00 |
| A6 | 0.000000E+00 | 0.000000E+00 | 0.000000E+00 | 0.000000E+00 | 0.000000E+00 | 0.000000E+00 | 0.000000E+00 |
| A8 | 0.000000E+00 | 0.000000E+00 | 0.000000E+00 | 0.000000E+00 | 0.000000E+00 | 0.000000E+00 | 0.000000E+00 |
| A10 | 0.000000E+00 | 0.000000E+00 | 0.000000E+00 | 0.000000E+00 | 0.000000E+00 | 0.000000E+00 | 0.000000E+00 |
| A12 | 0.000000E+00 | 0.000000E+00 | 0.000000E+00 | 0.000000E+00 | 0.000000E+00 | 0.000000E+00 | 0.000000E+00 |

An equation of the aspheric surfaces of the second optical embodiment is the same as that of the first optical embodiment, and the definitions are the same as well.

The exact parameters of the second optical embodiment based on Table 3 and Table 4 are listed in the following table:

| Second optical embodiment (Reference wavelength: 555 nm) | | | | | |
|---|---|---|---|---|---|
| |f/f1| | |f/f2| | |f/f3| | |f/f4| | |f/f5| | |f/f6| |
| 0.3764 | 0.0478 | 0.1081 | 0.2458 | 0.2354 | 0.6208 |
| |f/f7| | ΣPPR | ΣNPR | ΣPPR/|ΣNPR| | IN12/f | IN67/f |
| 0.3495 | 1.3510 | 0.6327 | 2.1352 | 2.8858 | 0.0451 |
| |f1/f2| | |f2/f3| | (TP1 + IN12)/TP2 | | (TP7 + IN67)/TP6 | |
| 0.1271 | 2.2599 | 3.7428 | | 1.0296 | |
| HOS | InTL | HOS/HOI | InS/HOS | ODT % | TDT % |
| 81.6178 | 70.9539 | 13.6030 | 0.3451 | −113.2790 | 84.4806 |
| HVT11 | HVT12 | HVT21 | HVT22 | HVT31 | HVT32 |
| 0.0000 | 0.0000 | 0.0000 | 0.0000 | 0.0000 | 0.0000 |
| HVT61 | HVT62 | HVT71 | HVT72 | HVT72/HOI | HVT72/HOS |
| 0.0000 | 0.0000 | 0.0000 | 0.0000 | 0.0000 | 0.0000 |
| PhiA | | | | | HOI |
| 11.962 mm | | | | | 6 mm |
| | | | | | InTL/HOS |
| | | | | | 0.8693 |
| PSTA | PLTA | NSTA | NLTA | SSTA | SLTA |
| 0.060 mm | −0.005 mm | 0.016 mm | 0.006 mm | 0.020 mm | −0.008 mm |

The figures related to the profile curve lengths obtained based on Table 3 and Table 4 are listed in the following table:

Second optical embodiment (Reference wavelength: 555 nm)

| ARE | 1/2(HEP) | ARE value | ARE-1/2(HEP) | 2(ARE/HEP) % | TP | ARE/TP (%) |
|---|---|---|---|---|---|---|
| 11 | 1.082 | 1.081 | −0.00075 | 99.93% | 4.977 | 21.72% |
| 12 | 1.082 | 1.083 | 0.00149 | 100.14% | 4.977 | 21.77% |
| 21 | 1.082 | 1.082 | 0.00011 | 100.01% | 5.000 | 21.64% |
| 22 | 1.082 | 1.082 | −0.00034 | 99.97% | 5.000 | 21.63% |
| 31 | 1.082 | 1.081 | −0.00084 | 99.92% | 5.000 | 21.62% |
| 32 | 1.082 | 1.081 | −0.00075 | 99.93% | 5.000 | 21.62% |
| 41 | 1.082 | 1.081 | −0.00059 | 99.95% | 4.095 | 26.41% |
| 42 | 1.082 | 1.081 | −0.00067 | 99.94% | 4.095 | 26.40% |
| 51 | 1.082 | 1.082 | −0.00021 | 99.98% | 1.539 | 70.28% |
| 52 | 1.082 | 1.081 | −0.00069 | 99.94% | 1.539 | 70.25% |
| 61 | 1.082 | 1.082 | −0.00021 | 99.98% | 5.000 | 21.63% |
| 62 | 1.082 | 1.082 | 0.00005 | 100.00% | 5.000 | 21.64% |
| 71 | 1.082 | 1.082 | −0.00003 | 100.00% | 4.933 | 21.93% |
| 72 | 1.082 | 1.083 | 0.00083 | 100.08% | 4.933 | 21.95% |

| ARS | EHD | ARS value | ARS-EHD | (ARS/EHD) % | TP | ARS/TP (%) |
|---|---|---|---|---|---|---|
| 11 | 20.767 | 21.486 | 0.719 | 103.46% | 4.977 | 431.68% |
| 12 | 9.412 | 13.474 | 4.062 | 143.16% | 4.977 | 270.71% |
| 21 | 8.636 | 9.212 | 0.577 | 106.68% | 5.000 | 184.25% |
| 22 | 9.838 | 10.264 | 0.426 | 104.33% | 5.000 | 205.27% |
| 31 | 8.770 | 8.772 | 0.003 | 100.03% | 5.000 | 175.45% |
| 32 | 8.511 | 8.558 | 0.047 | 100.55% | 5.000 | 171.16% |
| 41 | 4.600 | 4.619 | 0.019 | 100.42% | 4.095 | 112.80% |
| 42 | 4.965 | 4.981 | 0.016 | 100.32% | 4.095 | 121.64% |
| 51 | 5.075 | 5.143 | 0.067 | 101.33% | 1.539 | 334.15% |
| 52 | 5.047 | 5.062 | 0.015 | 100.30% | 1.539 | 328.89% |
| 61 | 5.011 | 5.075 | 0.064 | 101.28% | 5.000 | 101.50% |
| 62 | 5.373 | 5.489 | 0.116 | 102.16% | 5.000 | 109.79% |
| 71 | 5.513 | 5.625 | 0.112 | 102.04% | 4.933 | 114.03% |
| 72 | 5.981 | 6.307 | 0.326 | 105.44% | 4.933 | 127.84% |

The results of the equations of the second optical embodiment based on Table 3 and Table 4 are listed in the following table:

Values related to the inflection points of the second optical embodiment (Reference wavelength: 555 nm)

| HIF111 | 0 | HIF111/HOI | 0 | SGI111 | 0 | |SGI111|/(|SGI111| + TP1) | 0 |

Third Optical Embodiment

Figure 4A:
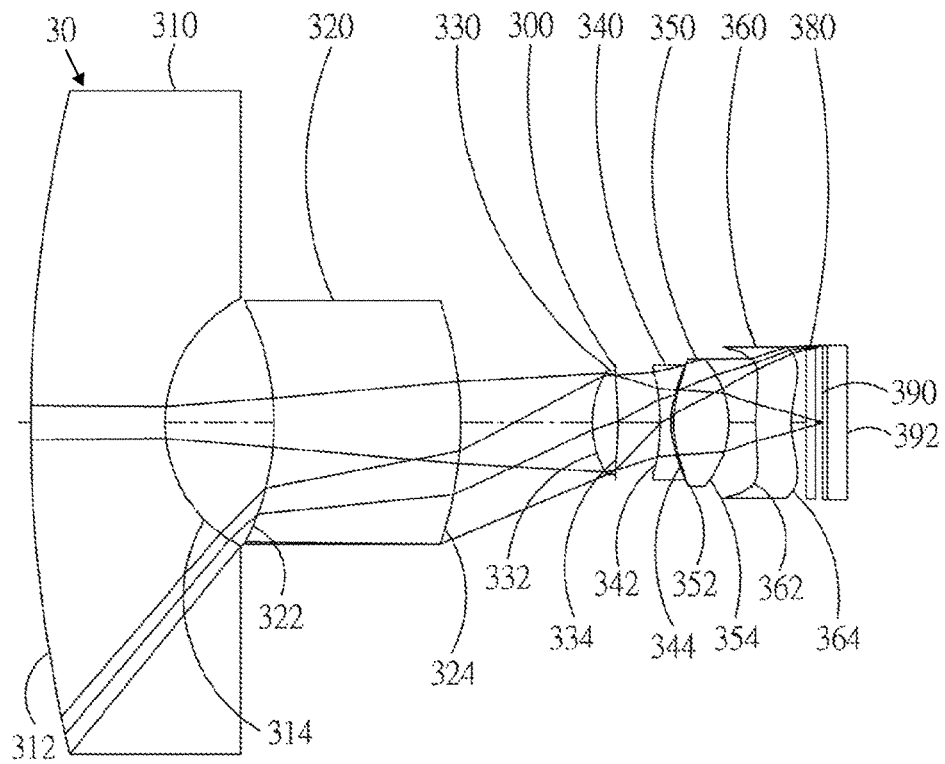
FIG. 4A is a schematic diagram showing a third optical embodiment of the present invention.
Figure 4B:
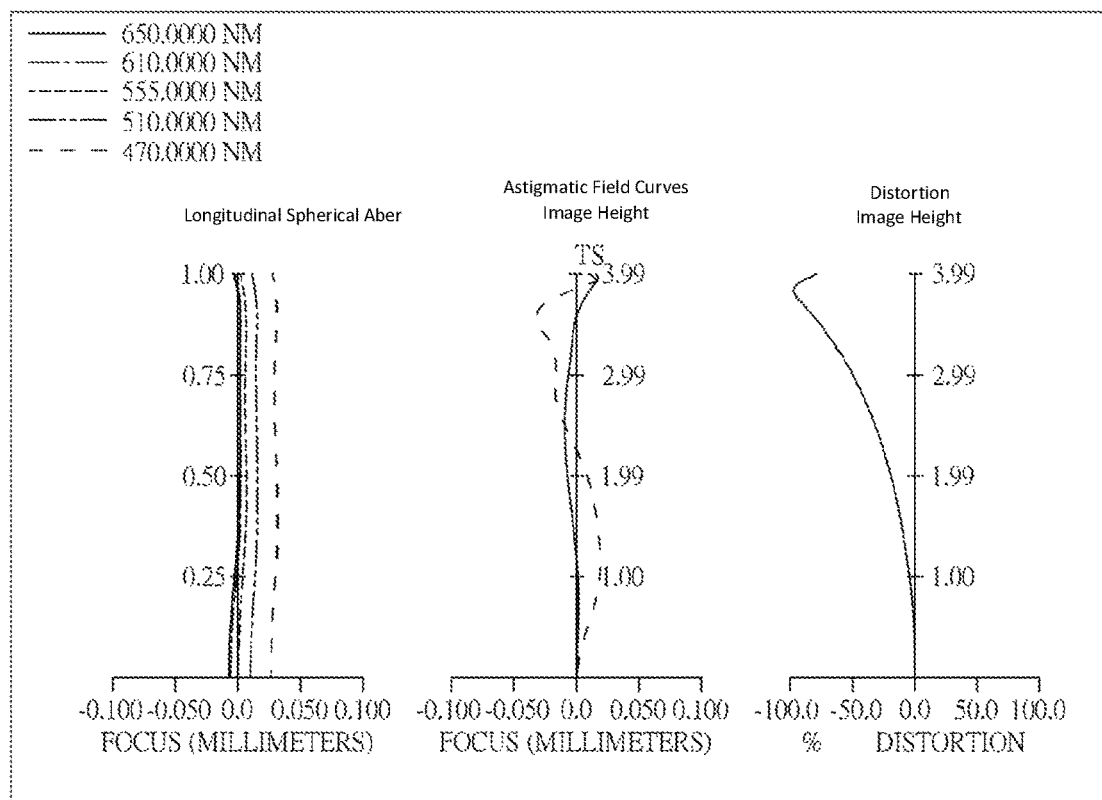
FIG. 4B shows curve diagrams of longitudinal spherical aberration, astigmatic field, and optical distortion of the optical image capturing system according to the third optical embodiment of the present application in order from left to right.

As shown in FIG. 4A and FIG. 4B, an optical image capturing system 30 of the third optical embodiment of the present invention includes, along an optical axis from an object side to an image side, a first lens 310, a second lens 320, a third lens 330, an aperture 300, a fourth lens 340, a fifth lens 350, a sixth lens 360, a seventh lens 370, an infrared rays filter 380, an image plane 390, and an image sensor 392.

The first lens 310 has negative refractive power and is made of glass. An object-side surface 312 thereof, which faces the object side, is a convex spherical surface, and an image-side surface 314 thereof, which faces the image side, is a concave spherical surface.

The second lens 320 has negative refractive power and is made of glass. An object-side surface 322 thereof, which faces the object side, is a concave spherical surface, and an image-side surface 324 thereof, which faces the image side, is a convex spherical surface.

The third lens 330 has positive refractive power and is made of plastic. An object-side surface 332 thereof, which faces the object side, is a convex aspheric surface, and an image-side surface 334 thereof, which faces the image side, is a convex aspheric surface. The image-side surface 334 has an inflection point.

The fourth lens 340 has negative refractive power and is made of plastic. An object-side surface 342, which faces the object side, is a concave aspheric surface, and an image-side surface 344, which faces the image side, is a concave aspheric surface. The image-side surface 344 has an inflection point.

The fifth lens 350 has positive refractive power and is made of plastic. An object-side surface 352, which faces the object side, is a convex aspheric surface, and an image-side surface 354, which faces the image side, is a convex aspheric surface.

The sixth lens 360 has negative refractive power and is made of plastic. An object-side surface 362, which faces the object side, is a convex aspheric surface, and an image-side surface 364, which faces the image side, is a concave aspheric surface. The object-side surface 362 has an inflection point, and the image-side surface 364 has an inflection point. It may help to shorten the back focal length to keep small in size. Whereby, the incident angle of each view field entering the sixth lens 360 could be effectively adjusted to improve aberration.

The infrared rays filter 380 is made of glass and is disposed between the sixth lens 360 and the image plane 390. The infrared rays filter 390 gives no contribution to the focal length of the optical image capturing system 30.

The parameters of the lenses of the third optical embodiment 30 are listed in Table 5 and Table 6.

TABLE 5 f = 2.808 mm; f/HEP = 1.6; HAF = 100 deg

| Surface | | Radius of curvature (mm) | Thickness (mm) | Material | Refractive index | Abbe number | Focal length (mm) |
|---|---|---|---|---|---|---|---|
| 0 | Object | 1E+18 | 1E+18 | | | | |
| 1 | 1st lens | 71.398124 | 7.214 | glass | 1.702 | 41.15 | −11.765 |
| 2 | | 7.117272355 | 5.788 | | | | |
| 3 | 2nd lens | −13.29213699 | 10.000 | glass | 2.003 | 19.32 | −4537.460 |
| 4 | | −18.37509887 | 7.005 | | | | |
| 5 | 3rd lens | 5.039114804 | 1.398 | plastic | 1.514 | 56.80 | 7.553 |
| 6 | | −15.53136631 | −0.140 | | | | |
| 7 | Aperture | 1E+18 | 2.378 | | | | |
| 8 | 4th lens | −18.68613609 | 0.577 | plastic | 1.661 | 20.40 | −4.978 |
| 9 | | 4.086545927 | 0.141 | | | | |
| 10 | 5th lens | 4.927609282 | 2.974 | plastic | 1.565 | 58.00 | 4.709 |
| 11 | | −4.551946605 | 1.389 | | | | |
| 12 | 6th lens | 9.184876531 | 1.916 | plastic | 1.514 | 56.80 | −23.405 |
| 13 | | 4.845500046 | 0.800 | | | | |
| 14 | Infrared rays filter | 1E+18 | 0.500 | BK_7 | 1.517 | 64.13 | |
| 15 | | 1E+18 | 0.371 | | | | |
| 16 | Image plane | 1E+18 | 0.005 | | | | |

Reference wavelength (d-line): 555 nm; the position of blocking light: none.

TABLE 6

Coefficients of the aspheric surfaces

| Surface | 1 | 2 | 3 | 4 | 5 | 6 | 8 |
|---|---|---|---|---|---|---|---|
| k | 0.000000E+00 | 0.000000E+00 | 0.000000E+00 | 0.000000E+00 | 1.318519E−01 | 3.120384E+00 | −1.494442E+01 |
| A4 | 0.000000E+00 | 0.000000E+00 | 0.000000E+00 | 0.000000E+00 | 6.405246E−05 | 2.103942E−03 | −1.598286E−03 |
| A6 | 0.000000E+00 | 0.000000E+00 | 0.000000E+00 | 0.000000E+00 | 2.278341E−05 | −1.050629E−04 | −9.177115E−04 |
| A8 | 0.000000E+00 | 0.000000E+00 | 0.000000E+00 | 0.000000E+00 | −3.672908E−06 | 6.168906E−06 | 1.011405E−04 |
| A10 | 0.000000E+00 | 0.000000E+00 | 0.000000E+00 | 0.000000E+00 | 3.748457E−07 | −1.224682E−07 | −4.919835E−06 |

| Surface | 9 | 10 | 11 | 12 | 13 |
|---|---|---|---|---|---|
| k | 2.744228E−02 | −7.864013E+00 | −2.263702E+00 | −4.206923E+01 | −7.030803E+00 |
| A4 | −7.291825E−03 | 1.405243E−04 | −3.919567E−03 | −1.679499E−03 | −2.640099E−03 |
| A6 | 9.730714E−05 | 1.837602E−04 | 2.683449E−03 | −3.518520E−04 | −4.507651E−05 |
| A8 | 1.101816E−06 | −2.173368E−05 | −1.229452E−05 | 5.047353E−05 | −2.600391E−05 |
| A10 | −6.849076E−07 | 7.328496E−07 | 4.222621E−07 | −3.851055E−06 | 1.161811E−06 |

An equation of the aspheric surfaces of the third optical embodiment is the same as that of the first optical embodiment, and the definitions are the same as well.

The exact parameters of the third optical embodiment based on Table 5 and Table 6 are listed in the following table:

| Third optical embodiment (Reference wavelength: 555 nm) | | | | | |
|---|---|---|---|---|---|
| \|f/f1\| | \|f/f2\| | \|f/f3\| | \|f/f4\| | \|f/f5\| | \|f/f6\| |
| 0.23865 | 0.00062 | 0.37172 | 0.56396 | 0.59621 | 0.11996 |
| ΣPPR | ΣNPR | ΣPPR/\|ΣNPR\| | IN12/f | IN56/f | TP4/(IN34 + TP4 + IN45) |
| 1.77054 | 0.12058 | 14.68400 | 2.06169 | 0.49464 | 0.19512 |
| \|f1/f2\| | \|f2/f3\| | (TP1 + IN12)/TP2 | | (TP6 + IN56)/TP5 | |
| 0.00259 | 600.74778 | 1.30023 | | 1.11131 | |
| HOS | InTL | HOS/HOI | InS/HOS | ODT % | TDT % |
| 42.31580 | 40.63970 | 10.57895 | 0.26115 | −122.32700 | 93.33510 |

-continued

| Third optical embodiment (Reference wavelength: 555 nm) | | | | | |
|---|---|---|---|---|---|
| HVT51 | HVT52 | HVT61 | HVT62 | HVT62/HOI | HVT62/HOS |
| 0 | 0 | 2.22299 | 2.60561 | 0.65140 | 0.06158 |
| TP2/TP3 | TP3/TP4 | InRS61 | InRS62 | \|InRS61\|/TP6 | \|InRS62\|/TP6 |
| 7.15374 | 2.42321 | −0.20807 | −0.24978 | 0.10861 | 0.13038 |
| PhiA | | | | | HOI |
| 6.150 mm | | | | | 4 mm |
| | | | | | InTL/HOS |
| | | | | | 0.9604 |
| PSTA | PLTA | NSTA | NLTA | SSTA | SLTA |
| 0.014 mm | 0.002 mm | −0.003 mm | −0.002 mm | 0.011 mm | −0.001 mm |

The figures related to the profile curve lengths obtained based on Table 5 and Table 6 are listed in the following table:

| Third optical embodiment (Reference wavelength: 555 nm) | | | | | | |
|---|---|---|---|---|---|---|
| ARE | 1/2(HEP) | ARE value | ARE−1/2(HEP) | 2(ARE/HEP) % | TP | ARE/TP (%) |
| 11 | 0.877 | 0.877 | −0.00036 | 99.96% | 7.214 | 12.16% |
| 12 | 0.877 | 0.879 | 0.00186 | 100.21% | 7.214 | 12.19% |
| 21 | 0.877 | 0.878 | 0.00026 | 100.03% | 10.000 | 8.78% |
| 22 | 0.877 | 0.877 | −0.00004 | 100.00% | 10.000 | 8.77% |
| 31 | 0.877 | 0.882 | 0.00413 | 100.47% | 1.398 | 63.06% |
| 32 | 0.877 | 0.877 | 0.00004 | 100.00% | 1.398 | 62.77% |
| 41 | 0.877 | 0.877 | −0.00001 | 100.00% | 0.577 | 152.09% |
| 42 | 0.877 | 0.883 | 0.00579 | 100.66% | 0.577 | 153.10% |
| 51 | 0.877 | 0.881 | 0.00373 | 100.43% | 2.974 | 29.63% |
| 52 | 0.877 | 0.883 | 0.00521 | 100.59% | 2.974 | 29.68% |
| 61 | 0.877 | 0.878 | 0.00064 | 100.07% | 1.916 | 45.83% |
| 62 | 0.877 | 0.881 | 0.00368 | 100.42% | 1.916 | 45.99% |
| ARS | EHD | ARS value | ARS−EHD | (ARS/EHD) % | TP | ARS/TP (%) |
| 11 | 17.443 | 17.620 | 0.178 | 101.02% | 7.214 | 244.25% |
| 12 | 6.428 | 8.019 | 1.592 | 124.76% | 7.214 | 111.16% |
| 21 | 6.318 | 6.584 | 0.266 | 104.20% | 10.000 | 65.84% |
| 22 | 6.340 | 6.472 | 0.132 | 102.08% | 10.000 | 64.72% |
| 31 | 2.699 | 2.857 | 0.158 | 105.84% | 1.398 | 204.38% |
| 32 | 2.476 | 2.481 | 0.005 | 100.18% | 1.398 | 177.46% |
| 41 | 2.601 | 2.652 | 0.051 | 101.96% | 0.577 | 459.78% |
| 42 | 3.006 | 3.119 | 0.113 | 103.75% | 0.577 | 540.61% |
| 51 | 3.075 | 3.171 | 0.096 | 103.13% | 2.974 | 106.65% |
| 52 | 3.317 | 3.624 | 0.307 | 109.24% | 2.974 | 121.88% |
| 61 | 3.331 | 3.427 | 0.095 | 102.86% | 1.916 | 178.88% |
| 62 | 3.944 | 4.160 | 0.215 | 105.46% | 1.916 | 217.14% |

The results of the equations of the third optical embodiment based on Table 5 and Table 6 are listed in the following table:

| Values related to the inflection points of the third optical embodiment (Reference wavelength: 555 nm) | | | | | | | |
|---|---|---|---|---|---|---|---|
| HIF321 | 2.0367 | HIF321/HOI | 0.5092 | SGI321 | −0.1056 | \|SGI321\|/(\|SGI321\| + TP3) | 0.0702 |
| HIF421 | 2.4635 | HIF421/HOI | 0.6159 | SGI421 | 0.5780 | \|SGI421\|/(\|SGI421\| + TP4) | 0.5005 |
| HIF611 | 1.2364 | HIF611/HOI | 0.3091 | SGI611 | 0.0668 | \|SGI611\|/(\|SGI611\| + TP6) | 0.0337 |
| HIF621 | 1.5488 | HIF621/HOI | 0.3872 | SGI621 | 0.2014 | \|SGI621\|/(\|SGI621\| + TP6) | 0.0951 |

Fourth Optical Embodiment

Figure 5A:
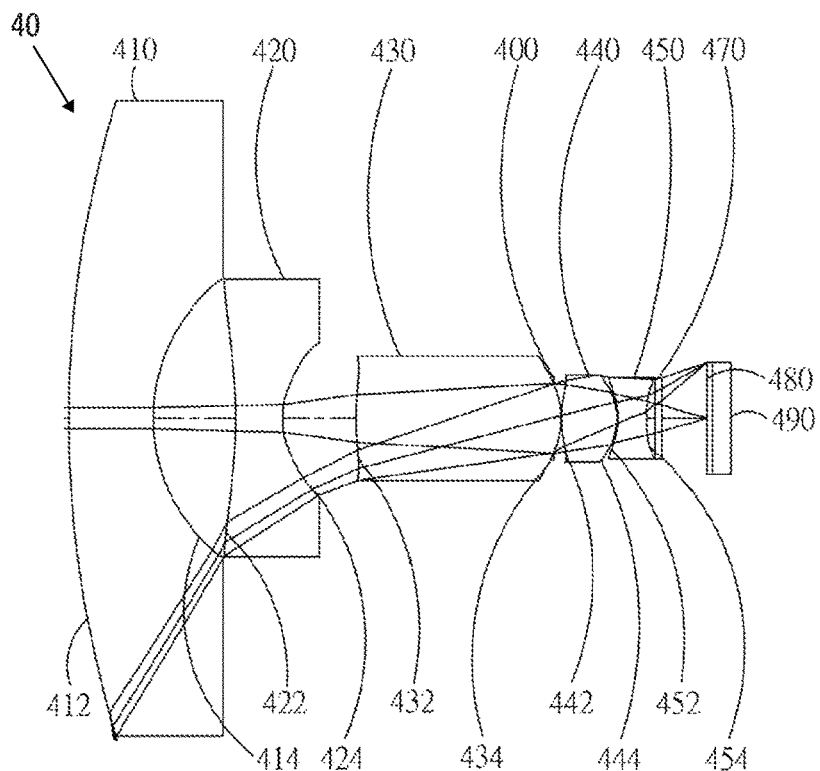
FIG. 5A is a schematic diagram showing a fourth optical embodiment of the present invention.
Figure 5B:
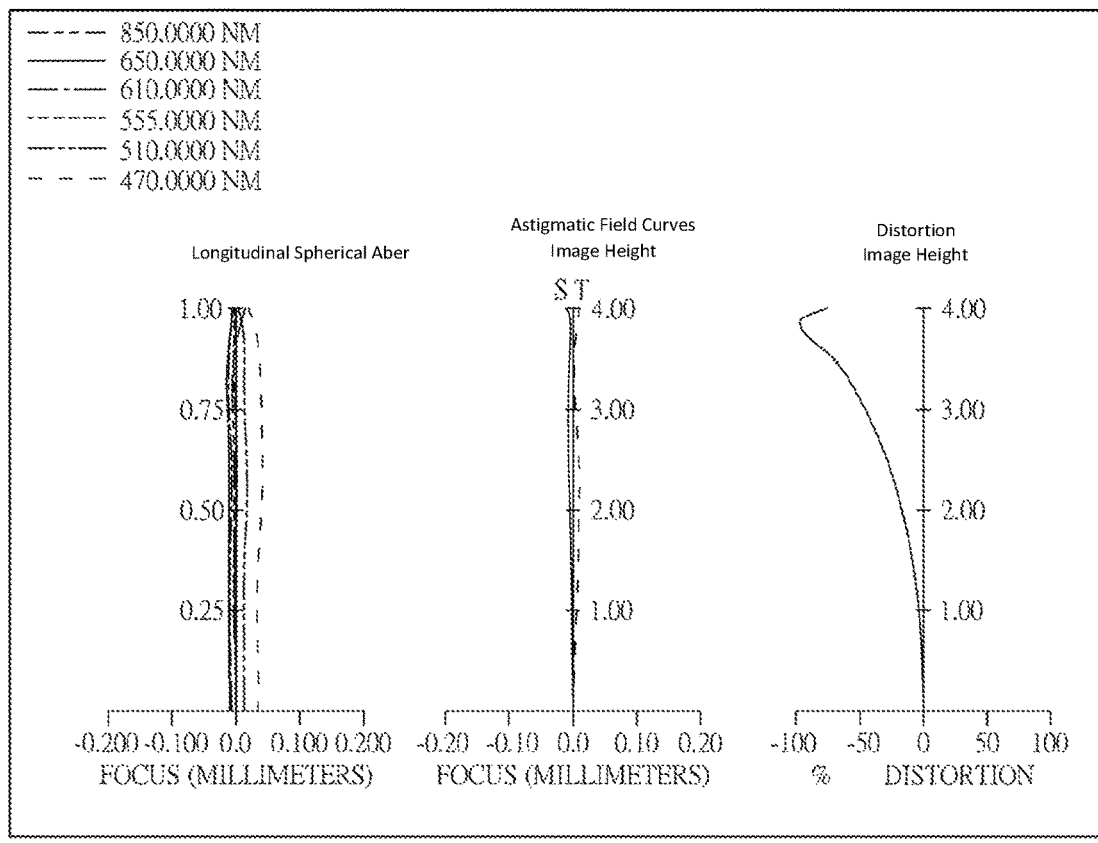
FIG. 5B shows curve diagrams of longitudinal spherical aberration, astigmatic field, and optical distortion of the optical image capturing system according to the fourth optical embodiment of the present application in order from left to right.

As shown in FIG. 5A and FIG. 5B, an optical image capturing system 40 of the fourth optical embodiment of the present invention includes, along an optical axis from an object side to an image side, a first lens 410, a second lens 420, a third lens 430, an aperture 400, a fourth lens 440, a fifth lens 450, an infrared rays filter 480, an image plane 490, and an image sensor 492.

The first lens 410 has negative refractive power and is made of glass. An object-side surface 412 thereof, which faces the object side, is a convex spherical surface, and an image-side surface 414 thereof, which faces the image side, is a concave spherical surface.

The second lens 420 has negative refractive power and is made of plastic. An object-side surface 422 thereof, which faces the object side, is a concave aspheric surface, and an image-side surface 424 thereof, which faces the image side, is a concave aspheric surface. The object-side surface 422 has an inflection point.

The third lens 430 has positive refractive power and is made of plastic. An object-side surface 432 thereof, which faces the object side, is a convex aspheric surface, and an image-side surface 434 thereof, which faces the image side, is a convex aspheric surface. The object-side surface 432 has an inflection point.

The fourth lens 440 has positive refractive power and is made of plastic. An object-side surface 442, which faces the object side, is a convex aspheric surface, and an image-side surface 444, which faces the image side, is a convex aspheric surface. The object-side surface 442 has an inflection point.

The fifth lens 450 has negative refractive power and is made of plastic. An object-side surface 452, which faces the object side, is a concave aspheric surface, and an image-side surface 454, which faces the image side, is a concave aspheric surface. The object-side surface 452 has two inflection points. It may help to shorten the back focal length to keep small in size.

The infrared rays filter 480 is made of glass and is disposed between the fifth lens 450 and the image plane 490. The infrared rays filter 480 gives no contribution to the focal length of the optical image capturing system 40.

The parameters of the lenses of the fourth optical embodiment are listed in Table 7 and Table 8.

TABLE 7 f = 2.7883 mm; f/HEP = 1.8; HAF = 101 deg

| Surface | | Radius of curvature (mm) | Thickness (mm) | Material | Refractive index | Abbe number | Focal length (mm) |
|---|---|---|---|---|---|---|---|
| 0 | Object | 1E+18 | 1E+18 | | | | |
| 1 | 1$^{st}$ lens | 76.84219 | 6.117399 | glass | 1.497 | 81.61 | −31.322 |
| 2 | | 12.62555 | 5.924382 | | | | |
| 3 | 2$^{nd}$ lens | −37.0327 | 3.429817 | plastic | 1.565 | 54.5 | −8.70843 |
| 4 | | 5.88556 | 5.305191 | | | | |
| 5 | 3$^{rd}$ lens | 17.99395 | 14.79391 | | | | |
| 6 | | −5.76903 | −0.4855 | plastic | 1.565 | 58 | 9.94787 |
| 7 | Aperture | 1E+18 | 0.535498 | | | | |
| 8 | 4$^{th}$ lens | 8.19404 | 4.011739 | plastic | 1.565 | 58 | 5.24898 |
| 9 | | −3.84363 | 0.050366 | | | | |
| 10 | 5$^{th}$ lens | −4.34991 | 2.088275 | plastic | 1.661 | 20.4 | −4.97515 |
| 11 | | 16.6609 | 0.6 | | | | |
| 12 | Infrared rays filter | 1E+18 | 0.5 | BK_7 | 1.517 | 64.13 | |
| 13 | | 1E+18 | 3.254927 | | | | |
| 14 | Image plane | 1E+18 | −0.00013 | | | | |

Reference wavelength (d-line): 555 nm.

TABLE 8

Coefficients of the aspheric surfaces

| Surface | 1 | 2 | 3 | 4 | 5 | 6 |
|---|---|---|---|---|---|---|
| k | 0.000000E+00 | 0.000000E+00 | 0.131249 | −0.069541 | −0.324555 | 0.009216 |
| A4 | 0.000000E+00 | 0.000000E+00 | 3.99823E−05 | −8.55712E−04 | −9.07093E−04 | 8.80963E−04 |
| A6 | 0.000000E+00 | 0.000000E+00 | 9.03636E−08 | −1.96175E−06 | −1.02465E−05 | 3.14497E−05 |
| A8 | 0.000000E+00 | 0.000000E+00 | 1.91025E−09 | −1.39344E−08 | −8.18157E−08 | −3.15863E−06 |
| A10 | 0.000000E+00 | 0.000000E+00 | −1.18567E−11 | −4.17090E−09 | −2.42621E−09 | 1.44613E−07 |
| A12 | 0.000000E+00 | 0.000000E+00 | 0.000000E+00 | 0.000000E+00 | 0.000000E+00 | 0.000000E+00 |

| Surface | 8 | 9 | 10 | 11 |
|---|---|---|---|---|
| k | −0.292346 | −0.18604 | −6.17195 | 27.541383 |
| A4 | −1.02138E−03 | 4.33629E−03 | 1.58379E−03 | 7.56932E−03 |
| A6 | −1.18559E−04 | −2.91588E−04 | −1.81549E−04 | −7.83858E−04 |
| A8 | 1.34404E−05 | 9.11419E−06 | −1.18213E−05 | 4.79120E−05 |
| A10 | −2.80681E−06 | 1.28365E−07 | 1.92716E−06 | −1.73591E−06 |
| A12 | 0.000000E+00 | 0.000000E+00 | 0.000000E+00 | 0.000000E+00 |

An equation of the aspheric surfaces of the fourth optical embodiment is the same as that of the first optical embodiment, and the definitions are the same as well.

The exact parameters of the fourth optical embodiment based on Table 7 and Table 8 are listed in the following table:

| Fourth optical embodiment (Reference wavelength: 555 nm) | | | | | |
|---|---|---|---|---|---|
| \|f/f1\| | \|f/f2\| | \|f/f3\| | \|f/f4\| | \|f/f5\| | \|f1/f2\| |
| 0.08902 | 0.32019 | 0.28029 | 0.53121 | 0.56045 | 3.59674 |
| ΣPPR | ΣNPR | ΣPPR/\|ΣNPR\| | IN12/f | IN45/f | \|f2/f3\| |
| 1.4118 | 0.3693 | 3.8229 | 2.1247 | 0.0181 | 0.8754 |
| TP3/(IN23 + TP3 + IN34) | | (TP1 + IN12)/TP2 | | (TP5 + IN45)/TP4 | |
| 0.73422 | | 3.51091 | | 0.53309 | |
| HOS | InTL | HOS/HOI | InS/HOS | ODT % | TDT % |
| 46.12590 | 41.77110 | 11.53148 | 0.23936 | −125.266 | 99.1671 |
| HVT41 | HVT42 | HVT51 | HVT52 | HVT52/HOI | HVT52/HOS |
| 0.00000 | 0.00000 | 0.00000 | 0.00000 | 0.00000 | 0.00000 |
| TP2/TP3 | TP3/TP4 | InRS51 | InRS52 | \|InRS51\|/TP5 | \|InRS52\|/TP5 |
| 0.23184 | 3.68765 | −0.679265 | 0.5369 | 0.32528 | 0.25710 |
| PhiA | | | | | HOI |
| 5.598 mm | | | | | 4 mm |
| | | | | | InTL/HOS |
| | | | | | 0.9056 |
| PSTA | PLTA | NSTA | NLTA | SSTA | SLTA |
| −0.011 mm | 0.005 mm | −0.010 mm | −0.003 mm | 0.005 mm | −0.00026 mm |

The figures related to the profile curve lengths obtained based on Table 7 and Table 8 are listed in the following table:

| Fourth optical embodiment (Reference wavelength: 555 nm) | | | | | | |
|---|---|---|---|---|---|---|
| ARE | 1/2(HEP) | ARE value | ARE-1/2(HEP) | 2(ARE/HEP) % | TP | ARE/TP (%) |
| 11 | 0.775 | 0.774 | −0.00052 | 99.93% | 6.117 | 12.65% |
| 12 | 0.775 | 0.774 | −0.00005 | 99.99% | 6.117 | 12.66% |
| 21 | 0.775 | 0.774 | −0.00048 | 99.94% | 3.430 | 22.57% |
| 22 | 0.775 | 0.776 | 0.00168 | 100.22% | 3.430 | 22.63% |
| 31 | 0.775 | 0.774 | −0.00031 | 99.96% | 14.794 | 5.23% |
| 32 | 0.775 | 0.776 | 0.00177 | 100.23% | 14.794 | 5.25% |
| 41 | 0.775 | 0.775 | 0.00059 | 100.08% | 4.012 | 19.32% |
| 42 | 0.775 | 0.779 | 0.00453 | 100.59% | 4.012 | 19.42% |
| 51 | 0.775 | 0.778 | 0.00311 | 100.40% | 2.088 | 37.24% |
| 52 | 0.775 | 0.774 | −0.00014 | 99.98% | 2.088 | 37.08% |
| ARS | EHD | ARS value | ARS-EHD | (ARS/EHD) % | TP | ARS/TP (%) |
| 11 | 23.038 | 23.397 | 0.359 | 101.56% | 6.117 | 382.46% |
| 12 | 10.140 | 11.772 | 1.632 | 116.10% | 6.117 | 192.44% |
| 21 | 10.138 | 10.178 | 0.039 | 100.39% | 3.430 | 296.74% |
| 22 | 5.537 | 6.337 | 0.800 | 114.44% | 3.430 | 184.76% |
| 31 | 4.490 | 4.502 | 0.012 | 100.27% | 14.794 | 30.43% |
| 32 | 2.544 | 2.620 | 0.076 | 102.97% | 14.794 | 17.71% |
| 41 | 2.735 | 2.759 | 0.024 | 100.89% | 4.012 | 68.77% |
| 42 | 3.123 | 3.449 | 0.326 | 110.43% | 4.012 | 85.97% |
| 51 | 2.934 | 3.023 | 0.089 | 103.04% | 2.088 | 144.74% |
| 52 | 2.799 | 2.883 | 0.084 | 103.00% | 2.088 | 138.08% |

The results of the equations of the fourth optical embodiment based on Table 7 and Table 8 are listed in the following table:

| Values related to the inflection points of the fourth optical embodiment (Reference wavelength: 555 nm) | | | | | | |
|---|---|---|---|---|---|---|
| HIF211 | 6.3902 | HIF211/HOI | 1.5976 | SGI211 | −0.4793 | \|SGI211\|/(\|SGI2111 + TP2) | 0.1226 |
| HIF311 | 2.1324 | HIF311/HOI | 0.5331 | SGI311 | 0.1069 | \|SGI311\|/(\|SGI3111 + TP3) | 0.0072 |
| HIF411 | 2.0278 | HIF411/HOI | 0.5070 | SGI411 | 0.2287 | \|SGI411\|/(\|SGI4111 + TP4) | 0.0539 |
| HIF511 | 2.6253 | HIF511/HOI | 0.6563 | SGI511 | −0.5681 | \|SGI511\|/(\|SGI5111 + TP5) | 0.2139 |
| HIF512 | 2.1521 | HIF512/HOI | 0.5380 | SGI512 | −0.8314 | \|SGI512\|/(\|SGI5121 + TP5) | 0.2848 |

Fifth Optical Embodiment

Figure 6A:
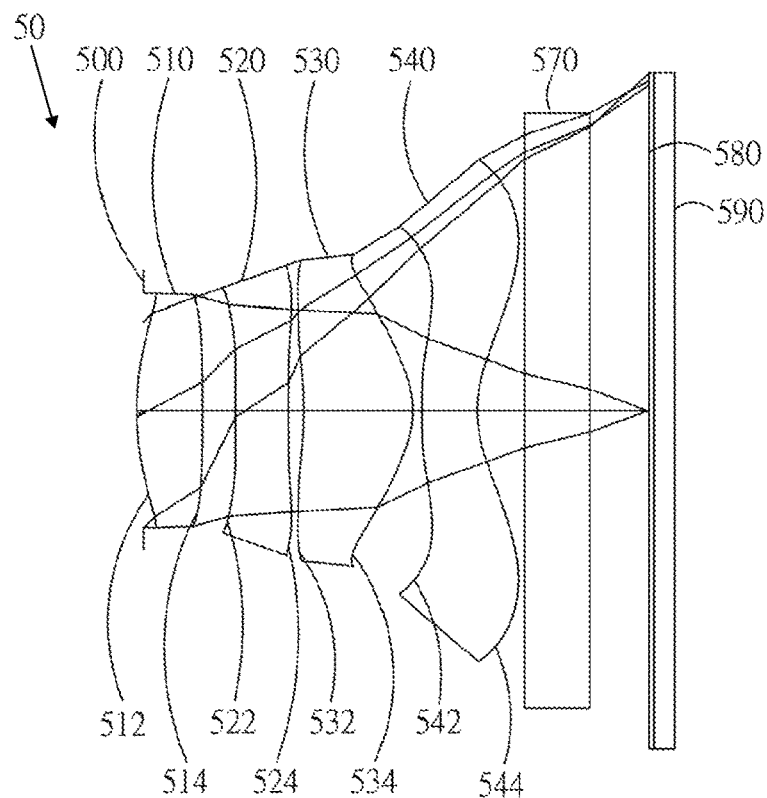
FIG. 6A is a schematic diagram showing a fifth optical embodiment of the present invention.
Figure 6B:
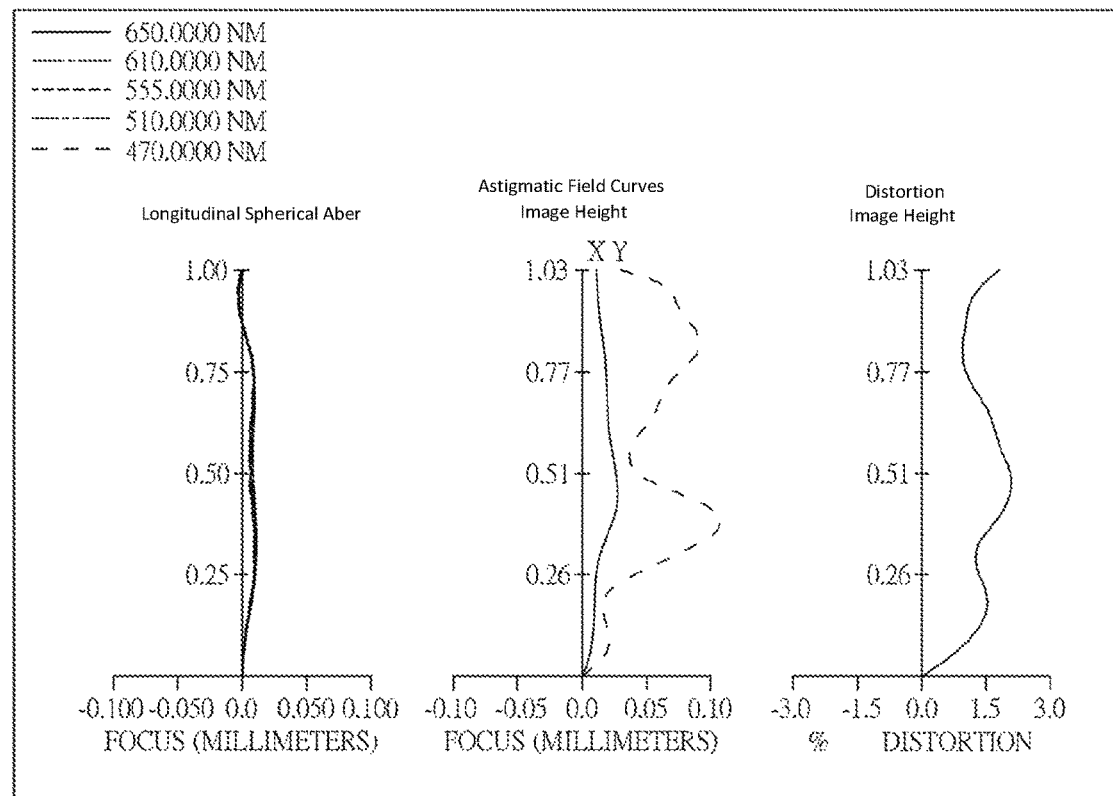
FIG. 6B shows curve diagrams of longitudinal spherical aberration, astigmatic field, and optical distortion of the optical image capturing system according to the fifth optical embodiment of the present application in order from left to right.

As shown in FIG. 6A and FIG. 6B, an optical image capturing system 50 of the fifth optical embodiment of the present invention includes, along an optical axis from an object side to an image side, an aperture 500, a first lens 510, a second lens 520, a third lens 530, a fourth lens 540, an infrared rays filter 570, an image plane 580, and an image sensor 590.

The first lens 510 has positive refractive power and is made of plastic. An object-side surface 512, which faces the object side, is a convex aspheric surface, and an image-side surface 514, which faces the image side, is a convex aspheric surface. The object-side surface 512 has an inflection point.

The second lens 520 has negative refractive power and is made of plastic. An object-side surface 522 thereof, which faces the object side, is a convex aspheric surface, and an image-side surface 524 thereof, which faces the image side, is a concave aspheric surface. The object-side surface 522 has two inflection points, and the image-side surface 524 has an inflection point.

The third lens 530 has positive refractive power and is made of plastic. An object-side surface 532, which faces the object side, is a concave aspheric surface, and an image-side surface 534, which faces the image side, is a convex aspheric surface. The object-side surface 532 has three inflection points, and the image-side surface 534 has an inflection point.

The fourth lens 540 has negative refractive power and is made of plastic. An object-side surface 542, which faces the object side, is a concave aspheric surface, and an image-side surface 544, which faces the image side, is a concave aspheric surface. The object-side surface 542 has two inflection points, and the image-side surface 544 has an inflection point.

The infrared rays filter 570 is made of glass and is disposed between the fourth lens 540 and the image plane 580. The infrared rays filter 570 gives no contribution to the focal length of the optical image capturing system 50.

The parameters of the lenses of the fifth optical embodiment are listed in Table 9 and Table 10.

TABLE 9

| f = 1.04102 mm; f/HEP = 1.4; HAF = 44.0346 deg | | | | | | | |
|---|---|---|---|---|---|---|---|
| Surface | | Radius of curvature (mm) | Thickness (mm) | Material | Refractive index | Abbe number | Focal length (mm) |
| 0 | Object | 1E+18 | 600 | | | | |
| 1 | Aperture | 1E+18 | −0.020 | | | | |
| 2 | 1st lens | 0.890166851 | 0.210 | plastic | 1.545 | 55.96 | 1.587 |
| 3 | | −29.11040115 | −0.010 | | | | |
| 4 | | 1E+18 | 0.116 | | | | |
| 5 | 2nd lens | 10.67765398 | 0.170 | plastic | 1.642 | 22.46 | −14.569 |
| 6 | | 4.977771922 | 0.049 | | | | |
| 7 | 3rd lens | −1.191436932 | 0.349 | plastic | 1.545 | 55.96 | 0.510 |
| 8 | | −0.248990674 | 0.030 | | | | |
| 9 | 4th lens | −38.08537212 | 0.176 | plastic | 1.642 | 22.46 | −0.569 |
| 10 | | 0.372574476 | 0.152 | | | | |
| 11 | | 1E+18 | 0.210 | BK_7 | 1.517 | 64.13 | 1E+18 |
| 12 | | 1E+18 | 0.185 | | | | 1E+18 |
| 13 | | 1E+18 | 0.005 | | | | 1E+18 |

Reference wavelength (d-line): 555 nm; the position of blocking light: the effective radius of the clear aperture of the fourth surface is 0.360 mm.

TABLE 10

| Coefficients of the aspheric surfaces | | | | | |
|---|---|---|---|---|---|
| Surface | 2 | 3 | 5 | 6 | 7 |
| k | −1.106629E+00 | 2.994179E−07 | −7.78875E+01 | −3.440335E+01 | −8.522097E−01 |
| A4 | 8.291155E−01 | −6.401113E−01 | −4.958114E+00 | −1.875957E+00 | −4.878227E−01 |
| A6 | −2.398799E+01 | −1.265726E+01 | 1.299769E+02 | 8.568480E+01 | 1.291242E+02 |
| A8 | 1.825378E+02 | 8.457286E+01 | −2.736977E+03 | −1.279044E+03 | −1.979689E+03 |
| A10 | −6.211133E+02 | −2.157875E+02 | 2.908537E+04 | 8.661312E+03 | 1.456076E+04 |

TABLE 10-continued

| Coefficients of the aspheric surfaces | | | | | |
|---|---|---|---|---|---|
| A12 | -4.719066E+02 | -6.203600E+02 | -1.499597E+05 | -2.875274E+04 | -5.975920E+04 |
| A14 | 0.000000E+00 | 0.000000E+00 | 2.992026E+05 | 3.764871E+04 | 1.351676E+05 |
| A16 | 0.000000E+00 | 0.000000E+00 | 0.000000E+00 | 0.000000E+00 | -1.329001E+05 |
| A18 | 0.000000E+00 | 0.000000E+00 | 0.000000E+00 | 0.000000E+00 | 0.000000E+00 |
| A20 | 0.000000E+00 | 0.000000E+00 | 0.000000E+00 | 0.000000E+00 | 0.000000E+00 |

| Surface | 8 | 9 | 10 |
|---|---|---|---|
| k | -4.735945E+00 | -2.277155E+01 | -8.039778E-01 |
| A4 | -2.490377E+00 | 1.672704E+01 | -7.613206E+00 |
| A6 | 1.524149E+02 | -3.260722E+02 | 3.374046E+01 |
| A8 | -4.841033E+03 | 3.373231E+03 | -1.368453E+02 |
| A10 | 8.053747E+04 | -2.177676E+04 | 4.049486E+02 |
| A12 | -7.936887E+05 | 8.951687E+04 | -9.711797E+02 |
| A14 | 4.811528E+06 | -2.363737E+05 | 1.942574E+03 |
| A16 | -1.762293E+07 | 3.983151E+05 | -2.876356E+03 |
| A18 | 3.579891E+07 | -4.090689E+05 | 2.562386E+03 |
| A20 | -3.094006E+07 | 2.056724E+05 | -9.943657E+02 |

An equation of the aspheric surfaces of the fifth optical embodiment is the same as that of the first optical embodiment, and the definitions are the same as well.

The exact parameters of the fifth optical embodiment based on Table 9 and Table 10 are listed in the following table:

| Fifth optical embodiment (Reference wavelength: 555 nm) | | | | | |
|---|---|---|---|---|---|
| InRS41 | InRS42 | HVT41 | HVT42 | ODT % | TDT % |
| -0.07431 | 0.00475 | 0.00000 | 0.53450 | 2.09403 | 0.84704 |
| $|f/f1|$ | $|f/f2|$ | $|f/f3|$ | $|f/f4|$ | $|f1/f2|$ | $|f2/f3|$ |
| 0.65616 | 0.07145 | 2.04129 | 1.83056 | 0.10890 | 28.56826 |
| ΣPPR | ΣNPR | ΣPPR/|ΣNPR| | ΣPP | ΣNP | f1/ΣPP |
| 2.11274 | 2.48672 | 0.84961 | -14.05932 | 1.01785 | 1.03627 |
| f4/ΣNP | IN12/f | IN23/f | IN34/f | TP3/f | TP4/f |
| 1.55872 | 0.10215 | 0.04697 | 0.02882 | 0.33567 | 0.16952 |
| InTL | HOS | HOS/HOI | InS/HOS | InTL/HOS | ΣTP/InTL |
| 1.09131 | 1.64329 | 1.59853 | 0.98783 | 0.66410 | 0.83025 |
| (TP1 + IN12)/TP2 | (TP4 + IN34)/TP3 | TP1/TP2 | TP3/TP4 | IN23/(TP2 + IN23 + TP3) | |
| 1.86168 | 0.59088 | 1.23615 | 1.98009 | 0.08604 | |
| |InRS41|/TP4 | |InRS42|/TP4 | HVT42/HOI | HVT42/HOS | InTL/HOS | |
| 0.4211 | 0.0269 | 0.5199 | 0.3253 | 0.6641 | |
| PhiA | | | | | HOI |
| 1.596 mm | | | | | 1.028 mm |
| PSTA | PLTA | NSTA | NLTA | SSTA | SLTA |
| -0.029 mm | -0.023 mm | -0.011 mm | -0.024 mm | 0.010 mm | 0.011 mm |

The results of the equations of the fifth optical embodiment based on Table 9 and Table 10 are listed in the following table:

Values related to the inflection points of the fifth optical embodiment (Reference wavelength: 555 nm)

| | | | | | | | |
|---|---|---|---|---|---|---|---|
| HIF111 | 0.28454 | HIF111/HOI | 0.27679 | SGI111 | 0.04361 | \|SGI111\|/(\|SGI111\| + TP1) | 0.17184 |
| HIF211 | 0.04198 | HIF211/HOI | 0.04083 | SGI211 | 0.00007 | \|SGI211\|/(\|SGI211\| + TP2) | 0.00040 |
| HIF212 | 0.37903 | HIF212/HOI | 0.36871 | SGI212 | −0.03682 | \|SGI212\|/(\|SGI212\| + TP2) | 0.17801 |
| HIF221 | 0.25058 | HIF221/HOI | 0.24376 | SGI221 | 0.00695 | \|SGI221\|/(\|SGI221\| + TP2) | 0.03927 |
| HIF311 | 0.14881 | HIF311/HOI | 0.14476 | SGI311 | −0.00854 | \|SGI311\|/(\|SGI311\| + TP3) | 0.02386 |
| HIF312 | 0.31992 | HIF312/HOI | 0.31120 | SGI312 | −0.01783 | \|SGI312\|/(\|SGI312\| + TP3) | 0.04855 |
| HIF313 | 0.32956 | HIF313/HOI | 0.32058 | SGI313 | −0.01801 | \|SGI313\|/(\|SGI313\| + TP3) | 0.04902 |
| HIF321 | 0.36943 | HIF321/HOI | 0.35937 | SGI321 | −0.14878 | \|SGI321\|/(\|SGI321\| + TP3) | 0.29862 |
| HIF411 | 0.01147 | HIF411/HOI | 0.01116 | SGI411 | −0.00000 | \|SGI411\|/(\|SGI411\| + TP4) | 0.00001 |
| HIF412 | 0.22405 | HIF412/HOI | 0.21795 | SGI412 | 0.01598 | \|SGI412\|/(\|SGI412\| + TP4) | 0.08304 |
| HIF421 | 0.24105 | HIF421/HOI | 0.23448 | SGI421 | 0.05924 | \|SGI421\|/(\|SGI421\| + TP4) | 0.25131 |

The figures related to the profile curve lengths obtained based on Table 9 and Table 10 are listed in the following table:

Fifth optical embodiment (Reference wavelength: 555 nm)

| ARE | 1/2(HEP) | ARE value | ARE-1/2(HEP) | 2(ARE/HEP) % | TP | ARE/TP (%) |
|---|---|---|---|---|---|---|
| 11 | 0.368 | 0.374 | 0.00578 | 101.57% | 0.210 | 178.10% |
| 12 | 0.366 | 0.368 | 0.00240 | 100.66% | 0.210 | 175.11% |
| 21 | 0.372 | 0.375 | 0.00267 | 100.72% | 0.170 | 220.31% |
| 22 | 0.372 | 0.371 | −0.00060 | 99.84% | 0.170 | 218.39% |
| 31 | 0.372 | 0.372 | −0.00023 | 99.94% | 0.349 | 106.35% |
| 32 | 0.372 | 0.404 | 0.03219 | 108.66% | 0.349 | 115.63% |
| 41 | 0.372 | 0.373 | 0.00112 | 100.30% | 0.176 | 211.35% |
| 42 | 0.372 | 0.387 | 0.01533 | 104.12% | 0.176 | 219.40% |

| ARS | EHD | ARS value | ARS-EHD | (ARS/EHD) % | TP | ARS/TP (%) |
|---|---|---|---|---|---|---|
| 11 | 0.368 | 0.374 | 0.00578 | 101.57% | 0.210 | 178.10% |
| 12 | 0.366 | 0.368 | 0.00240 | 100.66% | 0.210 | 175.11% |
| 21 | 0.387 | 0.391 | 0.00383 | 100.99% | 0.170 | 229.73% |
| 22 | 0.458 | 0.460 | 0.00202 | 100.44% | 0.170 | 270.73% |
| 31 | 0.476 | 0.478 | 0.00161 | 100.34% | 0.349 | 136.76% |
| 32 | 0.494 | 0.538 | 0.04435 | 108.98% | 0.349 | 154.02% |
| 41 | 0.585 | 0.624 | 0.03890 | 106.65% | 0.176 | 353.34% |
| 42 | 0.798 | 0.866 | 0.06775 | 108.49% | 0.176 | 490.68% |

Sixth Optical Embodiment

Figure 7A:
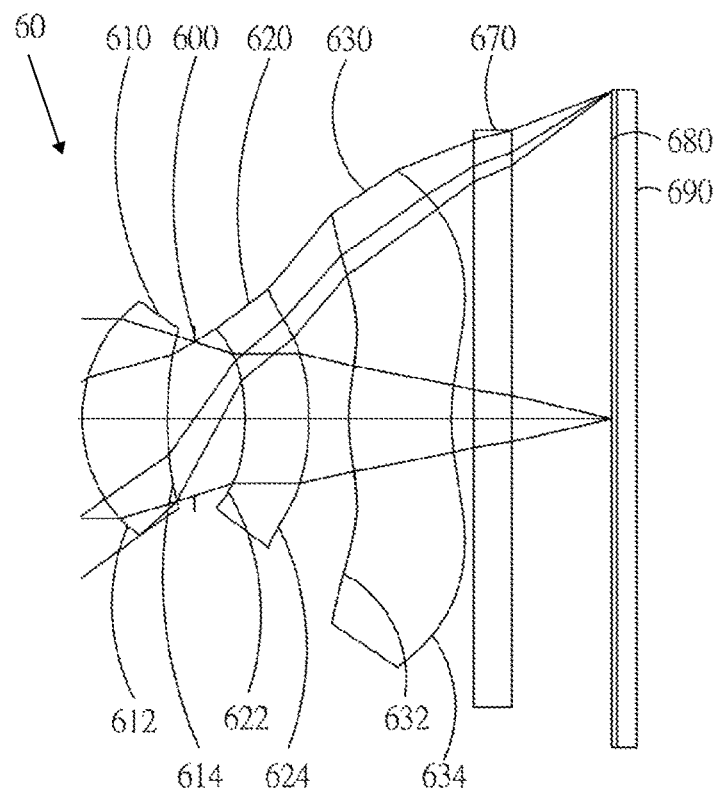
FIG. 7A is a schematic diagram showing a sixth optical embodiment of the present invention.
Figure 7B:
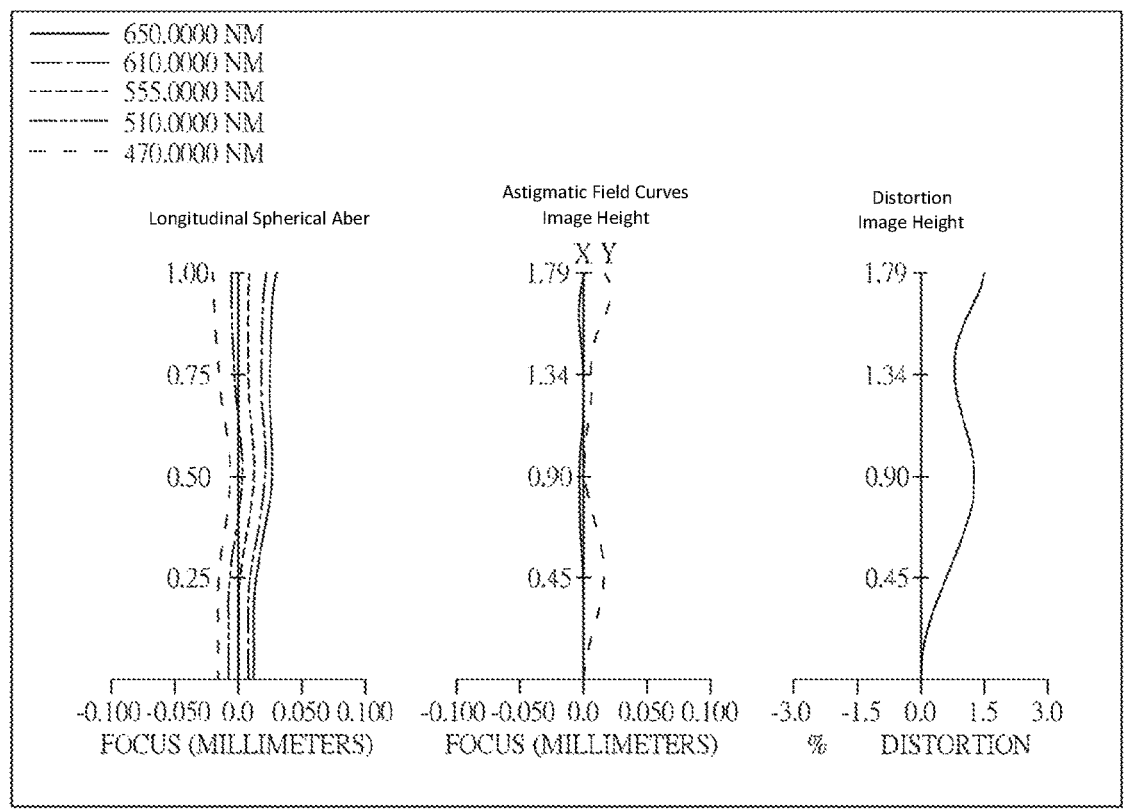
FIG. 7B shows curve diagrams of longitudinal spherical aberration, astigmatic field, and optical distortion of the optical image capturing system according to the sixth optical embodiment of the present application in order from left to right.

As shown in FIG. 7A and FIG. 7B, an optical image capturing system 60 of the sixth optical embodiment of the present invention includes, along an optical axis from an object side to an image side, a first lens 610, an aperture 600, a second lens 620, a third lens 630, an infrared rays filter 670, an image plane 680, and an image sensor 690.

The first lens 610 has positive refractive power and is made of plastic. An object-side surface 612, which faces the object side, is a convex aspheric surface, and an image-side surface 614, which faces the image side, is a concave aspheric surface.

The second lens 620 has negative refractive power and is made of plastic. An object-side surface 622 thereof, which faces the object side, is a concave aspheric surface, and an image-side surface 624 thereof, which faces the image side, is a convex aspheric surface. The image-side surface 624 has an inflection point.

The third lens 630 has positive refractive power and is made of plastic. An object-side surface 632, which faces the object side, is a convex aspheric surface, and an image-side surface 634, which faces the image side, is a concave aspheric surface. The object-side surface 632 has two inflection points, and the image-side surface 634 has an inflection point.

The infrared rays filter 670 is made of glass and is disposed between the third lens 630 and the image plane 680. The infrared rays filter 670 gives no contribution to the focal length of the optical image capturing system 60.

The parameters of the lenses of the sixth optical embodiment are listed in Table 11 and Table 12.

TABLE 11 f = 2.41135 mm; f/HEP = 2.22; HAF = 36 deg

| Surface | | Radius of curvature (mm) | Thickness (mm) | Material | Refractive index | Abbe number | Focal length (mm) |
|---|---|---|---|---|---|---|---|
| 0 | Object | 1E+18 | 600 | | | | |
| 1 | 1st lens | 0.840352226 | 0.468 | plastic | 1.535 | 56.27 | 2.232 |
| 2 | | 2.271975602 | 0.148 | | | | |
| 3 | Aperture | 1E+18 | 0.277 | | | | |
| 4 | 2nd lens | −1.157324239 | 0.349 | plastic | 1.642 | 22.46 | −5.221 |
| 5 | | −1.968404008 | 0.221 | | | | |
| 6 | 3rd lens | 1.151874235 | 0.559 | plastic | 1.544 | 56.09 | 7.360 |
| 7 | | 1.338105159 | 0.123 | | | | |
| 8 | Infrared rays filter | 1E+18 | 0.210 | BK7 | 1.517 | 64.13 | |
| 9 | | 1E+18 | 0.547 | | | | |
| 10 | Image plane | 1E+18 | 0.000 | | | | |

Reference wavelength (d-line): 555 nm; the position of blocking light: the effective radius of the clear aperture of the first surface is 0.640 mm.

TABLE 12

| | Coefficients of the aspheric surfaces | | | | | |
|---|---|---|---|---|---|---|
| Surface | 1 | 2 | 4 | 5 | 6 | 7 |
| k | −2.019203E−01 | 1.528275E+01 | 3.743939E+00 | −1.207814E+01 | −1.276860E+01 | −3.034004E+00 |
| A4 | 3.944883E−02 | −1.670490E−01 | −4.266331E−01 | −1.696843E+00 | −7.396546E−01 | −5.308488E−01 |
| A6 | 4.774062E−01 | 3.857435E+00 | −1.423859E+00 | 5.164775E+00 | 4.449101E−01 | 4.374142E−01 |
| A8 | −1.528780E+00 | −7.091408E+01 | 4.119587E+01 | −1.445541E+01 | 2.622372E−01 | −3.111192E−01 |
| A10 | 5.133947E+00 | 6.365801E+02 | −3.456462E+02 | 2.876958E+01 | −2.510946E−01 | 1.354257E−01 |
| A12 | −6.250496E+00 | −3.141002E+03 | 1.495452E+03 | −2.662400E+01 | −1.048030E−01 | −2.652902E−02 |
| A14 | 1.068803E+00 | 7.962834E+03 | −2.747802E+03 | 1.661634E+01 | 1.462137E−01 | −1.203306E−03 |
| A16 | 7.995491E+00 | −8.268637E+03 | 1.443133E+03 | −1.327827E+01 | −3.676651E−02 | 7.805611E−04 |

An equation of the aspheric surfaces of the sixth optical embodiment is the same as that of the first optical embodiment, and the definitions are the same as well.

The exact parameters of the sixth optical embodiment based on Table 11 and Table 12 are listed in the following table:

| Sixth optical embodiment (Reference wavelength: 555 nm) | | | | | |
|---|---|---|---|---|---|
| |f/f1| | |f/f2| | |f/f3| | |f1/f2| | |f2/f3| | TP1/TP2 |
| 1.08042 | 0.46186 | 0.32763 | 2.33928 | 1.40968 | 1.33921 |
| ΣPPR | ΣNPR | ΣPPR/|ΣNPR| | IN12/f | IN23/f | TP2/TP3 |
| 1.40805 | 0.46186 | 3.04866 | 0.17636 | 0.09155 | 0.62498 |
| TP2/(IN12 +TP2+ IN23) | | (TP1 + IN12)/TP2 | | (TP3 + IN23)/TP2 | |
| 0.35102 | | 2.23183 | | 2.23183 | |
| HOS | InTL | HOS/HOI | InS/HOS | |ODT| % | |TDT| % |
| 2.90175 | 2.02243 | 1.61928 | 0.78770 | 1.50000 | 0.71008 |
| HVT21 | HVT22 | HVT31 | HVT32 | HVT32/HOI | HVT32/HOS |
| 0.00000 | 0.00000 | 0.46887 | 0.67544 | 0.37692 | 0.23277 |
| PhiA | | | | | HOI |
| 2.716 mm | | | | | 1.792 mm |
| | | | | | InTL/HOS |
| | | | | | 0.6970 |

-continued

| Sixth optical embodiment (Reference wavelength: 555 nm) | | | | | |
|---|---|---|---|---|---|
| PLTA | PSTA | NLTA | NSTA | SLTA | SSTA |
| −0.002mm | 0.008mm | 0.006mm | −0.008mm | −0.007mm | 0.006mm |

The results of the equations of the sixth optical embodiment based on Table 11 and Table 12 are listed in the following table:

| Values related to the inflection points of the sixth optical embodiment (Reference wavelength: 555 nm) | | | | | | | |
|---|---|---|---|---|---|---|---|
| HIF221 | 0.5599 | HIF221/HOI | 0.3125 | SGI221 | −0.1487 | |SGI221|/(|SGI221| + TP2) | 0.2412 |
| HIF311 | 0.2405 | HIF311/HOI | 0.1342 | SGI311 | 0.0201 | |SGI311|/(|SGI311| + TP3) | 0.0413 |
| HIF312 | 0.8255 | HIF312/HOI | 0.4607 | SGI312 | −0.0234 | |SGI312|/(|SGI312| + TP3) | 0.0476 |
| HIF321 | 0.3505 | HIF321/HOI | 0.1956 | SGI321 | 0.0371 | |SGI321|/(|SGI321| + TP3) | 0.0735 |

The figures related to the profile curve lengths obtained based on Table 11 and Table 12 are listed in the following table:

| Sixth optical embodiment (Reference wavelength: 555 nm) | | | | | | |
|---|---|---|---|---|---|---|
| ARE | 1/2(HEP) | ARE value | ARE−1/2(HEP) | 2(ARE/HEP) % | TP | ARE/TP (%) |
| 11 | 0.546 | 0.598 | 0.052 | 109.49% | 0.468 | 127.80% |
| 12 | 0.500 | 0.506 | 0.005 | 101.06% | 0.468 | 108.03% |
| 21 | 0.492 | 0.528 | 0.036 | 107.37% | 0.349 | 151.10% |
| 22 | 0.546 | 0.572 | 0.026 | 104.78% | 0.349 | 163.78% |
| 31 | 0.546 | 0.548 | 0.002 | 100.36% | 0.559 | 98.04% |
| 32 | 0.546 | 0.550 | 0.004 | 100.80% | 0.559 | 98.47% |
| ARS | EHD | ARS value | ARS−EHD | (ARS/EHD) % | TP | ARS/TP (%) |
| 11 | 0.640 | 0.739 | 0.099 | 115.54% | 0.468 | 158.03% |
| 12 | 0.500 | 0.506 | 0.005 | 101.06% | 0.468 | 108.03% |
| 21 | 0.492 | 0.528 | 0.036 | 107.37% | 0.349 | 151.10% |
| 22 | 0.706 | 0.750 | 0.044 | 106.28% | 0.349 | 214.72% |
| 31 | 1.118 | 1.135 | 0.017 | 101.49% | 0.559 | 203.04% |
| 32 | 1.358 | 1.489 | 0.131 | 109.69% | 0.559 | 266.34% |

The optical image capturing system of the present invention could reduce the required mechanism space by changing the number of lens.

It must be pointed out that the embodiments described above are only some embodiments of the present invention. All equivalent structures which employ the concepts disclosed in this specification and the appended claims should fall within the scope of the present invention.

What is claimed is:

1. A movable carrier auxiliary system, comprising:
a driver state detecting device comprising a physiological state detecting module, a storage module, and an operation module; wherein the physiological state detecting module is adapted to detect at least one physiological state of a driver; the storage module is disposed in a movable carrier and stores at least one allowable parameter corresponding to the at least one physiological state; the operation module is disposed in the movable carrier and is electrically connected to the physiological state detecting module and the storage module to detect whether the at least one physiological state of the driver exceeds the at least one allowable parameter or not, and to correspondingly generate a detection signal; and a warning device which is electrically connected to the operation module and is adapted to generate a warning message when the detection signal that the at least one physiological state of the driver exceeds the at least one allowable parameter is received;

wherein the physiological state detecting module comprises an image capturing module for capturing a driver image located on a driver seat in the movable carrier; the operation module determines whether the at least one physiological state of the driver exceeds the at least one allowable parameter or not based on the driver image and correspondingly generates the detection signal;

wherein the image capturing module has a lens group; the lens group comprises at least two lenses having refractive power and satisfies:

$1.0 \le f/HEP \le 10.0$;
$0 \deg < HAF \le 150 \deg$; and
$0.9 \le 2(ARE/HEP) \le 2.0$;

wherein f is a focal length of the lens group; HEP is an entrance pupil diameter of the lens group; HAF is a half of a maximum field angle of the lens group; for any surface of any lens, ARE is a profile curve length measured from a start point where an optical axis of the lens group passes through any surface of one of the at least two lenses, along a surface profile of the corresponding lens, and finally to a coordinate point, from which a vertical distance to the optical axis is half of the entrance pupil diameter.

2. The movable carrier auxiliary system of claim 1, further comprising a control device which is disposed on the movable carrier and is electrically connected to the operation module and the storage module, wherein the storage module further stores a plurality of operating modes corresponding to whether the at least one physiological state of the driver exceeds the at least one allowable parameter or not; the control device correspondingly reads one of the operating modes from the storage module to control the movable carrier based on the detection signal that whether the at least one physiological state of the driver exceeds the at least one allowable parameter or not.

3. The movable carrier auxiliary system of claim 2, further comprising a starting device electrically connected to the control device, wherein the driver starts or turns off a power system of the movable carrier by manipulating the starting device; when the movable carrier is in a state that the power system is turned off, and the driver is about to start the power system via the starting device, and the control device receives the detection signal that the at least one physiological state of the driver does not exceed the at least one allowable parameter, the control device controls the movable carrier in one of the operating modes that allows the movable carrier to be started by the power system; when the movable carrier is in a state that the power system is turned off, and the driver is about to start the power system via the starting device, and the control device receives the detection signal that the at least one physiological state of the driver exceeds the at least one allowable parameter, the control device controls the movable carrier in one of the operating modes that disallows the movable carrier to be started by the power system.

4. The movable carrier auxiliary system of claim 3, wherein the physiological state detecting module is disposed on the starting device.

5. The movable carrier auxiliary system of claim 4, wherein the starting device is disposed in the movable carrier.

6. The movable carrier auxiliary system of claim 3, wherein when the movable carrier is in a state that the power system starts, and the control device receives the detection signal that at least one of the physiological state of the driver exceeds the at least one allowable parameter for a predetermined time, the control device controls the movable carrier in one of the operating modes that the movable carrier is automatically driven.

7. The movable carrier auxiliary system of claim 6, further comprising a vehicle state detecting device which is disposed on the movable carrier and is adapted to detect a movement state of the movable carrier and correspondingly generates a state signal; wherein the control device is electrically connected to the vehicle state detecting device, thereby to control the movable carrier in one of the operating modes that the movable carrier is automatically driven based on the state signal.

8. The movable carrier auxiliary system of claim 1, wherein the storage module further stores at least one emergency contact information; the warning device is electrically connected to the storage module, thereby to send the warning message to the at least one emergency contact information.

9. The movable carrier auxiliary system of claim 1, further comprising a warning member electrically connected to the warning device for correspondingly generating light, sound, vibration, or physical touch the driver when the warning device sends the warning message.

10. The movable carrier auxiliary system of claim 1, further comprising a displaying device electrically connected to the warning device for displaying the warning message.

11. The movable carrier auxiliary system of claim 10, wherein the warning message is displayed on the displaying device as an image, a text, or both of the image and the text.

12. The movable carrier auxiliary system of claim 10, wherein the displaying device is a vehicle electronic rearview mirror.

13. The movable carrier auxiliary system of claim 12, wherein the displaying device comprises:
  a first transparent assembly having a first incidence surface and a first exit surface, wherein an image enters the first transparent assembly via the first incidence surface, and is emitted via the first exit surface;
  a second transparent assembly disposed on the first exit surface, wherein a gap is formed between the second transparent assembly and the first transparent assembly; the second transparent assembly comprises a second incidence surface and a second exit surface; the image is emitted to the second transparent assembly from the first exit surface and is emitted via the second exit surface;
  an electro-optic medium layer disposed in the gap and formed between the first exit surface of the first transparent assembly and the second incidence surface of the second transparent assembly;
  at least one transparent electrode disposed between the first transparent assembly and the electro-optic medium layer;
  at least one reflective layer, wherein the electro-optic medium layer is disposed between the first transparent assembly and the at least one reflective layer;
  at least one transparent conductive layer disposed between the electro-optic medium layer and the at least one reflective layer;
  at least one electrical connector electrically connected to the electro-optic medium layer, wherein the at least one electrical connector transmits an electrical energy to the electro-optic medium layer to change a transparency of the electro-optic medium layer; and
  at least one control member electrically connected to the at least one electrical connector, wherein when a luminance of the image exceeds a certain luminance, the at least one control member controls the at least one electrical connector to supply the electrical energy to the electro-optic medium layer.

14. The movable carrier auxiliary system of claim 1, wherein the physiological state detecting module is disposed on a wearable device of the driver, so that the physiological state detecting module enters or leaves the movable carrier along with the driver.

15. The movable carrier auxiliary system of claim 1, wherein the at least one physiological state of the driver that the operation module analyzes based on the driver image is at least one of whether a direction of the driver's line of sight is toward a travel direction of the movable carrier, a time that the driver's line of sight changes, a frequency that the driver's line of sight changes, a time that the driver's eyes close, a frequency that the driver's eyes blink, and the storage module correspondingly stores the at least one allowable parameter.

16. The movable carrier auxiliary system of claim 1, wherein the physiological state detecting module further comprises a heart rate detecting module for being touched by the driver; the at least one physiological state of the driver that the heart rate detecting module detects is heart rhythm or heart rate variation, and the storage module correspondingly stores the at least one allowable parameter.

17. The movable carrier auxiliary system of claim 16, wherein the warning device generates the warning message when the warning device receives the detection signal that both of the physiological states of the driver detected by the image capturing module and the heart rate detecting module exceed the at least one allowable parameter.

18. The movable carrier auxiliary system of claim 16, wherein the warning device generates the warning message when the warning device receives the detection signal that at least one of the physiological states of the driver detected by the image capturing module and the heart rate detecting module exceeds the at least one allowable parameter.

19. The movable carrier auxiliary system of claim 1, wherein the physiological state detecting module further comprises a blood pressure detecting module for being touched by the driver; the at least one physiological state of the driver that the blood pressure detecting module detects is blood pressure or blood pressure variation, and the storage module correspondingly stores the at least one allowable parameter.

20. The movable carrier auxiliary system of claim 19, wherein the warning device generates the warning message when the warning device receives the detection signal that both of the physiological states of the driver detected by the image capturing module and the blood pressure detecting module exceed the at least one allowable parameter.

21. The movable carrier auxiliary system of claim 19, wherein the warning device generates the warning message when the warning device receives the detection signal that at least one of the physiological states of the driver detected by the image capturing module and the blood pressure detecting module exceeds the at least one allowable parameter.

22. The movable carrier auxiliary system of claim 1, wherein the physiological state detecting module further comprises a blood component detecting module; the at least one physiological state of the driver that the blood component detecting module detects is alcohol concentration, blood oxygen concentration or blood glucose concentration in the driver's blood, and the storage module correspondingly stores the at least one allowable parameter.

23. The movable carrier auxiliary system of claim 22, wherein the warning device generates the warning message when the warning device receives the detection signal that both of the physiological states of the driver detected by the image capturing module and the blood component detecting module exceed the at least one allowable parameter.

24. The movable carrier auxiliary system of claim 22, wherein the warning device generates the warning message when the warning device receives the detection signal that at least one of the physiological states of the driver detected by the image capturing module and the blood component detecting module exceeds the at least one allowable parameter.

25. The movable carrier auxiliary system of claim 1, wherein the physiological state detecting module further comprises an alcohol concentration detecting module; the at least one physiological state of the driver that the alcohol concentration detecting module detects is alcohol concentration that the driver breathes out or alcohol concentration in the driver's blood, and the storage module correspondingly stores the at least one allowable parameter; the warning device generates the warning message when the warning device receives the detection signal that the at least one physiological state of the driver detected by the alcohol concentration detecting module exceeds the at least one allowable parameter.

26. The movable carrier auxiliary system of claim 25, further comprising a control device and a starting device, wherein the control device is disposed on the movable carrier and is electrically connected to the operation module and the storage module; the starting device is electrically connected to the control device; the driver starts or turns off a power system of the movable carrier by manipulating the starting device; when the movable carrier is in a state that the power system is turned off, and the driver is about to start the power system via the starting device, and the control device receives the detection signal that the at least one physiological state of the driver detected by the alcohol concentration detecting module does not exceed the at least one allowable parameter, the control device controls the movable carrier in one of the operating modes that allows the movable carrier to be started by the power system; when the movable carrier is in a state that the power system is turned off, and the driver is about to start the power system via the starting device, and the control device receives the detection signal that the at least one physiological state of the driver detected by the alcohol concentration detecting module exceeds the at least one allowable parameter, the control device controls the movable carrier in one of the operating modes that disallows the movable carrier to be started by the power system.

27. The movable carrier auxiliary system of claim 26, wherein the alcohol concentration detecting module is disposed on the starting device; the starting device is disposed in the movable carrier and has a starting button which is adapted to be pressed by the driver to operate the starting device to start or turn off the power system.

28. The movable carrier auxiliary system of claim 25, wherein the alcohol concentration detecting module is disposed on a gear shift device of the movable carrier, so that the driver manipulates the gear shift device to switch a movement state of the movable carrier; when the driver manipulates the gear shift device, a hand of the driver is in contact with the alcohol concentration detecting module on the gear shift device.

29. The movable carrier auxiliary system of claim 25, wherein the physiological state detecting module is disposed on a wearable device of the driver, so that the physiological state detecting module enters or leaves the movable carrier along with the driver.

30. The movable carrier auxiliary system of claim 1, wherein the physiological state detecting module further comprises a respiratory rate detecting module for detecting a respiratory rate of the driver, the at least one physiological state of the driver that the respiratory rate detecting module detects is respiratory rate, and the storage module correspondingly stores the at least one allowable parameter.

31. The movable carrier auxiliary system of claim 30, wherein the warning device generates the warning message when the warning device receives the detection signal that both of the physiological states of the driver detected by the image capturing module and the respiratory rate detecting module exceed the at least one allowable parameter.

32. The movable carrier auxiliary system of claim 1, further comprising an update module electrically connected to the storage module for updating the at least one allowable parameter stored in the storage module.

33. The movable carrier auxiliary system of claim 1, wherein the physiological state detecting module further comprises a luminance sensor electrically connected to the at least one image capturing module for detecting a luminance on at least a direction in which the at least one image capturing module captures the image; when the luminance measured by the luminance sensor is greater than an upper threshold, the at least one image capturing module captures the driver image in a way that reduce an amount of light entering; when the luminance measured by the luminance sensor is less than a lower threshold, the at least one image capturing module captures the driver image in a way that increase the amount of light entering.

34. The movable carrier auxiliary system of claim 1, wherein the lens group satisfies:

$0.9 \leq ARS/EHD \leq 2.0$;

wherein for any surface of any lens, ARS is a profile curve length measured from a start point where the optical axis passes therethrough, along a surface profile thereof, and finally to an end point of a maximum effective radius thereof; and EHD is a maximum effective radius thereof.

35. The movable carrier auxiliary system of claim 1, wherein the lens group satisfies:

$PLTA \leq 100$ μm;
$PSTA \leq 100$ μm;
$NLTA \leq 100$ μm;
$NSTA \leq 100$ μm;
$SLTA \leq 100$ μm;
$SSTA \leq 100$ μm;
and $|TDT| < 250\%$;

wherein HOI is a maximum imaging height for image formation perpendicular to the optical axis on an image plane of the at least one image capturing module; PLTA is a transverse aberration at 0.7 HOI in a positive direction of a tangential ray fan aberration of the at least one image capturing module after the longest operation wavelength passing through an edge of the entrance pupil; PSTA is a transverse aberration at 0.7 HOI in the positive direction of the tangential ray fan aberration of the at least one image capturing module after the shortest operation wavelength passing through the edge of the entrance pupil; NLTA is a transverse aberration at 0.7 HOI in a negative direction of the tangential ray fan aberration of the at least one image capturing module after the longest operation wavelength passing through the edge of the entrance pupil; NSTA is a transverse aberration at 0.7 HOI in the negative direction of the tangential ray fan aberration of the at least one image capturing module after the shortest operation wavelength passing through the edge of the entrance pupil; SLTA is a transverse aberration at 0.7 HOI of a sagittal ray fan aberration of the at least one image capturing module after the longest operation wavelength passing through the edge of the entrance pupil; SSTA is a transverse aberration at 0.7 HOI of the sagittal ray fan aberration of the at least one image capturing module after the shortest operation wavelength passing through the edge of the entrance pupil; TDT is a TV distortion of the at least one image capturing module upon image formation.

36. The movable carrier auxiliary system of claim 1, wherein the lens group comprises four lenses having refractive power, which are constituted by a first lens, a second lens, a third lens, and a fourth lens in order along the optical axis from an object side to an image side; and the lens group satisfies:

$0.1 \leq InTL/HOS \leq 0.95$;

wherein HOS is a distance in parallel with the optical axis between an object-side surface of the first lens and an image plane of the at least one image capturing module; InTL is a distance in parallel with the optical axis from the object-side surface of the first lens to an image-side surface of the fourth lens.

37. The movable carrier auxiliary system of claim 1, wherein the lens group comprises five lenses having refractive power, which are constituted by a first lens, a second lens, a third lens, a fourth lens, and a fifth lens in order along the optical axis from an object side to an image side; and the lens group satisfies:

$0.1 \leq InTL/HOS \leq 0.95$;

wherein HOS is a distance in parallel with the optical axis between an object-side surface of the first lens and an image plane of the at least one image capturing module; InTL is a distance in parallel with the optical axis from the object-side surface of the first lens to an image-side surface of the fifth lens.

38. The movable carrier auxiliary system of claim 1, wherein the lens group comprises six lenses having refractive power, which are constituted by a first lens, a second lens, a third lens, a fourth lens, a fifth lens, and a sixth lens in order along the optical axis from an object side to an image side; and the lens group satisfies:

$0.1 \leq InTL/HOS \leq 0.95$;

wherein HOS is a distance in parallel with the optical axis between an object-side surface of the first lens and an image plane of the at least one image capturing module; InTL is a distance in parallel with the optical axis from the object-side surface of the first lens to an image-side surface of the sixth lens.

39. The movable carrier auxiliary system of claim 1, wherein the lens group comprises seven lenses having refractive power, which are constituted by a first lens, a second lens, a third lens, a fourth lens, a fifth lens, a sixth lens, and a seventh lens in order along the optical axis from an object side to an image side; and the lens group satisfies:

$0.1 \leq InTL/HOS \leq 0.95$;

wherein HOS is a distance in parallel with the optical axis between an object-side surface of the first lens and an image plane of the at least one image capturing module; InTL is a distance in parallel with the optical axis from the object-side surface of the first lens to an image-side surface of the seventh lens.

40. The movable carrier auxiliary system of claim 1, wherein the lens group further comprises an aperture, and the aperture satisfies:

$0.2 \leq InS/HOS \leq 1.1$;

wherein HOS is a distance in parallel with the optical axis between a lens surface of the lens group furthest from an image plane of the at least one image capturing module and the image plane; InS is a distance on the optical axis between the aperture and the image plane of the at least one image capturing module.

* * * * *